US011890443B2

(12) United States Patent
Hamatake et al.

(10) Patent No.: US 11,890,443 B2
(45) **Date of Patent: *Feb. 6, 2024**

(54) IMPLANTABLE MEDICAL DEVICES INCLUDING SEPTUM-BASED INDICATORS

(71) Applicant: C. R. Bard, Inc., Franklin Lakes, NJ (US)

(72) Inventors: Bret Hamatake, Grantsville, UT (US); John G. Evans, South Jordan, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 722 days.

This patent is subject to a terminal disclaimer.

(21) Appl. No.: 17/020,691

(22) Filed: Sep. 14, 2020

(65) Prior Publication Data

US 2022/0080174 A1 Mar. 17, 2022

Related U.S. Application Data

(60) Continuation of application No. 16/105,774, filed on Aug. 20, 2018, now Pat. No. 10,773,066, which is a (Continued)

(51) Int. Cl.
*A61M 39/02* (2006.01)

(52) U.S. Cl.
CPC . *A61M 39/0208* (2013.01); *A61M 2039/0214* (2013.01); *A61M 2039/0235* (2013.01); *A61M 2039/0238* (2013.01)

(58) Field of Classification Search
CPC ...... A61M 39/0208; A61M 2039/0214; A61M 2039/0235; A61M 2039/0238
See application file for complete search history.

(56) References Cited

U.S. PATENT DOCUMENTS

| | | | |
|---|---|---|---|
| 445,896 | A | 2/1891 | Kinsman |
| 546,440 | A | 9/1895 | Tufts |

(Continued)

FOREIGN PATENT DOCUMENTS

| | | | |
|---|---|---|---|
| AU | 2008299945 | A1 | 3/2009 |
| CA | 2663853 | A1 | 4/2008 |

(Continued)

OTHER PUBLICATIONS

U.S. Appl. No. 13/853,961, filed Mar. 29, 2013 Non-Final Office Action dated Sep. 12, 2014.

(Continued)

*Primary Examiner* — Theodore J Stigell
(74) *Attorney, Agent, or Firm* — Rutan & Tucker LLP

(57) ABSTRACT

A method of making an access port, includes providing a port body defining a fluid cavity, positioning a septum over the fluid cavity, and securing the septum to the port body. The septum includes a lower portion having a first diameter, an upper portion joined to the lower portion at a juncture, the upper portion having a second diameter less than the first diameter at the juncture, and a plurality of palpation features joined to the upper portion. Each of the palpation features includes a first end adjacent a central axis of the septum, and a second end extending radially outward, overlapping the juncture.

10 Claims, 15 Drawing Sheets

Related U.S. Application Data division of application No. 14/587,862, filed on Dec. 31, 2014, now Pat. No. 10,052,471, which is a division of application No. 12/617,981, filed on Nov. 13, 2009, now Pat. No. 8,932,271.

(60) Provisional application No. 61/114,331, filed on Nov. 13, 2008.

(56) References Cited

U.S. PATENT DOCUMENTS 574,387 A 1/1897 Buckler
611,357 A 9/1898 Dembinski
966,696 A 8/1910 Merrill
D44,302 S 7/1913 Director
1,713,267 A 5/1929 Crowley
D130,852 S 12/1941 Rothschild
2,433,480 A 12/1947 Rendich
2,891,689 A 6/1959 Gould
3,159,175 A 12/1964 Macmillan
3,211,431 A 10/1965 Meysembourg et al.
3,293,663 A 12/1966 Cronin
3,341,417 A 9/1967 Sinaiko
3,477,438 A 11/1969 Allen et al.
3,518,428 A 6/1970 Ring
3,525,357 A 8/1970 Koreski
3,529,633 A 9/1970 Vaillancourt
3,540,670 A 11/1970 Rissberger
3,643,358 A 2/1972 Morderosian
3,669,323 A 6/1972 Harker et al.
3,674,183 A 7/1972 Venable et al.
3,811,466 A 5/1974 Ohringer
3,829,904 A 8/1974 Ling et al.
3,831,549 A 8/1974 Parsons
3,831,583 A 8/1974 Edmunds, Jr. et al.
3,840,009 A 10/1974 Michaels et al.
3,853,127 A 12/1974 Spademan
3,891,997 A 7/1975 Herbert
3,915,162 A 10/1975 Miller
3,919,724 A 11/1975 Sanders et al.
3,922,726 A 12/1975 Trentani et al.
3,951,147 A 4/1976 Tucker et al.
3,955,594 A 5/1976 Snow
3,971,376 A 7/1976 Wichterle
4,013,064 A 3/1977 Patel et al.
4,027,391 A 6/1977 Samis
4,035,653 A 7/1977 Karasko
4,121,108 A 10/1978 Manor
4,123,806 A 11/1978 Amstutz et al.
4,143,853 A 3/1979 Abramson
4,168,586 A 9/1979 Samis
4,181,132 A 1/1980 Parks
4,190,040 A 2/1980 Schulte
4,190,057 A 2/1980 Hill et al.
4,194,122 A 3/1980 Mitchell et al.
4,196,731 A 4/1980 Laurin et al.
4,202,349 A 5/1980 Jones
4,214,593 A 7/1980 Imbruce et al.
4,222,374 A 9/1980 Sampson et al.
4,233,964 A 11/1980 Jefferts et al.
4,274,006 A 6/1981 Caine
4,286,597 A 9/1981 Gajewski et al.
D263,335 S 3/1982 Bujan
4,349,498 A 9/1982 Ellis et al.
4,361,153 A 11/1982 Slocum et al.
4,405,305 A 9/1983 Stephen et al.
4,406,567 A 9/1983 Samis
4,425,119 A 1/1984 Berglund
4,445,896 A 5/1984 Gianturco
4,447,237 A 5/1984 Frisch et al.
4,450,592 A 5/1984 Niederer et al.
4,450,985 A 5/1984 Beard
4,456,011 A 6/1984 Warnecke
4,469,483 A 9/1984 Becker et al.
4,479,798 A 10/1984 Parks
4,494,545 A 1/1985 Slocum et al.
4,506,676 A 3/1985 Duska
4,529,635 A 7/1985 Sheldon
4,543,088 A 9/1985 Bootman et al.
4,549,879 A 10/1985 Groshong et al.
4,559,043 A 12/1985 Whitehouse et al.
4,559,046 A 12/1985 Groshong et al.
4,560,375 A 12/1985 Schulte et al.
4,569,675 A 2/1986 Prosl et al.
4,571,749 A 2/1986 Fischell
4,576,595 A 3/1986 Aas et al.
4,602,645 A 7/1986 Barrington et al.
4,610,665 A 9/1986 Matsumoto et al.
4,612,877 A 9/1986 Hayes et al.
4,626,244 A 12/1986 Reinicke
4,627,844 A 12/1986 Schmitt
4,634,427 A 1/1987 Hannula et al.
4,636,194 A 1/1987 Schulte et al.
4,636,213 A 1/1987 Pakiam
4,645,495 A 2/1987 Vaillancourt
4,653,508 A 3/1987 Cosman
4,655,765 A 4/1987 Swift
4,657,024 A 4/1987 Coneys
4,662,652 A 5/1987 Hargis
4,668,221 A 5/1987 Luther
4,671,796 A 6/1987 Groshong et al.
4,673,394 A 6/1987 Fenton, Jr. et al.
4,681,560 A 7/1987 Schulte et al.
4,684,365 A 8/1987 Reinicke
4,685,447 A 8/1987 Iversen et al.
4,685,905 A 8/1987 Jeanneret
4,692,146 A 9/1987 Hilger
4,695,273 A 9/1987 Brown
4,697,595 A 10/1987 Breyer et al.
4,701,166 A 10/1987 Groshong et al.
4,704,103 A 11/1987 Stober et al.
4,707,389 A 11/1987 Ward
4,710,167 A 12/1987 Lazorthes
4,710,174 A 12/1987 Moden et al.
4,718,894 A 1/1988 Lazorthes
4,723,947 A 2/1988 Konopka
4,728,894 A 3/1988 Yoda et al.
4,743,231 A 5/1988 Kay et al.
4,753,640 A 6/1988 Nichols et al.
4,755,173 A 7/1988 Konopka et al.
4,760,837 A 8/1988 Petit
4,762,517 A 8/1988 McIntyre et al.
4,767,410 A 8/1988 Moden et al.
4,772,270 A 9/1988 Wiita et al.
4,772,276 A 9/1988 Wiita et al.
4,773,552 A 9/1988 Boege et al.
4,778,452 A 10/1988 Moden et al.
4,781,680 A 11/1988 Redmond et al.
4,781,685 A 11/1988 Lehmann et al.
4,781,695 A 11/1988 Dalton
4,784,646 A 11/1988 Feingold
4,793,635 A 12/1988 Lovison
4,802,885 A 2/1989 Weeks et al.
4,804,054 A 2/1989 Howson et al.
4,820,273 A 4/1989 Reinicke
4,822,341 A 4/1989 Colone
4,840,615 A 6/1989 Hancock et al.
4,848,346 A 7/1989 Crawford
4,857,053 A 8/1989 Dalton
4,861,341 A 8/1989 Woodburn
4,863,470 A 9/1989 Carter
4,886,501 A 12/1989 Johnston et al.
4,886,502 A 12/1989 Poirier et al.
4,892,518 A 1/1990 Cupp et al.
4,895,561 A 1/1990 Mahurkar
4,897,081 A 1/1990 Poirier et al.
4,904,241 A 2/1990 Bark
4,905,709 A 3/1990 Bieganski et al.
4,908,029 A 3/1990 Bark et al.
4,909,250 A 3/1990 Smith
4,915,690 A 4/1990 Cone et al.
4,928,298 A 5/1990 Tanaka
4,929,236 A 5/1990 Sampson
4,955,861 A 9/1990 Enegren et al.

(56) References Cited

U.S. PATENT DOCUMENTS 4,961,267 A 10/1990 Herzog
4,963,133 A 10/1990 Whipple
4,966,583 A 10/1990 Debbas
4,973,319 A 11/1990 Melsky
4,983,162 A 1/1991 Metais et al.
5,002,735 A 3/1991 Alberhasky et al.
5,006,115 A 4/1991 McDonald
5,009,391 A 4/1991 Steigerwald
5,009,644 A 4/1991 McDonald
5,013,298 A 5/1991 Moden et al.
5,041,098 A 8/1991 Loiterman et al.
5,044,955 A 9/1991 Jagmin
5,045,060 A 9/1991 Melsky et al.
5,045,064 A 9/1991 Idriss
5,045,071 A 9/1991 McCormick et al.
5,053,013 A 10/1991 Ensminger et al.
5,059,186 A 10/1991 Yamamoto et al.
5,069,206 A 12/1991 Crosbie
5,084,015 A 1/1992 Moriuchi
5,085,216 A 2/1992 Henley, Jr. et al.
5,090,066 A 2/1992 Schoepe et al.
5,092,849 A 3/1992 Sampson
5,108,317 A 4/1992 Beinhaur et al.
5,108,375 A 4/1992 Harrison et al.
5,108,377 A 4/1992 Cone et al.
5,112,301 A 5/1992 Fenton, Jr. et al.
5,112,303 A 5/1992 Pudenz et al.
5,129,891 A 7/1992 Young
5,137,529 A 8/1992 Watson et al.
5,147,483 A 9/1992 Melsky et al.
5,152,753 A 10/1992 Laguette et al.
5,156,600 A 10/1992 Young
5,158,547 A 10/1992 Doan et al.
5,167,629 A 12/1992 Vertenstein et al.
5,167,633 A 12/1992 Mann et al.
5,167,638 A 12/1992 Felix et al.
5,169,393 A 12/1992 Moorehead et al.
5,171,228 A 12/1992 McDonald
5,176,653 A 1/1993 Metals
5,176,662 A 1/1993 Bartholomew et al.
5,178,612 A 1/1993 Fenton, Jr.
5,180,365 A 1/1993 Ensminger et al.
5,185,003 A 2/1993 Brethauer
5,189,690 A 2/1993 Samuel
5,193,106 A 3/1993 DeSena
5,195,122 A 3/1993 Fabian
5,195,123 A 3/1993 Clement
5,201,715 A 4/1993 Masters
5,201,722 A 4/1993 Moorehead et al.
5,203,771 A 4/1993 Melker et al.
5,203,777 A 4/1993 Lee
5,205,834 A 4/1993 Moorehead et al.
5,207,644 A 5/1993 Strecker
5,213,574 A 5/1993 Tucker
5,215,537 A 6/1993 Lynn et al.
5,222,499 A 6/1993 Allen et al.
5,222,982 A 6/1993 Ommaya
D337,637 S 7/1993 Tucker
5,224,938 A 7/1993 Fenton, Jr.
5,242,415 A 9/1993 Kantrowitz et al.
5,246,462 A 9/1993 Bekki et al.
5,249,598 A 10/1993 Schmidt
5,263,930 A 11/1993 Ensminger
D342,134 S 12/1993 Mongeon
5,281,199 A 1/1994 Ensminger et al.
5,281,205 A 1/1994 McPherson
5,290,263 A 3/1994 Wigness et al.
5,292,305 A 3/1994 Boudewijn et al.
5,295,658 A 3/1994 Atkinson et al.
5,299,253 A 3/1994 Wessels
5,300,048 A 4/1994 Drewes, Jr. et al.
5,309,863 A 5/1994 Leeb, Jr.
5,312,337 A 5/1994 Flaherty et al.
5,318,545 A 6/1994 Tucker
5,320,100 A 6/1994 Herweck et al.
5,328,480 A 7/1994 Melker et al.
5,332,398 A 7/1994 Miller et al.
5,336,194 A 8/1994 Polaschegg et al.
5,338,398 A 8/1994 Szwejkowski et al.
5,350,360 A 9/1994 Ensminger et al.
5,352,204 A 10/1994 Ensminger
5,356,381 A 10/1994 Ensminger et al.
5,360,407 A 11/1994 Leonard et al.
5,383,223 A 1/1995 Inokuchi
5,383,233 A 1/1995 Russell
5,383,585 A 1/1995 Weiss
5,383,858 A 1/1995 Reilly et al.
D355,240 S 2/1995 Gladfelter et al.
5,387,192 A 2/1995 Glantz et al.
5,394,457 A 2/1995 Leibinger et al.
5,395,324 A 3/1995 Hinrichs et al.
5,396,925 A 3/1995 Poli
5,397,329 A 3/1995 Allen
5,399,168 A 3/1995 Wadsworth, Jr. et al.
5,405,402 A 4/1995 Dye et al.
5,415,639 A 5/1995 VandenEinde et al.
5,417,565 A 5/1995 Long
5,417,656 A 5/1995 Ensminger et al.
5,421,814 A 6/1995 Geary
5,423,334 A 6/1995 Jordan
5,425,762 A 6/1995 Muller
5,453,097 A 9/1995 Paradis
5,456,698 A 10/1995 Byland et al.
5,476,451 A 12/1995 Ensminger et al.
5,476,460 A 12/1995 Montalvo
5,476,880 A 12/1995 Cooke et al.
5,484,402 A 1/1996 Saravia et al.
5,489,275 A 2/1996 Thompson et al.
5,503,630 A 4/1996 Ensminger et al.
5,507,813 A 4/1996 Dowd et al.
5,509,805 A 4/1996 Jagmin
5,513,637 A 5/1996 Twiss et al.
5,514,103 A 5/1996 Srisathapat et al.
5,520,632 A 5/1996 Leveen et al.
5,520,643 A 5/1996 Ensminger et al.
5,527,277 A 6/1996 Ensminger et al.
5,527,278 A 6/1996 Ensminger et al.
5,527,307 A 6/1996 Srisathapat et al.
5,531,684 A 7/1996 Ensminger et al.
5,542,923 A 8/1996 Ensminger et al.
5,545,143 A 8/1996 Fischell
5,554,117 A 9/1996 Ensminger et al.
5,556,381 A 9/1996 Ensminger et al.
5,558,641 A 9/1996 Glantz et al.
5,558,829 A 9/1996 Petrick
5,562,617 A 10/1996 Finch, Jr. et al.
5,562,618 A 10/1996 Cai et al.
5,575,770 A 11/1996 Melsky et al.
5,578,013 A 11/1996 Bierman
5,593,028 A 1/1997 Haber et al.
5,593,434 A 1/1997 Williams
5,607,393 A 3/1997 Ensminger et al.
5,607,407 A 3/1997 Tolkoff et al.
5,613,945 A 3/1997 Cai et al.
5,620,419 A 4/1997 Lui et al.
5,632,729 A 5/1997 Cai et al.
5,637,102 A 6/1997 Tolkoff et al.
5,638,832 A 6/1997 Singer et al.
5,647,855 A 7/1997 Trooskin
RE35,601 E 9/1997 Eckenhoff
5,662,600 A 9/1997 Watson et al.
5,662,612 A 9/1997 Niehoff
5,662,616 A 9/1997 Bousquet
5,676,146 A 10/1997 Scarborough
5,695,490 A 12/1997 Flaherty et al.
5,702,128 A 12/1997 Maxim et al.
5,702,363 A 12/1997 Flaherty
5,704,915 A 1/1998 Melsky et al.
5,707,357 A 1/1998 Mikhail et al.
5,709,668 A 1/1998 Wacks
5,713,844 A 2/1998 Peyman
5,713,858 A 2/1998 Heruth et al.
5,713,859 A 2/1998 Finch, Jr. et al.
5,718,382 A 2/1998 Jaeger

(56) References Cited

U.S. PATENT DOCUMENTS

| | | | |
|---|---|---|---|
| 5,718,682 | A | 2/1998 | Tucker |
| 5,725,507 | A | 3/1998 | Petrick |
| 5,733,336 | A | 3/1998 | Neuenfeldt et al. |
| 5,733,400 | A | 3/1998 | Gore et al. |
| 5,741,228 | A | 4/1998 | Lambrecht et al. |
| 5,743,873 | A | 4/1998 | Cai et al. |
| 5,743,891 | A | 4/1998 | Tolkoff et al. |
| 5,746,460 | A | 5/1998 | Marohl et al. |
| 5,755,780 | A | 5/1998 | Finch, Jr. et al. |
| 5,758,667 | A | 6/1998 | Slettenmark |
| 5,769,823 | A | 6/1998 | Otto |
| 5,773,552 | A | 6/1998 | Hutchings et al. |
| 5,776,096 | A | 7/1998 | Fields |
| 5,776,188 | A | 7/1998 | Shepherd et al. |
| 5,792,104 | A | 8/1998 | Speckman et al. |
| 5,792,116 | A | 8/1998 | Berg et al. |
| 5,792,123 | A | 8/1998 | Ensminger |
| 5,797,886 | A | 8/1998 | Roth et al. |
| 5,810,789 | A | 9/1998 | Powers et al. |
| 5,814,016 | A | 9/1998 | Valley et al. |
| 5,817,102 | A | 10/1998 | Johnson et al. |
| 5,824,071 | A | 10/1998 | Nelson et al. |
| 5,830,172 | A | 11/1998 | Leveen et al. |
| 5,833,654 | A | 11/1998 | Powers et al. |
| 5,835,563 | A | 11/1998 | Navab et al. |
| 5,836,935 | A | 11/1998 | Ashton et al. |
| 5,840,063 | A | 11/1998 | Flaherty |
| 5,843,069 | A | 12/1998 | Butler et al. |
| 5,848,989 | A | 12/1998 | Villani |
| 5,851,221 | A | 12/1998 | Rieder et al. |
| 5,853,394 | A | 12/1998 | Tolkoff et al. |
| 5,868,702 | A | 2/1999 | Stevens et al. |
| 5,879,322 | A | 3/1999 | Lattin et al. |
| 5,882,341 | A | 3/1999 | Bousquet |
| 5,882,353 | A | 3/1999 | VanBeek et al. |
| 5,895,424 | A | 4/1999 | Steele, Sr. et al. |
| 5,897,528 | A | 4/1999 | Schultz |
| 5,899,856 | A | 5/1999 | Schoendorfer et al. |
| 5,904,934 | A | 5/1999 | Maruyama et al. |
| 5,906,592 | A | 5/1999 | Kriesel et al. |
| 5,906,596 | A | 5/1999 | Tallarida |
| 5,908,413 | A | 6/1999 | Lange et al. |
| 5,908,414 | A | 6/1999 | Otto et al. |
| 5,911,706 | A | 6/1999 | Estabrook et al. |
| 5,913,998 | A | 6/1999 | Butler et al. |
| 5,916,263 | A | 6/1999 | Goicoechea et al. |
| 5,919,160 | A | 7/1999 | Sanfilippo, II |
| 5,925,017 | A | 7/1999 | Kriesel et al. |
| 5,925,030 | A | 7/1999 | Gross et al. |
| 5,927,345 | A | 7/1999 | Samson |
| 5,928,197 | A | 7/1999 | Niehoff |
| 5,928,744 | A | 7/1999 | Heilmann et al. |
| 5,931,829 | A | 8/1999 | Burbank et al. |
| 5,941,856 | A | 8/1999 | Kovacs et al. |
| 5,944,023 | A | 8/1999 | Johnson et al. |
| 5,944,688 | A | 8/1999 | Lois |
| 5,944,698 | A | 8/1999 | Fischer et al. |
| 5,944,712 | A | 8/1999 | Frassica et al. |
| D413,672 | S | 9/1999 | Fogarty |
| 5,947,953 | A | 9/1999 | Ash et al. |
| 5,951,512 | A | 9/1999 | Dalton |
| 5,951,522 | A | 9/1999 | Rosato et al. |
| 5,951,929 | A | 9/1999 | Wilson |
| 5,954,687 | A | 9/1999 | Baudino |
| 5,954,691 | A | 9/1999 | Prosl |
| 5,957,890 | A | 9/1999 | Mann et al. |
| 5,961,497 | A | 10/1999 | Larkin |
| 5,968,011 | A | 10/1999 | Larsen et al. |
| 5,970,162 | A | 10/1999 | Kawashima |
| 5,989,216 | A | 11/1999 | Johnson et al. |
| 5,989,239 | A | 11/1999 | Finch et al. |
| 5,989,641 | A | 11/1999 | Oulie |
| 5,997,524 | A | 12/1999 | Burbank et al. |
| 6,007,516 | A | 12/1999 | Burbank et al. |
| 6,013,051 | A | 1/2000 | Nelson |
| 6,013,058 | A | 1/2000 | Prosl et al. |
| 6,017,331 | A | 1/2000 | Watts et al. |
| 6,022,335 | A | 2/2000 | Ramadan |
| 6,033,389 | A | 3/2000 | Cornish |
| 6,039,712 | A | 3/2000 | Fogarty et al. |
| 6,042,562 | A | 3/2000 | Amor |
| 6,056,717 | A | 5/2000 | Finch et al. |
| 6,077,756 | A | 6/2000 | Lin et al. |
| 6,086,555 | A | 7/2000 | Eliasen et al. |
| 6,090,066 | A | 7/2000 | Schnell |
| 6,099,508 | A | 8/2000 | Bousquet |
| 6,102,884 | A | 8/2000 | Squitieri |
| 6,113,572 | A | 9/2000 | Gailey et al. |
| 6,120,492 | A | 9/2000 | Finch et al. |
| 6,132,415 | A | 10/2000 | Finch et al. |
| 6,152,909 | A | 11/2000 | Bagaoisan et al. |
| 6,161,033 | A | 12/2000 | Kuhn |
| 6,171,198 | B1 | 1/2001 | Troncoso et al. |
| 6,171,298 | B1 | 1/2001 | Matsuura et al. |
| 6,186,982 | B1 | 2/2001 | Gross et al. |
| 6,190,352 | B1 | 2/2001 | Haarala et al. |
| 6,193,684 | B1 | 2/2001 | Burbank et al. |
| 6,198,807 | B1 | 3/2001 | DeSena |
| 6,200,338 | B1 | 3/2001 | Solomon et al. |
| 6,203,570 | B1 | 3/2001 | Baeke |
| 6,210,366 | B1 | 4/2001 | Sanfilippo, II |
| 6,213,973 | B1 | 4/2001 | Eliasen et al. |
| 6,228,088 | B1 | 5/2001 | Miller et al. |
| 6,251,059 | B1 | 6/2001 | Apple et al. |
| D445,175 | S | 7/2001 | Bertheas |
| 6,261,259 | B1 | 7/2001 | Bell |
| 6,269,148 | B1 | 7/2001 | Jessop et al. |
| 6,272,370 | B1 | 8/2001 | Gillies et al. |
| 6,287,293 | B1 | 9/2001 | Jones et al. |
| 6,290,677 | B1 | 9/2001 | Arai et al. |
| 6,305,413 | B1 | 10/2001 | Fischer et al. |
| 6,306,124 | B1 | 10/2001 | Jones et al. |
| D450,115 | S | 11/2001 | Bertheas |
| 6,315,762 | B1 | 11/2001 | Recinella et al. |
| 6,332,874 | B1 | 12/2001 | Eliasen et al. |
| 6,351,513 | B1 | 2/2002 | Bani-Hashemi et al. |
| 6,355,021 | B1 | 3/2002 | Nielsen et al. |
| 6,356,782 | B1 | 3/2002 | Sirimanne et al. |
| 6,361,557 | B1 | 3/2002 | Gittings et al. |
| 6,398,764 | B1 | 6/2002 | Finch, Jr. et al. |
| 6,419,680 | B1 | 7/2002 | Cosman et al. |
| 6,447,501 | B1 | 9/2002 | Solar et al. |
| 6,450,937 | B1 | 9/2002 | Mercereau et al. |
| 6,459,772 | B1 | 10/2002 | Wiedenhoefer et al. |
| 6,471,674 | B1 | 10/2002 | Emig et al. |
| 6,473,638 | B2 | 10/2002 | Ferek-Petric |
| 6,475,516 | B2 | 11/2002 | DiCosmo et al. |
| 6,478,783 | B1 | 11/2002 | Moorehead |
| 6,482,217 | B1 | 11/2002 | Pintor et al. |
| 6,494,867 | B1 | 12/2002 | Elver et al. |
| 6,497,062 | B1 | 12/2002 | Koopman et al. |
| 6,500,155 | B2 | 12/2002 | Sasso |
| 6,503,228 | B1 | 1/2003 | Li et al. |
| 6,527,754 | B1 | 3/2003 | Tallarida et al. |
| 6,537,255 | B1 | 3/2003 | Raines |
| RE38,074 | E | 4/2003 | Recinella et al. |
| 6,562,023 | B1 | 5/2003 | Marrs et al. |
| 6,572,583 | B1 | 6/2003 | Olsen et al. |
| 6,582,418 | B1 | 6/2003 | Verbeek et al. |
| 6,592,544 | B1 | 7/2003 | Mooney et al. |
| 6,592,571 | B1 | 7/2003 | Verbeek et al. |
| 6,610,031 | B1 | 8/2003 | Chin |
| 6,613,002 | B1 | 9/2003 | Clark et al. |
| 6,613,662 | B2 | 9/2003 | Wark et al. |
| 6,626,936 | B2 | 9/2003 | Stinson |
| D480,942 | S | 10/2003 | Ishida et al. |
| 6,629,950 | B1 | 10/2003 | Levin |
| 6,632,217 | B2 | 10/2003 | Harper et al. |
| 6,638,242 | B2 | 10/2003 | Wilson et al. |
| 6,652,486 | B2 | 11/2003 | Bialecki et al. |
| 6,652,503 | B1 | 11/2003 | Bradley |
| 6,663,646 | B1 | 12/2003 | Shah |
| 6,676,633 | B2 | 1/2004 | Smith et al. |
| 6,697,664 | B2 | 2/2004 | Kienzle, III et al. |

(56) References Cited

U.S. PATENT DOCUMENTS 6,699,219 B2 3/2004 Emig et al.
6,705,316 B2 3/2004 Blythe et al.
6,719,721 B1 4/2004 Okazaki et al.
6,719,739 B2 4/2004 Verbeek et al.
6,726,063 B2 4/2004 Stull et al.
6,726,678 B1 4/2004 Nelson et al.
6,738,531 B1 5/2004 Funahashi
6,755,842 B2 6/2004 Kanner et al.
6,758,841 B2 7/2004 Haarala et al.
6,767,356 B2 7/2004 Kanner et al.
6,784,783 B2 8/2004 Scoggin et al.
6,808,738 B2 10/2004 DiTizio et al.
D498,894 S 11/2004 Gould
6,826,257 B2 11/2004 Sayre et al.
6,827,709 B2 12/2004 Fujii
6,852,106 B2 2/2005 Watson et al.
6,856,055 B2 2/2005 Michaels et al.
6,878,136 B2 4/2005 Fleury et al.
6,878,137 B2 4/2005 Benchetrit
6,929,631 B1 8/2005 Brugger et al.
6,949,084 B2 9/2005 Marggi et al.
6,953,453 B2 10/2005 Recinella et al.
6,962,577 B2 11/2005 Tallarida et al.
6,962,580 B2 11/2005 Adams et al.
6,994,315 B2 2/2006 Ryan et al.
6,997,914 B2 2/2006 Smith et al.
7,008,377 B2 3/2006 Beane et al.
7,008,412 B2 3/2006 Maginot
7,016,456 B2 3/2006 Basu et al.
7,018,361 B2 3/2006 Gillespie, Jr. et al.
D518,573 S 4/2006 French
7,033,335 B2 4/2006 Haarala et al.
7,033,339 B1 4/2006 Lynn
7,044,942 B2 5/2006 Jolly et al.
7,056,316 B1 6/2006 Burbank et al.
7,070,591 B2 7/2006 Adams et al.
7,072,704 B2 7/2006 Bucholz
7,074,232 B2 7/2006 Kanner et al.
7,076,305 B2 7/2006 Imran et al.
7,083,593 B2 8/2006 Stultz
7,108,686 B2 9/2006 Burke et al.
7,123,690 B1 10/2006 Brown et al.
7,124,570 B2 10/2006 Blatter et al.
7,127,040 B2 10/2006 Sayre et al.
7,131,962 B1 11/2006 Stabrook et al.
7,140,769 B2 11/2006 Kay
7,186,236 B2 3/2007 Gibson et al.
7,191,011 B2 3/2007 Cantlon
7,198,631 B2 4/2007 Kanner et al.
7,214,207 B2 5/2007 Lynch et al.
7,214,215 B2 5/2007 Heinzerling et al.
7,223,257 B2 5/2007 Shubayev et al.
7,229,417 B2 6/2007 Foerster et al.
7,232,429 B2 6/2007 Moreci
7,235,067 B2 6/2007 Morris et al.
D546,440 S 7/2007 Burnside
7,242,982 B2 7/2007 Singhal et al.
7,248,668 B2 7/2007 Galkin
7,252,469 B2 8/2007 Zaluzec et al.
7,252,649 B2 8/2007 Sherry
7,261,705 B2 8/2007 Edoga et al.
D550,355 S 9/2007 Racz et al.
D554,253 S 10/2007 Kornerup
7,275,682 B2 10/2007 Excoffier et al.
7,276,075 B1 10/2007 Callas et al.
D556,153 S 11/2007 Burnside
7,306,579 B2 12/2007 Fujii
7,311,702 B2 12/2007 Tallarida et al.
7,318,816 B2 1/2008 Bobroff et al.
7,318,818 B2 1/2008 Yashiro et al.
7,322,953 B2 1/2008 Redinger
D562,442 S 2/2008 Blateri
D562,443 S 2/2008 Zinn et al.
7,331,130 B2 2/2008 Schweikert
7,331,948 B2 2/2008 Skarda
7,333,013 B2 2/2008 Berger
D564,449 S 3/2008 Dewberry
7,347,838 B2 3/2008 Kulli
7,347,843 B2 3/2008 Adams et al.
7,351,233 B2 4/2008 Parks
7,377,915 B2 5/2008 Rasmussen et al.
D574,950 S 8/2008 Zawacki et al.
7,413,564 B2 8/2008 Morris et al.
D578,203 S 10/2008 Bizup
7,445,614 B2 11/2008 Bunodiere et al.
D582,032 S 12/2008 Bizup et al.
7,465,847 B2 12/2008 Fabian
7,485,148 B2 2/2009 Wozencroft et al.
7,497,850 B2 3/2009 Halili
D590,499 S 4/2009 Chesnin
7,552,853 B2 6/2009 Mas et al.
7,553,298 B2 6/2009 Hunt et al.
D595,892 S 7/2009 Smith et al.
7,563,025 B2 7/2009 Kay
7,618,411 B2 11/2009 Appling
7,628,776 B2 12/2009 Gibson et al.
7,658,196 B2 2/2010 Ferreri et al.
D612,479 S 3/2010 Zawacki et al.
D613,394 S 4/2010 Linden
7,713,251 B2 5/2010 Tallarida et al.
7,722,580 B2 5/2010 Dicarlo et al.
D619,242 S 7/2010 Zinn et al.
7,766,880 B1 8/2010 Spinoza
7,785,302 B2 8/2010 Powers
7,803,143 B2 9/2010 Tallarida et al.
7,806,888 B2 10/2010 Frassica
7,811,266 B2 10/2010 Eliasen
D629,503 S 12/2010 Caffey et al.
7,846,139 B2 12/2010 Zinn et al.
7,850,660 B2 12/2010 Uth et al.
7,862,546 B2 1/2011 Conlon et al.
D634,840 S 3/2011 Lombardi, III et al.
7,909,804 B2 3/2011 Stats
7,931,619 B2 4/2011 Diamond et al.
7,947,022 B2 5/2011 Amin et al.
7,959,615 B2 6/2011 Stats et al.
7,972,314 B2 7/2011 Bizup et al.
8,007,474 B2 8/2011 Uth et al.
8,021,324 B2 9/2011 Bizup et al.
8,025,639 B2 9/2011 Powers et al.
8,029,482 B2 10/2011 Maniar et al.
D650,475 S 12/2011 Smith et al.
8,075,536 B2 12/2011 Gray et al.
8,092,435 B2 1/2012 Beling et al.
8,147,455 B2 4/2012 Butts et al.
8,172,894 B2 5/2012 Schmid et al.
8,172,896 B2 5/2012 McNamara et al.
8,177,762 B2 5/2012 Beasley et al.
8,182,453 B2 5/2012 Eliasen
8,197,454 B2 6/2012 Mann et al.
8,202,259 B2 6/2012 Evans et al.
8,257,325 B2 9/2012 Schweikert et al.
D676,955 S 2/2013 Orome
8,366,687 B2 2/2013 Girard et al.
8,377,034 B2 2/2013 Tallarida et al.
8,382,723 B2 2/2013 Powers et al.
8,382,724 B2 2/2013 Maniar et al.
8,409,153 B2 4/2013 Tallarida et al.
8,475,417 B2 7/2013 Powers et al.
8,545,460 B2 10/2013 Beasley et al.
8,585,660 B2 11/2013 Murphy
8,585,663 B2 11/2013 Powers et al.
8,603,052 B2 12/2013 Powers et al.
8,608,712 B2 * 12/2013 Bizup ............... A61M 39/0208 604/288.02
8,608,713 B2 12/2013 Beasley et al.
8,641,676 B2 2/2014 Butts et al.
8,641,688 B2 2/2014 Powers et al.
8,805,478 B2 8/2014 Powers et al.
8,852,160 B2 10/2014 Schweikert et al.
8,932,271 B2 * 1/2015 Hamatake ......... A61M 39/0247 604/288.01
8,939,947 B2 1/2015 Maniar et al.
8,998,860 B2 4/2015 Sheetz et al.

(56) References Cited

U.S. PATENT DOCUMENTS 9,079,004 B2 7/2015 Wiley et al.
9,248,268 B2 2/2016 Wiley et al.
9,265,912 B2 2/2016 Draper et al.
9,295,733 B2 3/2016 Trieu
9,421,352 B2 8/2016 Butts et al.
9,474,888 B2 10/2016 Wiley et al.
9,579,496 B2 2/2017 Evans et al.
9,603,992 B2 3/2017 Powers
9,603,993 B2 3/2017 Powers
9,642,986 B2 5/2017 Beasley
9,682,186 B2 6/2017 Powers et al.
9,717,895 B2 8/2017 Wiley et al.
9,937,337 B2 4/2018 Powers et al.
10,016,585 B2 7/2018 Powers et al.
10,052,470 B2 8/2018 Powers et al.
10,052,471 B2 * 8/2018 Hamatake ......... A61M 39/0208
10,086,186 B2 10/2018 Evans et al.
10,092,725 B2 10/2018 Beasley
10,155,101 B2 12/2018 Wiley et al.
10,179,230 B2 1/2019 Powers et al.
10,183,157 B2 1/2019 Powers et al.
10,238,850 B2 3/2019 Maniar et al.
10,265,512 B2 4/2019 Wiley et al.
10,307,581 B2 6/2019 Tibdon et al.
10,556,090 B2 2/2020 Beasley
10,625,065 B2 4/2020 Powers et al.
10,661,068 B2 5/2020 Powers et al.
10,675,401 B2 6/2020 Powers et al.
10,773,066 B2 9/2020 Hamatake et al.
10,857,340 B2 12/2020 Barron et al.
10,905,868 B2 2/2021 Maniar et al.
2001/0016699 A1 8/2001 Burbank et al.
2001/0016717 A1 8/2001 Haarala et al.
2001/0047165 A1 11/2001 Makower et al.
2001/0051766 A1 12/2001 Gazdzinski
2001/0053889 A1 12/2001 Marggi et al.
2001/0056266 A1 12/2001 Tallarida et al.
2002/0013557 A1 1/2002 Sherry
2002/0052576 A1 5/2002 Massengale
2002/0055715 A1 5/2002 Young et al.
2002/0087098 A1 7/2002 Iwami et al.
2002/0095205 A1 7/2002 Edwin et al.
2002/0121530 A1 9/2002 Socier
2002/0138068 A1 9/2002 Watson et al.
2002/0169418 A1 11/2002 Menzi et al.
2002/0173769 A1 11/2002 Gray et al.
2002/0173772 A1 11/2002 Olsen
2002/0183846 A1 12/2002 Kuslich et al.
2002/0188282 A1 12/2002 Greenberg
2003/0028173 A1 2/2003 Forsberg
2003/0032918 A1 2/2003 Quinn
2003/0093029 A1 5/2003 McGuckin et al.
2003/0100887 A1 5/2003 Scott et al.
2003/0109856 A1 6/2003 Sherry
2003/0130627 A1 7/2003 Smith et al.
2003/0135388 A1 7/2003 Martucci et al.
2003/0139812 A1 7/2003 Garcia et al.
2003/0141477 A1 7/2003 Miller
2003/0181878 A1 9/2003 Tallarida et al.
2003/0191452 A1 10/2003 Meglin et al.
2003/0208184 A1 11/2003 Burke et al.
2003/0216694 A1 11/2003 Tollini
2003/0217659 A1 11/2003 Yamamoto et al.
2004/0002693 A1 1/2004 Bright et al.
2004/0006316 A1 1/2004 Patton
2004/0019266 A1 1/2004 Marciante et al.
2004/0020462 A1 2/2004 Sauler et al.
2004/0020492 A1 2/2004 Dubrul et al.
2004/0024361 A1 2/2004 Fago et al.
2004/0044306 A1 3/2004 Lynch et al.
2004/0054352 A1 3/2004 Adams et al.
2004/0056266 A1 3/2004 Suh et al.
2004/0064110 A1 4/2004 Forsell
2004/0073196 A1 4/2004 Adams et al.
2004/0078000 A1 4/2004 Borchard et al.
2004/0086568 A1 5/2004 Ditizio et al.
2004/0087877 A1 5/2004 Besz et al.
2004/0087885 A1 5/2004 Kawano et al.
2004/0106878 A1 6/2004 Skujins et al.
2004/0106891 A1 6/2004 Langan et al.
2004/0106942 A1 6/2004 Taylor et al.
2004/0116901 A1 6/2004 Appling
2004/0133173 A1 7/2004 Edoga et al.
2004/0156472 A1 8/2004 Galkin
2004/0157952 A1 8/2004 Soffiati et al.
2004/0158207 A1 8/2004 Hunn et al.
2004/0167543 A1 8/2004 Mazzocchi et al.
2004/0176743 A1 9/2004 Morris et al.
2004/0186444 A1 9/2004 Daly et al.
2004/0199129 A1 10/2004 DiMatteo
2004/0199220 A1 10/2004 Cantlon
2004/0204692 A1 10/2004 Eliasen
2004/0204759 A1 10/2004 Blom et al.
2004/0225254 A1 11/2004 Tanaka et al.
2004/0254536 A1 12/2004 Conlon et al.
2004/0254537 A1 12/2004 Conlon et al.
2005/0000844 A1 1/2005 Schweikert
2005/0010176 A1 1/2005 Dikeman et al.
2005/0010286 A1 1/2005 Vijay
2005/0027234 A1 2/2005 Waggoner et al.
2005/0027261 A1 2/2005 Weaver et al.
2005/0038390 A1 2/2005 Fago et al.
2005/0044759 A1 3/2005 Schweikert
2005/0049553 A1 3/2005 Triplett et al.
2005/0070875 A1 3/2005 Kulessa
2005/0075614 A1 4/2005 Bunodiere et al.
2005/0080401 A1 4/2005 Peavey
2005/0085778 A1 4/2005 Parks
2005/0086071 A1 4/2005 Fox et al.
2005/0113806 A1 5/2005 De Carvalho et al.
2005/0124980 A1 6/2005 Sanders
2005/0131352 A1 6/2005 Conlon et al.
2005/0148866 A1 7/2005 Gunderson
2005/0148869 A1 7/2005 Masuda
2005/0148956 A1 7/2005 Conlon et al.
2005/0148957 A1 7/2005 Girard et al.
2005/0152841 A1 7/2005 Sayre et al.
2005/0171502 A1 8/2005 Daly et al.
2005/0182857 A1 8/2005 Kong
2005/0209573 A1 9/2005 Brugger et al.
2005/0215874 A1 9/2005 Wang et al.
2005/0241203 A1 11/2005 Lizotte et al.
2005/0256451 A1 11/2005 Adams et al.
2005/0256500 A1 11/2005 Fujii
2005/0277899 A1 12/2005 Conlon et al.
2005/0283119 A1 12/2005 Uth et al.
2006/0009788 A1 1/2006 Freeman et al.
2006/0017341 A1 1/2006 Hahn et al.
2006/0020256 A1 1/2006 Bell et al.
2006/0084929 A1 4/2006 Eliasen
2006/0089619 A1 4/2006 Ginggen
2006/0100592 A1 5/2006 Eliasen
2006/0116648 A1 6/2006 Hamatake
2006/0149189 A1 7/2006 Diamond et al.
2006/0171980 A1 8/2006 Helmus et al.
2006/0173410 A1 8/2006 Moberg et al.
2006/0173424 A1 8/2006 Conlon
2006/0178647 A1 8/2006 Stats
2006/0178648 A1 8/2006 Barron et al.
2006/0184141 A1 8/2006 Smith et al.
2006/0184142 A1 8/2006 Schon et al.
2006/0217359 A1 9/2006 Wentworth et al.
2006/0217659 A1 9/2006 Patton
2006/0217668 A1 9/2006 Schulze et al.
2006/0224128 A1 10/2006 Lurvey et al.
2006/0224129 A1 10/2006 Beasley et al.
2006/0224235 A1 10/2006 Rucker
2006/0241465 A1 10/2006 Huennekens et al.
2006/0247584 A1 11/2006 Sheetz et al.
2006/0253076 A1 11/2006 Butts et al.
2006/0264897 A1 11/2006 Lobl et al.
2006/0264898 A1 * 11/2006 Beasley ........... A61M 39/0247
428/36.9
2006/0271012 A1 11/2006 Canaud et al.

(56) References Cited

U.S. PATENT DOCUMENTS

2007/0003603 A1 1/2007 Karandikar et al.
2007/0004981 A1 1/2007 Boese et al.
2007/0007839 A1 1/2007 Lin
2007/0010881 A1 1/2007 Soye et al.
2007/0016162 A1 1/2007 Burbank et al.
2007/0049806 A1 3/2007 Adams et al.
2007/0049876 A1 3/2007 Patton
2007/0055290 A1 3/2007 Lober
2007/0073250 A1 3/2007 Schneiter
2007/0078391 A1 4/2007 Wortley et al.
2007/0078416 A1 4/2007 Eliasen
2007/0078432 A1 4/2007 Halseth et al.
2007/0083111 A1 4/2007 Hossack et al.
2007/0083156 A1 4/2007 Muto et al.
2007/0100302 A1 5/2007 Dicarlo et al.
2007/0112332 A1 5/2007 Harding et al.
2007/0120683 A1 5/2007 Flippen et al.
2007/0123831 A1 5/2007 Haindl et al.
2007/0135775 A1 6/2007 Edoga et al.
2007/0149920 A1 6/2007 Michels et al.
2007/0149921 A1 6/2007 Michels et al.
2007/0149947 A1 6/2007 Byrum
2007/0161958 A1 7/2007 Glenn
2007/0179456 A1 8/2007 Glenn
2007/0185462 A1 8/2007 Byrum
2007/0191773 A1 8/2007 Wojcik
2007/0207335 A1 9/2007 Karandikar et al.
2007/0208313 A1 9/2007 Conlon et al.
2007/0219510 A1 9/2007 Zinn et al.
2007/0233017 A1 10/2007 Zinn et al.
2007/0233018 A1 10/2007 Bizup et al.
2007/0233042 A1 10/2007 Moehle et al.
2007/0255226 A1 11/2007 Tennican et al.
2007/0255234 A1 11/2007 Haase et al.
2007/0270691 A1 11/2007 Bailey et al.
2007/0270770 A1 11/2007 Bizup
2007/0276344 A1 11/2007 Bizup et al.
2007/0276355 A1 11/2007 Nielsen et al.
2007/0282308 A1 12/2007 Bell
2007/0293800 A1 12/2007 McMaken et al.
2007/0299408 A1 12/2007 Alferness et al.
2008/0004642 A1 1/2008 Birk et al.
2008/0008654 A1 1/2008 Clarke et al.
2008/0015701 A1 1/2008 Garcia et al.
2008/0021392 A1 1/2008 Lurvey et al.
2008/0039820 A1 2/2008 Sommers et al.
2008/0048855 A1 2/2008 Berger
2008/0051731 A1 2/2008 Schweikert et al.
2008/0097406 A1 4/2008 Freed
2008/0108949 A1 5/2008 Beasley et al.
2008/0114308 A1 5/2008 di Palma et al.
2008/0133265 A1 6/2008 Silkaitis et al.
2008/0137923 A1 6/2008 Spahn
2008/0138387 A1 6/2008 Machiraju
2008/0171990 A1 7/2008 Zauner
2008/0208236 A1 8/2008 Hobbs et al.
2008/0281279 A1 11/2008 Hoendervoogt et al.
2008/0319398 A1 12/2008 Bizup
2008/0319399 A1 12/2008 Schweikert et al.
2008/0319405 A1 12/2008 Bizup
2009/0024024 A1 1/2009 Zinn
2009/0024098 A1 1/2009 Bizup et al.
2009/0035582 A1 2/2009 Nakatani et al.
2009/0118612 A1 5/2009 Grunwald et al.
2009/0118683 A1 5/2009 Hanson et al.
2009/0156928 A1 6/2009 Evans et al.
2009/0204072 A1 8/2009 Amin et al.
2009/0204074 A1 8/2009 Powers et al.
2009/0216216 A1 8/2009 Powers et al.
2009/0221974 A1 9/2009 Paganon
2009/0221976 A1 9/2009 Linden
2009/0227862 A1 9/2009 Smith et al.
2009/0227951 A1 9/2009 Powers et al.
2009/0227964 A1 9/2009 DiCarlo et al.
2009/0264901 A1 10/2009 Franklin et al.
2009/0264990 A1 10/2009 Bruszewski et al.
2009/0287050 A1 11/2009 Barthel
2009/0315684 A1 12/2009 Sacco et al.
2009/0322541 A1 12/2009 Jones et al.
2010/0010339 A1 1/2010 Smith et al.
2010/0042073 A1 2/2010 Oster et al.
2010/0063451 A1 3/2010 Gray et al.
2010/0069743 A1 3/2010 Sheetz et al.
2010/0106094 A1 4/2010 Fisher et al.
2010/0121283 A1 5/2010 Hamatake et al.
2010/0211026 A2 8/2010 Sheetz et al.
2010/0268165 A1 10/2010 Maniar et al.
2010/0268174 A1 10/2010 Steinke et al.
2010/0319700 A1 12/2010 Ng et al.
2011/0021922 A1 1/2011 Berard-Anderson et al.
2011/0054312 A1 3/2011 Bell et al.
2011/0092921 A1 4/2011 Beling et al.
2011/0098662 A1 4/2011 Zinn
2011/0098663 A1 4/2011 Zinn
2011/0118677 A1 5/2011 Wiley et al.
2011/0160673 A1 6/2011 Magalich et al.
2011/0183712 A1 7/2011 Eckstein et al.
2011/0213700 A1 9/2011 Sant'Anselmo
2011/0257609 A1 10/2011 Bizup et al.
2011/0264058 A1 10/2011 Linden et al.
2011/0271856 A1 11/2011 Fisher et al.
2011/0275930 A1 11/2011 Jho et al.
2011/0276015 A1 11/2011 Powers et al.
2011/0288502 A1 11/2011 Hibdon et al.
2011/0288503 A1 11/2011 Magalich et al.
2011/0311337 A1 12/2011 Amin et al.
2012/0018073 A1 1/2012 Maniar et al.
2012/0059250 A1 3/2012 Gray et al.
2012/0065622 A1 3/2012 Cornish et al.
2012/0078201 A1 3/2012 Mikami
2012/0078202 A1 3/2012 Beling et al.
2012/0191071 A1 7/2012 Butts et al.
2012/0226244 A1 9/2012 Beasley et al.
2012/0259296 A1 10/2012 Sheetz et al.
2012/0283560 A1 11/2012 Schweikert et al.
2012/0302969 A1 11/2012 Wiley et al.
2013/0165773 A1 6/2013 Powers et al.
2013/0172733 A1 7/2013 Maniar et al.
2013/0218103 A1 8/2013 Tallarida et al.
2013/0225990 A1 8/2013 Powers et al.
2013/0225991 A1 8/2013 Powers
2013/0245574 A1 9/2013 Powers et al.
2013/0338494 A1 12/2013 Wiley et al.
2014/0058275 A1 2/2014 Gregorich et al.
2014/0081219 A1 3/2014 Powers et al.
2014/0100534 A1 4/2014 Beasley et al.
2014/0107619 A1 4/2014 Butts et al.
2014/0330118 A1 11/2014 Powers et al.
2014/0350396 A1 11/2014 Powers et al.
2015/0008891 A1 1/2015 Li et al.
2015/0025478 A1 1/2015 Hibdon et al.
2015/0088091 A1 3/2015 Beasley et al.
2015/0112284 A1 4/2015 Hamatake et al.
2015/0290445 A1 10/2015 Powers et al.
2015/0290446 A1 10/2015 Wiley et al.
2017/0028185 A1 2/2017 Wiley et al.
2017/0157383 A1 6/2017 Evans et al.
2017/0232232 A1 8/2017 Beasley
2017/0246441 A1 8/2017 Powers et al.
2017/0319842 A1 11/2017 Wiley et al.
2018/0161565 A1 6/2018 Maniar et al.
2018/0311488 A1 11/2018 Powers et al.
2018/0353743 A1 12/2018 Hamatake et al.
2019/0038871 A1 2/2019 Beasley
2019/0060628 A1 2/2019 Evans et al.
2019/0111242 A1 4/2019 Wiley et al.
2019/0111243 A1 4/2019 Powers et al.
2019/0134373 A1 5/2019 Barron et al.
2019/0151641 A1 5/2019 Powers et al.
2019/0217073 A1 7/2019 Maniar et al.
2019/0252603 A1 8/2019 Wiley et al.
2019/0275311 A1 9/2019 Hibdon et al.
2020/0086105 A1 3/2020 Powers et al.
2020/0171278 A1 6/2020 Beasley

(56) References Cited

U.S. PATENT DOCUMENTS

| | | | |
|---|---|---|---|
| 2020/0230390 A1 | 7/2020 | Powers et al. | |
| 2021/0001104 A1 | 1/2021 | Evans et al. | |
| 2021/0077801 A1 | 3/2021 | Barron et al. | |
| 2021/0353926 A1 | 11/2021 | Wiley et al. | |

FOREIGN PATENT DOCUMENTS

| | | | |
|---|---|---|---|
| CA | 2692142 | A1 | 12/2008 |
| CA | 2693972 | A1 | 1/2009 |
| CA | 2757836 | C | 5/2017 |
| CN | 102421469 | A | 4/2012 |
| CN | 102612343 | A | 7/2012 |
| DE | 3618390 | C1 | 11/1987 |
| DE | 3720414 | A1 | 12/1987 |
| DE | 42 25 524 | A1 | 2/1994 |
| DE | 29512576 | U1 | 10/1995 |
| DE | 10346470 | A1 | 5/2005 |
| DE | 10 2009 018837 | A1 | 11/2010 |
| EP | 0128525 | A2 | 12/1984 |
| EP | 0134745 | A1 | 3/1985 |
| EP | 0343910 | A2 | 11/1989 |
| EP | 0366814 | A1 | 5/1990 |
| EP | 0239244 | | 9/1991 |
| EP | 0534782 | A1 | 3/1993 |
| EP | 0537892 | A1 | 4/1993 |
| EP | 0619101 | A1 | 10/1994 |
| EP | 1238682 | A2 | 9/2002 |
| EP | 1486229 | A1 | 12/2004 |
| EP | 1635899 | A2 | 3/2006 |
| EP | 1858565 | A1 | 11/2007 |
| EP | 1874393 | A1 | 1/2008 |
| EP | 1896117 | A2 | 3/2008 |
| EP | 1998842 | A2 | 12/2008 |
| EP | 2004272 | A2 | 12/2008 |
| EP | 2018209 | A2 | 1/2009 |
| EP | 2081634 | A1 | 7/2009 |
| EP | 2164559 | A1 | 3/2010 |
| EP | 2167182 | A1 | 3/2010 |
| EP | 2180915 | A1 | 5/2010 |
| EP | 2190517 | A1 | 6/2010 |
| EP | 2320974 | A1 | 5/2011 |
| EP | 2324879 | A2 | 5/2011 |
| EP | 2365838 | A1 | 9/2011 |
| EP | 2571563 | A1 | 3/2013 |
| EP | 2601999 | A1 | 6/2013 |
| EP | 2324879 | B1 | 1/2014 |
| EP | 2324878 | B1 | 8/2014 |
| EP | 2308547 | B1 | 9/2014 |
| EP | 2324880 | B1 | 12/2014 |
| EP | 1 965 854 | B1 | 9/2015 |
| EP | 2939703 | B1 | 3/2017 |
| EP | 2416828 | B1 | 2/2018 |
| FR | 1509165 | A | 1/1968 |
| FR | 2508008 | A1 | 12/1982 |
| FR | 2809315 | A1 | 11/2001 |
| GB | 178998 | A | 5/1922 |
| GB | 749942 | A | 6/1956 |
| GB | 966137 | A | 8/1964 |
| GB | 1559140 | A | 1/1980 |
| GB | 2102398 | A | 2/1983 |
| GB | 2191701 | A | 12/1987 |
| GB | 2350352 | A | 11/2000 |
| JP | 62155857 | A | 7/1987 |
| JP | 62281966 | A | 12/1987 |
| JP | 64-011562 | | 1/1989 |
| JP | H05-200107 | A | 8/1993 |
| JP | 6296633 | A | 10/1994 |
| JP | 2000-79168 | | 3/2000 |
| JP | 2000-079168 | A | 3/2000 |
| JP | 2002500076 | A | 1/2002 |
| JP | 2002-83281 | A | 3/2002 |
| JP | 2002-209910 | A | 7/2002 |
| JP | 2002-531149 | A | 9/2002 |
| JP | 2003-510136 | A | 3/2003 |
| JP | 2004-350937 | A | 12/2004 |
| JP | 2006-500087 | A | 1/2006 |
| JP | 2007-203070 | A | 8/2007 |
| JP | 2007-275548 | A | 10/2007 |
| JP | 2007-533368 | A | 11/2007 |
| JP | 3142990 | U | 7/2008 |
| JP | 2008-539025 | A | 11/2008 |
| JP | 2009-077965 | A | 4/2009 |
| JP | 2009-142520 | A | 7/2009 |
| JP | 2009-540932 | A | 11/2009 |
| JP | 2012-523284 | A | 10/2012 |
| JP | 2012-236040 | A | 12/2012 |
| JP | 2013-510652 | | 3/2013 |
| JP | 2013-526376 | A | 6/2013 |
| JP | 6018822 | B2 | 11/2016 |
| NO | 1993000945 | A1 | 1/1993 |
| WO | 8600213 | A1 | 1/1986 |
| WO | 1986000213 | A1 | 1/1986 |
| WO | 1989011309 | A1 | 11/1989 |
| WO | 9001958 | A1 | 3/1990 |
| WO | 1990001958 | A1 | 3/1990 |
| WO | 9206732 | A1 | 4/1992 |
| WO | 9305730 | A1 | 4/1993 |
| WO | 1993005730 | A1 | 4/1993 |
| WO | 1993008986 | A1 | 5/1993 |
| WO | 9323106 | A1 | 11/1993 |
| WO | 9405351 | A1 | 3/1994 |
| WO | 9516480 | A1 | 6/1995 |
| WO | 1995015194 | | 6/1995 |
| WO | 96-35477 | A1 | 11/1996 |
| WO | 9701370 | A1 | 1/1997 |
| WO | 1997001370 | A1 | 1/1997 |
| WO | 1997006845 | A1 | 2/1997 |
| WO | 9711726 | A1 | 4/1997 |
| WO | 9723255 | A1 | 7/1997 |
| WO | 9726931 | A1 | 7/1997 |
| WO | 1998017337 | A1 | 4/1998 |
| WO | 9818506 | A1 | 5/1998 |
| WO | 1998031417 | A2 | 7/1998 |
| WO | 99/10250 | A1 | 3/1999 |
| WO | 9912609 | A1 | 3/1999 |
| WO | 1999034859 | A1 | 7/1999 |
| WO | 9938553 | A1 | 8/1999 |
| WO | 9942166 | A1 | 8/1999 |
| WO | 0012171 | A1 | 3/2000 |
| WO | 0016844 | A1 | 3/2000 |
| WO | 00/20050 | A1 | 4/2000 |
| WO | 0033901 | A1 | 6/2000 |
| WO | 2000033901 | A1 | 6/2000 |
| WO | 0074565 | A1 | 12/2000 |
| WO | 0123023 | A1 | 4/2001 |
| WO | 2001023023 | A1 | 4/2001 |
| WO | 0160444 | A1 | 8/2001 |
| WO | 01/70304 | A1 | 9/2001 |
| WO | 2001095813 | | 12/2001 |
| WO | 0247549 | A1 | 6/2002 |
| WO | 2002047549 | A1 | 6/2002 |
| WO | 03/030962 | A2 | 4/2003 |
| WO | 03084832 | A1 | 10/2003 |
| WO | 03090509 | A2 | 11/2003 |
| WO | 2004004800 | A2 | 1/2004 |
| WO | 2004/012787 | A2 | 2/2004 |
| WO | 2004028611 | A1 | 4/2004 |
| WO | 2004071555 | A2 | 8/2004 |
| WO | 2004091434 | A2 | 10/2004 |
| WO | 2005037055 | A2 | 4/2005 |
| WO | 2005068009 | A1 | 7/2005 |
| WO | 2005072627 | A1 | 8/2005 |
| WO | 2005/089833 | A1 | 9/2005 |
| WO | 2006078915 | A2 | 7/2006 |
| WO | 2006096686 | A1 | 9/2006 |
| WO | 2006116438 | A2 | 11/2006 |
| WO | 2006116613 | A1 | 11/2006 |
| WO | 2006130133 | A1 | 12/2006 |
| WO | 2006134100 | A1 | 12/2006 |
| WO | 2007041471 | A2 | 4/2007 |
| WO | 2007079024 | A2 | 7/2007 |
| WO | 2007092210 | A1 | 8/2007 |
| WO | 2007094898 | A2 | 8/2007 |
| WO | 2007098771 | A2 | 9/2007 |

(56) References Cited

FOREIGN PATENT DOCUMENTS

| | | | |
|---|---|---|---|
| WO | 2007109164 | A2 | 9/2007 |
| WO | 2007126645 | A2 | 11/2007 |
| WO | 2007136538 | A2 | 11/2007 |
| WO | 2007/149546 | A2 | 12/2007 |
| WO | 2008008126 | A2 | 1/2008 |
| WO | 2008/024440 | A1 | 2/2008 |
| WO | 2008019236 | A1 | 2/2008 |
| WO | 2008/048461 | A2 | 4/2008 |
| WO | 2008048361 | A1 | 4/2008 |
| WO | 2008062173 | A1 | 5/2008 |
| WO | 2008063226 | A2 | 5/2008 |
| WO | 2008147760 | A1 | 12/2008 |
| WO | 2008157763 | A1 | 12/2008 |
| WO | 2009002839 | A1 | 12/2008 |
| WO | 2009012385 | A1 | 1/2009 |
| WO | 2009012395 | A1 | 1/2009 |
| WO | 2009035582 | A1 | 3/2009 |
| WO | 2009046439 | A2 | 4/2009 |
| WO | 2009046725 | A1 | 4/2009 |
| WO | 2009108669 | A1 | 9/2009 |
| WO | 2010030351 | A1 | 3/2010 |
| WO | 2010062633 | A1 | 6/2010 |
| WO | 2010118144 | A1 | 10/2010 |
| WO | 2011046604 | A2 | 4/2011 |
| WO | 2011053499 | A1 | 5/2011 |
| WO | 2011056619 | A1 | 5/2011 |
| WO | 2011062750 | A1 | 5/2011 |
| WO | 2011133950 | A1 | 10/2011 |
| WO | 2011146649 | A1 | 11/2011 |
| WO | 2013/165935 | A1 | 11/2013 |
| WO | 2014/031763 | A2 | 2/2014 |

OTHER PUBLICATIONS

U.S. Appl. No. 13/972,538, filed Aug. 21, 2013 Non-Final Office Action dated Feb. 3, 2016.

U.S. Appl. No. 14/083,250, filed Nov. 18, 2013 Non-Final Office Action dated Dec. 12, 2016.

U.S. Appl. No. 14/083,250, filed Nov. 18, 2013 Non-Final Office Action dated Apr. 1, 2016.

U.S. Appl. No. 14/104,354, filed Dec. 12, 2013 Final Office Action dated Jun. 15, 2018.

U.S. Appl. No. 14/104,354, filed Dec. 12, 2013 Final Office Action dated Jun. 21, 2016.

U.S. Appl. No. 14/104,354, filed Dec. 12, 2013 Final Office Action dated May 31, 2017.

U.S. Appl. No. 14/104,354, filed Dec. 12, 2013 Non-Final Office Action dated Feb. 26, 2016.

U.S. Appl. No. 14/104,354, filed Dec. 12, 2013 Non-Final Office Action dated Nov. 22, 2016.

U.S. Appl. No. 14/104,354, filed Dec. 12, 2013 Non-Final Office Action dated Sep. 4, 2019.

U.S. Appl. No. 14/104,354, filed Dec. 12, 2013 Notice of Allowance dated Feb. 13, 2020.

U.S. Appl. No. 14/141,263, filed Dec. 26, 2013 Notice of Allowance dated Apr. 20, 2016.

U.S. Appl. No. 14/171,364, filed Feb. 3, 2014 Decision on Appeal dated Feb. 23, 2018.

U.S. Appl. No. 14/171,364, filed Feb. 3, 2014 Examiner's Answer dated Jul. 29, 2016.

U.S. Appl. No. 14/171,364, filed Feb. 3, 2014 Final Office Action dated Jun. 25, 2015.

U.S. Appl. No. 14/171,364, filed Feb. 3, 2014 Non-Final Office Action dated Feb. 12, 2015.

U.S. Appl. No. 14/171,364, filed Feb. 3, 2014 Notice of Allowance dated Mar. 26, 2018.

U.S. Appl. No. 14/455,660, filed Aug. 8, 2014 Final Office Action dated May 19, 2017.

U.S. Appl. No. 14/455,660, filed Aug. 8, 2014 Final Office Action dated Nov. 27, 2015.

U.S. Appl. No. 14/455,660, filed Aug. 8, 2014 Non-Final Office Action dated Jul. 6, 2015.

U.S. Appl. No. 14/455,660, filed Aug. 8, 2014 Non-Final Office Action dated Mar. 18, 2015.

U.S. Appl. No. 14/455,660, filed Aug. 8, 2014 Non-Final Office Action dated Oct. 14, 2016.

U.S. Appl. No. 14/455,660, filed Aug. 8, 2014 Notice of Allowance dated Nov. 24, 2017.

U.S. Appl. No. 14/508,227, filed Oct. 7, 2014 Non-Final Office Action dated Jun. 15, 2018.

U.S. Appl. No. 14/508,227, filed Oct. 7, 2014 Notice of Allowance dated Feb. 4, 2019.

U.S. Appl. No. 14/508,227, filed Oct. 7, 2014 Restriction Requirement dated Apr. 20, 2018.

U.S. Appl. No. 14/587,862, filed Dec. 31, 2014 Advisory Action dated Aug. 18, 2017.

U.S. Appl. No. 14/587,862, filed Dec. 31, 2014 Final Office Action dated May 4, 2017.

U.S. Appl. No. 14/587,862, filed Dec. 31, 2014 Non-Final Office Action dated Nov. 3, 2016.

U.S. Appl. No. 14/587,862, filed Dec. 31, 2014 Non-Final Office Action dated Sep. 28, 2017.

U.S. Appl. No. 14/587,862, filed Dec. 31, 2014 Notice of Allowance dated Apr. 6, 2018.

U.S. Appl. No. 14/599,376, filed Jan. 16, 2015 Advisory Action dated Aug. 23, 2016.

U.S. Appl. No. 14/599,376, filed Jan. 16, 2015 Final Office Action dated Jun. 8, 2016.

U.S. Appl. No. 14/599,376, filed Jan. 16, 2015 Final Office Action dated May 16, 2017.

U.S. Appl. No. 14/599,376, filed Jan. 16, 2015 Non-Final Office Action dated Feb. 3, 2016.

U.S. Appl. No. 14/599,376, filed Jan. 16, 2015 Non-Final Office Action dated May 14, 2018.

U.S. Appl. No. 14/599,376, filed Jan. 16, 2015 Non-Final Office Action dated Nov. 7, 2016.

U.S. Appl. No. 14/599,376, filed Jan. 16, 2015 Notice of Allowance dated Nov. 6, 2018.

U.S. Appl. No. 14/748,917, filed Jun. 24, 2015 Notice of Allowance dated May 9, 2018.

U.S. Appl. No. 14/750,174, filed Jun. 25, 2015 Non-Final Office Action dated Nov. 1, 2016.

U.S. Appl. No. 14/750,174, filed Jun. 25, 2015 Notice of Allowance dated Mar. 10, 2017.

U.S. Appl. No. 15/043,450, filed Feb. 12, 2016 Final Office Action dated Mar. 29, 2018.

U.S. Appl. No. 15/043,450, filed Feb. 12, 2016 Non-Final Office Action dated Nov. 30, 2017.

U.S. Appl. No. 15/290,621, filed Oct. 11, 2016 Non-Final Office Action dated May 16, 2018.

U.S. Appl. No. 15/290,621, filed Oct. 11, 2016 Notice of Allowance dated Dec. 13, 2018.

U.S. Appl. No. 15/442,371, filed Feb. 24, 2017 Non-Final Office Action dated Mar. 20, 2018.

U.S. Appl. No. 15/585,030, filed May 2, 2017 Notice of Allowance dated May 29, 2018.

U.S. Appl. No. 15/594,288, filed May 12, 2017 Corrected Notice of Allowance dated May 6, 2020.

U.S. Appl. No. 15/594,288, filed May 12, 2017 Non-Final Office Action dated Aug. 21, 2019.

U.S. Appl. No. 15/594,288, filed May 12, 2017 Notice of Allowance dated Mar. 10, 2020.

U.S. Appl. No. 11/380,124, filed Apr. 25, 2006 Non-Final Office Action dated Apr. 26, 2010.

U.S. Appl. No. 11/380,124, filed Apr. 25, 2006 Non-Final Office Action dated Apr. 7, 2011.

U.S. Appl. No. 11/380,124, filed Apr. 25, 2006 Non-Final Office Action dated Jan. 16, 2009.

U.S. Appl. No. 11/380,124, filed Apr. 25, 2006 Non-Final Office Action dated Oct. 28, 2010.

U.S. Appl. No. 11/380,124, filed Apr. 25, 2006 Notice of Allowance dated Apr. 29, 2013.

(56) References Cited

OTHER PUBLICATIONS

U.S. Appl. No. 11/380,621, filed Apr. 27, 2006 Final Office Action dated Jan. 14, 2010.
U.S. Appl. No. 11/380,621, filed Apr. 27, 2006 Final Office Action dated Jan. 23, 2009.
U.S. Appl. No. 11/380,621, filed Apr. 27, 2006 Final Office Action dated Mar. 8, 2011.
U.S. Appl. No. 11/380,621, filed Apr. 27, 2006 Non-Final Office Action dated Jul. 1, 2009.
U.S. Appl. No. 11/380,621, filed Apr. 27, 2006 Non-Final Office Action dated Jun. 6, 2008.
U.S. Appl. No. 11/725,287, filed Mar. 19, 2007 Non-final Office Action dated Dec. 3, 2008.
U.S. Appl. No. 11/725,287, filed Mar. 19, 2007 Non-final Office Action dated Jun. 12, 2009.
U.S. Appl. No. 11/725,287, filed Mar. 19, 2007 Non-final Office Action dated Mar. 29, 2010.
U.S. Appl. No. 11/937,302, filed Nov. 8, 2007 Final Office Action dated Nov. 8, 2012.
U.S. Appl. No. 11/937,302, filed Nov. 8, 2007 Final Office Action dated Oct. 13, 2011.
U.S. Appl. No. 11/937,302, filed Nov. 8, 2007 Non-Final Office Action dated Jun. 18, 2012.
U.S. Appl. No. 11/937,302, filed Nov. 8, 2007 Final Office Action dated Feb. 11, 2011.
U.S. Appl. No. 11/937,302, filed Nov. 8, 2007 Non-Final Office Action dated Apr. 15, 2011.
U.S. Appl. No. 11/937,302, filed Nov. 8, 2007 Non-Final Office Action dated Sep. 13, 2010.
U.S. Appl. No. 12/023,280, filed Jan. 31, 2008 Final Office Action dated Mar. 9, 2010.
U.S. Appl. No. 12/023,280, filed Jan. 31, 2008 Non-Final Office Action dated Dec. 13, 2010.
U.S. Appl. No. 12/023,280, filed Jan. 31, 2008 Non-Final Office Action dated Jul. 23, 2009.
U.S. Appl. No. 12/023,280, filed Jan. 31, 2008 Non-Final Office Action dated Oct. 5, 2009.
U.S. Appl. No. 12/023,280, filed Jan. 31, 2008 Notice of Allowance dated Mar. 28, 2011.
U.S. Appl. No. 12/143,377, filed Jun. 20, 2008 Final Office Action dated Oct. 19, 2009.
U.S. Appl. No. 12/143,377, filed Jun. 20, 2008 Non-final Office Action dated Apr. 27, 2009.
U.S. Appl. No. 12/175,182, filed Jul. 17, 2008 Non-final Office Action dated Sep. 3, 2009.
U.S. Appl. No. 12/267,160, filed Nov. 7, 2008 Examiner's Answer dated Dec. 5, 2012.
U.S. Appl. No. 12/267,160, filed Nov. 7, 2008 Final Office Action dated Jun. 1, 2012.
U.S. Appl. No. 12/267,160, filed Nov. 7, 2008 Non-Final Office Action dated Nov. 1, 2011.
U.S. Appl. No. 12/419,854, filed Apr. 7, 2009 Advisory Action dated May 17, 2013.
U.S. Appl. No. 12/419,854, filed Apr. 7, 2009 Final Office Action dated Feb. 14, 2013.
U.S. Appl. No. 12/419,854, filed Apr. 7, 2009 Final Office Action dated Nov. 29, 2011.
U.S. Appl. No. 12/419,854, filed Apr. 7, 2009 Non-Final Office Action dated Aug. 5, 2011.
U.S. Appl. No. 12/419,854, filed Apr. 7, 2009 Non-Final Office Action dated Jun. 26, 2012.
U.S. Appl. No. 12/419,854, filed Apr. 7, 2009 Notice of Allowance dated Apr. 7, 2014.
U.S. Appl. No. 12/419,957, filed Apr. 7, 2009 Advisory Action dated Feb. 18, 2011.
U.S. Appl. No. 12/419,957, filed Apr. 7, 2009 Final Office Action dated Dec. 7, 2010.
U.S. Appl. No. 12/419,957, filed Apr. 7, 2009 Non-Final Office Action dated Feb. 18, 2010.
U.S. Appl. No. 12/419,957, filed Apr. 7, 2009 Non-Final Office Action dated Jul. 29, 2010.
U.S. Appl. No. 12/419,957, filed Apr. 7, 2009 Non-Final Office Action dated Jun. 30, 2009.
U.S. Appl. No. 12/419,957, filed Apr. 7, 2009 Notice of Allowance dated Mar. 7, 2011.
U.S. Appl. No. 12/420,007, filed Apr. 7, 2009 Final Office Action dated Mar. 22, 2013.
U.S. Appl. No. 12/420,007, filed Apr. 7, 2009 Non-Final Office Action dated Oct. 16, 2012.
U.S. Appl. No. 12/420,007, filed Apr. 7, 2009 Final Office Action dated Feb. 18, 2010.
U.S. Appl. No. 12/420,007, filed Apr. 7, 2009 Non-Final Office Action dated Jul. 14, 2009.
U.S. Appl. No. 12/420,028, filed Apr. 7, 2009 Non-Final Office Action dated Jan. 5, 2011.
U.S. Appl. No. 12/420,028, filed Apr. 7, 2009 Notice of Allowance dated Apr. 1, 2011.
U.S. Appl. No. 12/617,981, filed Nov. 13, 2009 Final Office Action dated Aug. 2, 2012.
U.S. Appl. No. 12/617,981, filed Nov. 13, 2009 Advisory Action dated Sep. 15, 2011.
U.S. Appl. No. 16/783,030, filed Feb. 5, 2020 Non-Final Office Action dated Apr. 27, 2022.
PCT/US2007/006776 filed Mar. 19, 2007 Written opinion, dated Dec. 18, 2007.
PCT/US2007/011015 dated May 7, 2007 Written Opinion dated Jun. 10, 2008.
PCT/US2007/011015 filed May 7, 2007 International Preliminary Report on Patentability dated Sep. 23, 2008.
PCT/US2007/011015 filed May 7, 2007 Search Report dated Jun. 10, 2008.
PCT/US2007/011456 filed May 11, 2007 Search Report dated Aug. 28, 2008.
PCT/US2007/011456 filed May 11, 2007 Written Opinion dated Aug. 28, 2008.
PCT/US2008/010520 dated Sep. 8, 2008 Search Report dated Feb. 24, 2009.
PCT/US2008/010520 filed Sep. 8, 2008 Written Opinion dated Feb. 24, 2009.
PCT/US2008/067679 filed Jun. 20, 2008 Search Report dated Sep. 30, 2008.
PCT/US2008/067679 filed Jun. 20, 2008 Written Opinion dated Sep. 30, 2008.
PCT/US2008/070330 filed Jul. 17, 2008 Search Report dated Dec. 1, 2008.
PCT/US2008/070330 filed Jul. 17, 2008 Written Opinion dated Dec. 1, 2008.
PCT/US2008/070345 filed Jul. 17, 2008 Search Report dated Dec. 1, 2008.
PCT/US2008/070345 filed Jul. 17, 2008 Written Opinion dated Dec. 1, 2008.
PCT/US2008/078976 filed Apr. 2, 2009 Search Report and Written Opinion dated Apr. 3, 2009.
PCT/US2009/035088 filed Feb. 25, 2009 International Search Report dated May 19, 2009.
PCT/US2009/035088 filed Feb. 25, 2009 Written Opinion dated May 19, 2009.
PCT/US2009/062854 filed Oct. 30, 2009 International Preliminary Report on Patentability dated May 5, 2011.
PCT/US2009/062854 filed Oct. 30, 2009 International Search Report dated Dec. 23, 2009.
PCT/US2009/062854 filed Oct. 30, 2009 Search Report dated Dec. 23, 2009.
PCT/US2009/062854 filed Oct. 30, 2009 Written Opinion dated Dec. 23, 2009.
PCT/US2010/030256 filed Apr. 7, 2010 Search Report dated Jun. 4, 2010.
PCT/US2010/030256 filed Apr. 7, 2010 Written Opinion dated Jun. 4, 2010.
PCT/US2010/054994 filed Nov. 1, 2010 Search Report dated Jan. 10, 2011.

(56) References Cited

OTHER PUBLICATIONS

PCT/US2010/054994 filed Nov. 1, 2010 Written Opinion dated Jan. 10, 2011.
PCT/US2011/037038 filed May 18, 2011 International Preliminary Report on Patentability dated Nov. 20, 2012.
PCT/US2011/037038 filed May 18, 2011 International Search Report and Written Opinion dated Aug. 30, 2011.
PCT/US2011/037038 filed May 18, 2011 Written Opinion and Search Report dated Aug. 30, 2011.
PCT/US2013/031035 filed Mar. 13, 2013 International Search Report and Written Opinion dated Jun. 3, 2013.
PCT/US2013/056019 filed Aug. 21, 2013 International Search Report and Written Opinion dated Feb. 28, 2014.
PCT/US99/28695 filed Dec. 3, 1999 International Preliminary Examination Report dated Apr. 21, 2001.
PCT/US99/28695 filed Dec. 3, 1999 Search Report dated Apr. 11, 2000.
PFM Medical, Xcela™ Power Injectable Port Directions for Use, 15 pages, © 2008.
Picture of HMP Vortex MP Vascular Access Port from Exhibit A11, Jun. 24, 2016.
Port-A-Cath Implantable Vascular Access Systems, brochure, (1996).
Port-A-Cath® P.A.S. Port® Systems by Deltec, Product Specifications, 1999.
Port-A-Cathr "Implantable Epidural, Aterial and Peritonial Access Systems" Internet Product Listing. <<http://web.archive.org/web/20001119035900/www.deltec.com/cPacspl.htm.>> last accessed Jun. 4, 2012.
Port-A-Cathr "Many Port-A-Cath® System Choices" Product Brochure. © 1996 SIMS Deltec, Inc.
Port-A-Cathr & Port-A-Cath® II Dual-lumen Implantable Venous Access Systems Product Specifications, 2005.
Port-A-Catho® II Implantable Access Systems Information Sheet, Sep. 2006.
Proper Care of the Vortex, Nov. 30, 2000.
Rappolt, Richard T., et al. "Radiopaque Codification and X-ray Identification of Ingested Drugs." Ingestive Radiology, May-Jun. 1966.
Request for Inter partes Reexamination of U.S. Pat. No. 7,785,302, filed Aug. 20, 2012.
Request for Inter partes Reexamination of U.S. Pat. No. 7,947,022, filed Aug. 20, 2012.
Request for Inter partes Reexamination of U.S. Pat. No. 7,959,615, filed Aug. 20, 2012.
RU 2014140544 filed Mar. 13, 2016 Office Action dated Jul. 20, 2017.
Salis et al., "Maximal flow rates possible during power injection through currently available PICCs: An in-vitro study," J Vasc Interv Radiol 2004; 15:275-281.
Sandstede, Joern, "Pediatric CT," available online at www.multislice-ct.com, MultiSLICE-CT.com, version 02, May 2, 2003.
C.R. Bard, Inc. "Hickman Subcutaneous Ports & Hickman /Broviac Catheters Brochure" Brochure, 1992.
CA 2,864,047 filed Aug. 6, 2014 Office Action dated Apr. 23, 2019.
CA 2757836 filed Oct. 5, 2011 Examiner's Report dated May 18, 2016.
Canaud et al. "Dialock: a new vascular access device for extracorporeal renal replacement therapy. Preliminary clinical results" Nephrol. Dial. Transplant 14: 692-698 (1999).
Canaud et al. "Dialock: Pilot Trial of a New Vascular Port Access Device for Hemodialysis" Seminars in Dialysis, vol. 12, No. 5, pp. 382-388 (Sep. 1999).
Canaud et al. "Dialock: Results of french multicentar trial" Nephrology, vol. 22, No. 8, pp. 391-397, (2001).
Cardiovascular and Interventional Radiology, Review Article, "Central Venous Access Catheters: Radiological Management of Complications," by U.K. Teichgraber, B. Gebauer, T. Benter, H.J. Wagner, published online Jul. 31, 2003.
Carlson et al., "Safety Considerations in the Power Injection of Contrast Media Via Central Venous Catheters during Computed Tomographic Examinations," Investigative Radiology, (May 1992) 27: 337-340.
Carlson, J. E. et al., "Safety Considerations in the Power Injection of Contrast Media Via Central Venous Catheters during Computed Tomographic Examinations" Investigative Radiology, vol. 27, p. 337-340, May 1992.
Center for Devices and Radiological Health, Guidance on 510(k) Submissions for Implanted Infusion Ports, Oct. 1990.
Clinical Plastic Products, "Oncology Jet Port Plus Catheter Systems" Instructions for Use, Oct. 12, 2011.
CN 200980153471.3 filed Jun. 30, 2011 Fifth Office Action dated Jun. 2, 2015.
CN 200980153471.3 filed Jun. 30, 2011 First Office Action dated Dec. 25, 2012.
CN 200980153471.3 filed Jun. 30, 2011 Fourth Office Action dated Nov. 15, 2014.
CN 200980153471.3 filed Jun. 30, 2011 Notice of Grant dated Nov. 5, 2015.
CN 200980153471.3 filed Jun. 30, 2011 Second Office Action dated Sep. 18, 2013.
CN 200980153471.3 filed Jun. 30, 2011 Third Office Action dated May 28, 2014.
CN 201080020088.3 filed Nov. 7, 2011 First Office Action dated Mar. 4, 2013.
CN 201080020088.3 filed Nov. 7, 2011 Second Office Action dated Nov. 21, 2013.
CN 201080051911.7 filed May 16, 2012 First Office Action dated Dec. 27, 2013.
CN 201080051911.7 filed May 16, 2012 Second Office Action dated Jul. 16, 2014.
CN 201080051911.7 filed May 16, 2012 Third Office Action dated Jan. 30, 2015.
CN 201380016157.7 filed Sep. 23, 2014 First office action dated May 16, 2016.
CN 201380016157.7 filed Sep. 23, 2014 Office Action dated Feb. 4, 2017.
CN 201380016157.7 filed Sep. 23, 2014 Office Action dated Jun. 1, 2017.
CN 201410216386.X filed May 21, 2014 First Office Action dated Nov. 2, 2015.
Cn 201410216386.X filed May 21, 2014 Office Action dated Jun. 24, 2016.
CN 201410216386.X filed May 21, 2014 Office Action dated Nov. 29, 2016.
CN 201410216386.X filed May 21, 2014 Search Report dated Nov. 2, 2015.
CN 201510645219.1 filed Nov. 1, 2015 Office Action dated Nov. 16, 2017.
CN 201610037718.7 filed Jan. 20, 2016 Office Action dated Jul. 2, 2018.
CN 201610037718.7 filed Jan. 20, 2016 Office Action dated Mar. 1, 2019.
CO 14.235.202 filed Oct. 23, 2014 Office Action dated Apr. 25, 2017.
CO 14.235.202 filed Oct. 23, 2014 Office Action dated Nov. 3, 2016.
CO 14.235.202 filed Oct. 23, 2014 Office Action dated Oct. 3, 2017.
Cook Vital-Port® Product Catalog (2000).
Costa, Nancy, "More Than Skin Deep: An Overview of Iodinated Contrast Media . . . " Journal for the Association for Vascular Access, vol. 8, No. 4, 2003.
Costa, Nancy, "Understanding Contrast Media." Journal of Infusion Nursing, vol. 27, No. 5, Sep./Oct. 2004.
Council Directive 93/42/EEC of Jun. 14, 1993 concerning medical devices (Jun. 14, 1993).
Coyle, Douglas et al, Power Injection of Contrast Media via Peripherally Inserted Central Catheters for CT, J Vasc Interv Radiol, pp. 809-814, vol. 15, 2004.
Declaration by Hank LaForce U.S. Pat. No. 7,785,302 (Ref D13 of Request for Trial for Invalidation dated May 22, 2017).
Defendant's Amended Answer to Plaintiffs' First Amended Complaint and Amended Counterclaims dated Sep. 17, 2017.

(56) References Cited

OTHER PUBLICATIONS

Deltec Port Systems (Feb. and Apr. 1996).
Department of Health and Human Services, C-Port 510(k) FDA Clearance, Jun. 5, 2003.
Department of Health and Human Services, PowerPort 510(k) FDA Clearance, Jan. 25, 2007.
Desmeules et al. "Venous Access for Chronic Hemodialysis: 'Undesirable Yet Unavoidable'", Artificial Organs 28(7):611-616 (2004).
Documents attached to P-U Celsite Port (new model first edition to sixth edition) (Ref D10 of Request for Trial for Invalidation dated May 22, 2017).
ECRI Institute, Healthcare Product Comparison System, Dec. 2007.
EP 06 751 411.7 filed Apr. 25, 2006 Office Action dated Sep. 2, 2008.
EP 06737222.7 filed Aug. 17, 2007 Office Action dated Jul. 27, 2016.
C.A. No. 15-218-SLR-SRF, Invalidity Contentions Exhibit A46 dated Jun. 24, 2016.
C.A. No. 15-218-SLR-SRF, Invalidity Contentions Exhibit A47 dated Jun. 24, 2016.
C.A. No. 15-218-SLR-SRF, Invalidity Contentions Exhibit A48 dated Jun. 24, 2016.
C.A. No. 15-218-SLR-SRF, Invalidity Contentions Exhibit A49 dated Jun. 24, 2016.
C.A. No. 15-218-SLR-SRF, Invalidity Contentions Exhibit A5 dated Jun. 24, 2016.
C.A. No. 15-218-SLR-SRF, Invalidity Contentions Exhibit A50 dated Jun. 24, 2016.
C.A. No. 15-218-SLR-SRF, Invalidity Contentions Exhibit A51 dated Jun. 24, 2016.
C.A. No. 15-218-SLR-SRF, Invalidity Contentions Exhibit A6 dated Jun. 24, 2016.
C.A. No. 15-218-SLR-SRF, Invalidity Contentions Exhibit A7 dated Jun. 24, 2016.
C.A. No. 15-218-SLR-SRF, Invalidity Contentions Exhibit A8 dated Jun. 24, 2016.
C.A. No. 15-218-SLR-SRF, Invalidity Contentions Exhibit A9 dated Jun. 24, 2016.
C.A. No. 15-218-SLR-SRF, Invalidity Contentions Exhibit B1 dated Jun. 24, 2016.
C.A. No. 15-218-SLR-SRF, Invalidity Contentions Exhibit B10 dated Jun. 24, 2016.
C.A. No. 15-218-SLR-SRF, Invalidity Contentions Exhibit B11 dated Jun. 24, 2016.
C.A. No. 15-218-SLR-SRF, Invalidity Contentions Exhibit B12 dated Jun. 24, 2016.
C.A. No. 15-218-SLR-SRF, Invalidity Contentions Exhibit B13 dated Jun. 24, 2016.
C.A. No. 15-218-SLR-SRF, Invalidity Contentions Exhibit B14 dated Jun. 24, 2016.
C.A. No. 15-218-SLR-SRF, Invalidity Contentions Exhibit B15 dated Jun. 24, 2016.
C.A. No. 15-218-SLR-SRF, Invalidity Contentions Exhibit B16 dated Jun. 24, 2016.
C.A. No. 15-218-SLR-SRF, Invalidity Contentions Exhibit B17 dated Jun. 24, 2016.
C.A. No. 15-218-SLR-SRF, Invalidity Contentions Exhibit B18 dated Jun. 24, 2016.
C.A. No. 15-218-SLR-SRF, Invalidity Contentions Exhibit B19 dated Jun. 24, 2016.
C.A. No. 15-218-SLR-SRF, Invalidity Contentions Exhibit B2 dated Jun. 24, 2016.
C.A. No. 15-218-SLR-SRF, Invalidity Contentions Exhibit B20 dated Jun. 24, 2016.
C.A. No. 15-218-SLR-SRF, Invalidity Contentions Exhibit B21 dated Jun. 24, 2016.
C.A. No. 15-218-SLR-SRF, Invalidity Contentions Exhibit B22 dated Jun. 24, 2016.
C.A. No. 15-218-SLR-SRF, Invalidity Contentions Exhibit B23 dated Jun. 24, 2016.
C.A. No. 15-218-SLR-SRF, Invalidity Contentions Exhibit B24 dated Jun. 24, 2016.
C.A. No. 15-218-SLR-SRF, Invalidity Contentions Exhibit B25 dated Jun. 24, 2016.
C.A. No. 15-218-SLR-SRF, Invalidity Contentions Exhibit B26 dated Jun. 24, 2016.
C.A. No. 15-218-SLR-SRF, Invalidity Contentions Exhibit B27 dated Jun. 24, 2016.
C.A. No. 15-218-SLR-SRF, Invalidity Contentions Exhibit B28 dated Jun. 24, 2016.
C.A. No. 15-218-SLR-SRF, Invalidity Contentions Exhibit B29 dated Jun. 24, 2016.
C.A. No. 15-218-SLR-SRF, Invalidity Contentions Exhibit B3 dated Jun. 24, 2016.
C.A. No. 15-218-SLR-SRF, Invalidity Contentions Exhibit B30 dated Jun. 24, 2016.
C.A. No. 15-218-SLR-SRF, Invalidity Contentions Exhibit B31 dated Jun. 24, 2016.
C.A. No. 15-218-SLR-SRF, Invalidity Contentions Exhibit B32 dated Jun. 24, 2016.
C.A. No. 15-218-SLR-SRF, Invalidity Contentions Exhibit B33 dated Jun. 24, 2016.
C.A. No. 15-218-SLR-SRF, Invalidity Contentions Exhibit B4 dated Jun. 24, 2016.
C.A. No. 15-218-SLR-SRF, Invalidity Contentions Exhibit B5 dated Jun. 24, 2016.
C.A. No. 15-218-SLR-SRF, Invalidity Contentions Exhibit B6 dated Jun. 24, 2016.
C.A. No. 15-218-SLR-SRF, Invalidity Contentions Exhibit B7 dated Jun. 24, 2016.
C.A. No. 15-218-SLR-SRF, Invalidity Contentions Exhibit B8 dated Jun. 24, 2016.
C.A. No. 15-218-SLR-SRF, Invalidity Contentions Exhibit B9 dated Jun. 24, 2016.
C.A. No. 15-218-SLR-SRF, Invalidity Contentions Exhibit C1 dated Jun. 24, 2016.
C.A. No. 15-218-SLR-SRF, Invalidity Contentions Exhibit C2 dated Jun. 24, 2016.
C.A. No. 15-218-SLR-SRF, Invalidity Contentions Exhibit C3 dated Jun. 24, 2016.
C.A. No. 15-218-SLR-SRF, Invalidity Contentions Exhibit C4 dated Jun. 24, 2016.
C.A. No. 15-218-SLR-SRF, Invalidity Contentions Exhibit C5 dated Jun. 24, 2016.
C.A. No. 15-218-SLR-SRF, Invalidity Contentions Exhibit C6 dated Jun. 24, 2016.
*C. R. Bard, Inc. and Bard Peripheral Vascular, Inc.*, v. *Medical Components, Inc*, "Memorandum Decision And Order Granting In Part Defendant's Partial Motion For Summary Judgment." Case 2:12-cv-00032-RJS-DAO; dated Jul. 21, 2021.
*C. R. Bard, Inc.* v. *Angiodynamics, Inc.*, Federal Circuit Decision 979 F.3d 1372, dated Nov. 10, 2020.
U.S. Appl. No. 17/026,104, filed Sep. 18, 2020 Non-Final Office Action dated Oct. 28, 2022.
U.S. Appl. No. 17/026,104, filed Sep. 18, 2020 Notice of Allowance dated Feb. 23, 2023.
U.S. Appl. No. 17/102,316, filed Nov. 23, 2020 Non-Final Office Action dated Jan. 26, 2023.
U.S. Appl. No. 17/164,560, filed Feb. 1, 2021 Non-Final Office Action dated Apr. 18, 2023.
U.S. Appl. No. 17/170,638, filed Feb. 8, 2021, Final Office Action dated Feb. 21, 2023.
U.S. Appl. No. 17/170,638, filed Feb. 8, 2021, Non-Final Office Action dated Aug. 5, 2022.
U.S. Appl. No. 17/170,638, filed Feb. 8, 2021, Notice of Allowance dated May 2, 2023.
"Japanese Journal of Cancer and Chemotherapy", 26, (13), 2055-2060, issued on Nov. 16, 1999. (Ref D18 of Request for Trial for Invalidation dated May 22, 2017).
"Rad Fan", 1, (3), 40-43, issued on Jul. 25, 2003 (Ref D17 of Request for Trial for Invalidation dated May 22, 2017).
"Safety Considerations in the Power Injection of Contrast Medium via a Totally Implantable Central Venous Access System" IVR

(56) References Cited

OTHER PUBLICATIONS

Interventional Radiology, 20, (1) 27-30, issued on Jan. 1, 2005. (Ref D09 of Request for Trial for Invalidation dated May 22, 2017).
Allergan, Inc. LAP-BAND® System Fact Sheet. © 2007.
Angiodynamics's Answer to Supplemental Complaint, Counterclaims Against Bard Peripheral Vascular, and Cross Claims/Third Party Complaint Against C.R. Bard. Public Version, dated Aug. 18, 2017.
Angiodynamics, Smart Port Guidelines for Health Care Providers, 2010.
Appendix B of Invalidity Contention Charts dated Nov. 28, 2017.
AU 2013235532 filed Aug. 6, 2014 Office Action dated Sep. 6, 2017.
B. Braun, Access Port Systems, Celsite® Product Information, 19 pages, Nov. 2005.
B. Braun, Easypump Product Page, accessed May 11, 2011.
B. Braun, Port Catheter Systems Product Page, accessed May 11, 2011.
Bard Access Systems Mar. 21, 1995 Product Release to Market form for "M.R.I. Port with 8 Fr. ChronoFlexÒ Catheter", "M.R.I. Port with 8Fr. ChronoFlex Catheter with Intro-Eze™", "M.R.I. Port with 8. Fr ChronoFlex Catheter and Peel Apart", "M.R.I. Port with 8Fr. ChronoFlex Catheter Demo Kit". Drawings included.
Bard Access Systems, BardPort and X-Port Implanted Ports Brochure, © 2007.
Bard Access Systems, BardPort, SlimPort and X-Port Instructions for Use, May 2003.
Bard Access Systems, BardPort, SlimPort, X-Port Instructions for Use, 24 pages, Oct. 2012.
Bard Access Systems, BardPort™ Implanted Ports Patient Information, Feb. 1993.
Bard Access Systems, Devices for Small Patients, 4 pages, Jul. 1992.
Bard Access Systems, Family of PICCs, 1 page, Mar. 10, 2006.
Bard Access Systems, M.R.I. Dual Port with Septum-Finder Ridge IFU, 2 pages, © 1993.
Bard Access Systems, Ports Brochure, © 2003.
Bard Access Systems, PowerPort and PowerLoc CT Guide, 11 pages, Dec. 2009.
Bard Access Systems, PowerPort and PowerLoc Product Brochure, 6 pages, © 2007.
Bard Access Systems, PowerPort CT Guide, 16 pages, Mar. 2007.
Bard Access Systems, PowerPort Guidelines for CT Technologists, 1 page, Feb. 2007.
Bard Access Systems, PowerPort Guidelines for CT Technologists, 1 page, Jul. 2006.
Bard Access Systems, PowerPort Guidelines for Nurses, 1 page, Feb. 2007.
Bard Access Systems, PowerPort Guidelines for Physicians, 1 page, Feb. 2007.
Bard Access Systems, PowerPort Implanted Port with Open-Ended Catheter Instructions for Use, 8 pages, Dec. 2006.
Bard Access Systems, PowerPort Information For the Patient, 5 pages, © 2006.
Bard Access Systems, PowerPort Prescription Pad, 1 page, © 2007.
Bard Access Systems, PowerPort Product Brochure, 8 pages, © 2009.
Bard Access Systems, PowerPort™ Implantable Port Product Information, © 2007.
Bard Access Systems, Titanium Dome Implantable Port, http://www.bardacess.com, last accessed Jan. 10, 2012.
Bard Access Systems, When in Doubt, SCOUT!, 1 page, © 2007.
Bard Healthcare Leaflet (2001).
Bardport, SlimPort, X-Port Instructions for Use, 2012.
Baxter Guidelines on Port Maintainence (Jun. 2003).
Baxter Healthport® Focus (Oct. 1999).
Baxter Healthport® Venous Systems (Oct. 2002).
Baxter Patient Information, Healthport® System (May 1999).
Baxter Therapy Systems, Baxter Healthport® Jan. 1999.
Beathard et al. "Initial clinical results with the LifeSite Hemodialysis Access System" Kidney International, vol. 58, pp. 2221-2227, (2000).
Biffi, R. et al. "Use of totally implantable central venous access ports for high-dose chemotherapy and peripheral blood stem cell transplantation: results of a monocentre series of 376 patients." Annals of Oncology 15:296-300, 2004.
Biffi, R., et al. "Best Choice of Central Venous Insertion Site for the Prevention of Catheter-Related Complications in Adult Patients Who Need Cancer Therapy: A Randomized Trial." Annals of Oncology, Jan. 29, 2009.
Biffi, Roberto, et al. "A Randomized, Prospective Trial of Central Venous Ports Connected to Standard Open-Ended or Groshong Catheters in Adult Oncology Patients." American Cancer Society, vol. 92, No. 5, pp. 1204-1212, Sep. 1, 2001.
BioEnterics Corporation, LAP-BAND® "Adjustable Gastric Banding System" Product Brochure Rev. G, Nov. 2000.
Biolink: Products—Dialock System (2002).
Biotronik, Stratos Cardiac Resynchronization Therapy Pacemakers Technical Manual, 179 pages, © 2008.
Boston Scientific, Xcela™ Power Injectable PICC Directions for Use, 12 pages, © 2007.
Braun Product Catalog (Aug. 2005).
EP 06737222.7 filed Aug. 17, 2007 Office Action dated Mar. 9, 2017.
EP 06751411 filed Apr. 25, 2006 Decision of the Technical Board of Appeal dated Jul. 24, 2013.
EP 06751411 filed Apr. 25, 2006 Decision Revoking the European Patent dated Aug. 1, 2012.
EP 06751411 filed Apr. 25, 2006 Office Action dated Aug. 10, 2009.
EP 06751411 filed Apr. 25, 2006 Opposition by Aesculap AG dated Oct. 6, 2011.
EP 06751411 filed Apr. 25, 2006 Opposition by Fresenius Kabi Deutschland GmbH dated Oct. 11, 2011.
EP 06751411 filed Apr. 25, 2006 Opposition by pfm medical ag dated Oct. 18, 2011.
EP 06751664.1 filed Apr. 27, 2006 First Examination Report dated Jul. 11, 2013.
EP 06751664.1 filed Apr. 27, 2006 Second Examination Report dated Dec. 17, 2014.
EP 06845998 filed Dec. 21, 2006 Office Action dated Mar. 10, 2011.
EP 06845998 filed Dec. 21, 2006 Supplementary Search Report dated Jul. 22, 2010.
EP 06845998.1 filed Dec. 21, 2006 Examination Report dated Feb. 6, 2014.
EP 06845998.1 filed Dec. 21, 2006 Examination Report dated May 13, 2013.
EP 06845998.1 filed Dec. 21, 2006 Examination Report dated Nov. 7, 2012.
EP 06845998.1 filed Dec. 21, 2006 Summons for Oral Proceedings dated Sep. 30, 2014.
EP 09824195.3 filed Apr. 13, 2011 Extended European Search Report dated Apr. 28, 2017.
EP 09824195.3 filed Apr. 13, 2011 Office Action dated Apr. 10, 2019.
EP 10 831 973.2 filed May 30, 2012 Extended European Search Report dated Jul. 4, 2014.
EP 10 831 973.2 filed May 30, 2012 Intent to Grant dated Feb. 12, 2018.
EP 10 831 973.2 filed May 30, 2012 Office Action dated Aug. 18, 2017.
EP 10183380.4 filed Apr. 25, 2006 European Search Report dated May 22, 2013.
EP 10183382.0 filed Apr. 25, 2006 European Search Report dated May 22, 2013.
EP 10183382.0 filed Apr. 25, 2006 Intent to Grant dated Mar. 7, 2014.
EP 10183394.5 filed Apr. 25, 2006 European Search Report dated May 22, 2013.
EP 10183394.5 filed Apr. 25, 2006 interlocutory decision dated Feb. 14, 2017.
EP 10183394.5 filed Apr. 25, 2006 Opponents Arguments in Support of the Appeal dated Jun. 30, 2017.

(56) References Cited

OTHER PUBLICATIONS

EP 10183394.5 filed Apr. 25, 2006 Opposition by Smiths Medical ASD, Inc. dated Apr. 25, 2014.
EP 10183394.5 filed Apr. 25, 2006 Opposition by Smiths Medical ASD, Inc. dated Dec. 2, 2015.
EP 10183394.5 filed Apr. 25, 2006 Opposition Grounds of Appeal dated May 17, 2017.
EP 10183394.5 filed Apr. 25, 2006 Response to Grounds of Appeal dated Nov. 3, 2017.
EP 10183398.6 filed Apr. 25, 2006 European Search Report dated May 22, 2013.
EP 10762377.9 filed Oct. 5, 2011 European Search Report dated Aug. 3, 2012.
EP 10762377.9 filed Oct. 5, 2011 Office Action dated Jul. 17, 2013.
EP 11784194.0 filed Nov. 29, 2012 Examination report dated Jul. 5, 2016.
EP 11784194.0 filed Nov. 29, 2012 extended European search report dated Feb. 21, 2014.
EP 13158343.7 filed Mar. 8, 2013 Examination Report dated Feb. 4, 2014.
EP 13158343.7 filed Mar. 8, 2013 Extended European Search Report dated May 14, 2013.
EP 13158343.7 filed Mar. 8, 2013 Summons to Attend Oral Proceedings dated Oct. 20, 2014.
EP 13764254.2 filed Sep. 10, 2014 Extended European Search Report dated Feb. 19, 2016.
EP 13764254.2 filed Sep. 10, 2014 Office Action dated Mar. 25, 2019.
EP 13764254.2 filed Sep. 10, 2014 Partial European Search Report dated Oct. 14, 2015.
EP 13830592.5 filed Feb. 24, 2015 Extended European Search Report dated Mar. 21, 2016.
EP 14198524.2 filed Dec. 17, 2014 Extended European Search Report dated Sep. 14, 2015.
EP 15180174 filed Aug. 7, 2015 European Search Report dated Jan. 4, 2016.
EP 15180174 filed Aug. 7, 2015 Office Action dated Jan. 13, 2017.
EP 16 193 913.7 filed Oct. 14, 2016 Extended European Search Report dated Apr. 13, 2017.
EP 16 193 913.7 filed Oct. 14, 2016 Office Action dated Feb. 13, 2018.
EP 18155508.7 filed Oct. 5, 2011 Partial European Search Report dated Nov. 6, 2018.
EP 99 964 086.5 filed Dec. 3, 1999 Office Action dated Dec. 15, 2005.
EP 99 964 086.5 filed Dec. 3, 1999 Office Action dated Mar. 1, 2005.
U.S. Appl. No. 15/660,513, filed Jul. 26, 2017 Restriction Requirement dated Mar. 15, 2018.
U.S. Appl. No. 15/881,616, filed Jan. 26, 2018 Final Office Action dated Aug. 6, 2018.
U.S. Appl. No. 15/881,616, filed Jan. 26, 2018 Non-Final Office Action dated Mar. 28, 2018.
U.S. Appl. No. 16/029,103, filed Jul. 6, 2018 Notice of Allowance dated Sep. 4, 2018.
U.S. Appl. No. 16/105,725, filed Aug. 20, 2018 Non-Final Office Action dated Sep. 18, 2019.
U.S. Appl. No. 16/105,725, filed Aug. 20, 2018 Notice of Allowance dated Dec. 26, 2019.
U.S. Appl. No. 16/105,774, filed Aug. 20, 2018 Corrected Notice of Allowability dated Aug. 19, 2020.
U.S. Appl. No. 16/105,774, filed Aug. 20, 2018 Final Office Action dated Apr. 17, 2020.
U.S. Appl. No. 16/105,774, filed Aug. 20, 2018 Non-Final Office Action dated Oct. 7, 2019.
U.S. Appl. No. 16/105,774, filed Aug. 20, 2018 Notice of Allowance dated Jun. 12, 2020.
U.S. Appl. No. 16/139,852, filed Sep. 24, 2018 Notice of Allowance dated Jul. 1, 2020.
U.S. Appl. No. 16/153,488, filed Oct. 5, 2018 Notice of Allowance dated Sep. 18, 2019.
U.S. Appl. No. 16/211,076, filed Dec. 5, 2018 Non-Final Office Action dated Aug. 7, 2020.
U.S. Appl. No. 16/241,775, filed Jan. 1, 2019 Notice of Allowance dated Oct. 1, 2020.
U.S. Appl. No. 16/252,005, filed Jan. 18, 2019 Non-Final Office Action dated May 22, 2020.
U.S. Appl. No. 16/362,546, filed Mar. 22, 2019 Notice of Allowance dated Oct. 14, 2020.
U.S. Appl. No. 16/691,340, filed Nov. 21, 2019 Non-Final Office Action dated Jan. 8, 2020.
U.S. Appl. No. 16/691,340, filed Nov. 21, 2019 Notice of Allowance dated Feb. 12, 2020.
U.S. Appl. No. 29/239,163, filed Sep. 27, 2005 entitled Injectable Power Port, listing Eddie K. Burnside as inventor.
U.S. Appl. No. 29/247,954, filed Jul. 21, 2006 entitled Injectable Power Port, listing Eddie K. Burnside as inventor.
U.S. Appl. No. 29/247,954, filed Jul. 21, 2006 Non-Final Office Action dated Apr. 6, 2007.
U.S. Appl. No. 29/247,954, filed Jul. 21, 2006 Notice of Allowability dated Jul. 30, 2007.
U.S. Appl. No. 29/284,454, filed Sep. 7, 2007 titled Implantable Port Device, listing John A. Zawacki and Annmarie Boswell as inventors, in which a Continued Prosecution Application was filed on Jan. 30, 2008.
U.S. Appl. No. 29/284,456, filed Sep. 7, 2007, titled Implantable Port Device, listing John A. Zawacki and Annemarie Boswell as inventors.
U.S. Appl. No. 29/382,235, filed Dec. 30, 2010 Non-Final Office Action dated Oct. 3, 2012.
U.S. Appl. No. 29/382,246, filed Dec. 30, 2010 Notice of Allowance dated Oct. 3, 2012.
U.S. Appl. No. 95/002,089, filed Aug. 20, 2012 Action Closing Prosecution dated Jun. 12, 2013.
U.S. Appl. No. 95/002,089, filed Aug. 20, 2012 Decision on Appeal in U.S. Pat. No. 7,785,302, dated Mar. 11, 2016.
U.S. Appl. No. 95/002,089, filed Aug. 20, 2012 Office Action In and Order Granting/Denying Request for Inter Partes Reexamination dated Nov. 7, 2012.
U.S. Appl. No. 95/002,090, filed Aug. 20, 2012 Action Closing Prosecution dated Jun. 12, 2013.
U.S. Appl. No. 95/002,090, filed Aug. 20, 2012 Decision on Appeal in U.S. Pat. No. 7,947,022, dated Mar. 29, 2016.
U.S. Appl. No. 95/002,090, filed Aug. 20, 2012 Office Action In and Order Granting/Denying Request for Inter Partes Reexamination dated Nov. 7, 2012.
U.S. Appl. No. 95/002,092, filed Aug. 20, 2012 Action Closing Prosecution dated Jun. 12, 2013.
U.S. Appl. No. 95/002,092, filed Aug. 20, 2012 Decision on Appeal in U.S. Pat. No. 7,959,615, dated Mar. 24, 2016.
U.S. Appl. No. 95/002,092, filed Aug. 20, 2012 Office Action In and Order Granting/Denying Request for Inter Partes Reexamination dated Nov. 13, 2012.
Vergara, et al., "Adverse Reactions to Contrast Medica in CT: Effects of Temperature and Ionic Property." Radiology, vol. 199, No. 2, May 1996.
Virot et al. "Long-term use of hemodialysis rooms LifeSite" Nephrologie vol. 24, No. 8, pp. 443-449 (2003).
Vogelzang, Robert L., "Power Injection Through Central Venous Catheters: Physiological and Hemodynamic Considerations." The McGaw Medical Center of Northwestern University, Feinberg School of Medicine. Jun. 23, 2004.
Wells, S. "Venous Access in Oncology and Haematology Patients: Part One." Nursing Standard, vol. 22, No. 52, pp. 39-46, Sep. 3, 2008.
Wikipedia, "Port Catheter", Dec. 15, 2011.
Williamson, et al., "Assessing the Adequacy of Peripherally Inserted Central Catheters for Power Injection of Intravenous Contrast Agents for CT." Journal of Computer Assisted Tomography, vol. 6, No. 6, pp. 932-937, 2001.
U.S. Appl. No. 16/211,076, filed Dec. 5, 2018 Notice of Allowance dated Nov. 12, 2020.
U.S. Appl. No. 16/362,546, filed Mar. 22, 2019 Corrected Notice of Allowance dated Nov. 27, 2020.

(56) References Cited

OTHER PUBLICATIONS

U.S. Appl. No. 16/389,732, filed Apr. 19, 2019 Notice of Allowance dated Mar. 23, 2021.
EP 99 964 086.5 filed Dec. 3, 1999 Office Action dated Mar. 30, 2005.
Ethanol Lock Technique for Prevention and Treatment of Central line-Associated Bloodstream Infections (Nebraska) Aug. 13, 2011, Accessed: Jun. 29, 2013 http://www.nebraskamed.com/app_files/pdf/careers/education-programs/asp/tnmc_etohlock_final.pdf.
Extravasation of Radiologic Contrast, PA-PSRS Patient Safety Advisory, vol. 1 No. 3, Sep. 2004.
Extreme Access™ Bard Access Systems, Inc. Product Brochure, 2003.
Fallscheer, et al., "Injury to the Upper Extremity Cuased by Extravasation of Contrast Medium: A True Emergency." Scandinavian Journal of Plastic and Reconstructive Surgery and Hand Surgery, vol. 41, pp. 26-32, 2007.
Fresenius Brochure on Intraport 1, Intraport II, and Bioport (Nov. 1998).
Gebauer, B. et al., "Contrast Media Power Injection Using Central Venous Port Catheters—Results of an In-Vitro Study," Experimental Radiology 2005: 177: 1417-1423.
Gebauer, B. et al., "Contrast Media Power Injection Using Central Venous Port Catheters—Results of an In-Vitro Study," Experimental Radiology 2005: 177: 1417-1423—Translation.
Herts, B. R., "Power Injection of Contrast Media Using Central Venous Catheters: Feasibility, Safety, and Efficacy" AJR 2001;176:447-453, Feb. 2001.
IMO 2002 Product Catalog, 2002.
Hou, Shaw-Min et al. "Comparisons of Outcomes and Survivals for Two Central Venous Access Port Systems." Journal of Surgical Oncology, 91:61-66, 2005.
Inamed Health, BioEnterics® LAP-BAND® "Adjustable Gastric Banding System" Product Brochure, Dec. 2003.
Johnson, Kathleen A., "Power Injectable Portal Systems." Journal of Radiology Nursing, vol. 28, Issue 1, Mar. 2009.
JP 2007-558331 filed Mar. 6, 2006 Office Action dated Aug. 20, 2013.
JP 2007-558331 filed Mar. 6, 2006 Office Action dated Jan. 22, 2013.
JP 2007-558331 filed Mar. 6, 2006 Office Action dated May 17, 2011.
JP 2008-509056 filed Apr. 25, 2006 Office Action dated Apr. 4, 2012.
JP 2008-509056 filed Apr. 25, 2006 Office Action dated Jun. 7, 2011.
JP 2012-156976 filed Jul. 12, 2012 Notice of Reasons for Refusal dated Apr. 8, 2014.
JP 2012-156976 filed Jul. 12, 2012 Notice of Reasons for Refusal dated Aug. 27, 2013.
JP 2012-156976 filed Jul. 12, 2012 Office Action dated Jun. 28, 2016.
JP 2012-156976 filed Jul. 12, 2012 Submission of Documents by Third Party dated May 14, 2013.
JP 2012-156976 filed Mar. 6, 2006, Office Action dated Mar. 29, 2016.
JP 2012-156976 filed Mar. 6, 2006, Third Party Submission dated Jul. 29, 2015.
JP 2012-504826 filed Oct. 6, 2011 First Office Action dated Mar. 4, 2014.
JP 2012-504826 filed Oct. 6, 2011 Second Office Action dated Nov. 17, 2014.
JP 2013-209156 filed Oct. 4, 2013 Non-Final Office Action dated Oct. 7, 2014.
JP 2013-511339 filed Nov. 16, 2012 First Office Action dated Feb. 19, 2015.
JP 2013-511339 filed Nov. 16, 2012 Office Action and Pre-Appeal Report dated Apr. 12, 2016.
JP 2013-511339 filed Nov. 16, 2012 Office Action dated Dec. 16, 2016.
JP 2013-511339 filed Nov. 16, 2012 Second Office Action dated Oct. 16, 2015.
JP 2015-501762 filed Sep. 16, 2014 First Office Action dated Oct. 5, 2016.
JP 2015-501762 filed Sep. 16, 2014 Office Action dated Feb. 1, 2017.
JP 2015-501762 filed Sep. 16, 2014 Office Action dated Jan. 16, 2018.
JP 2015-528624 filed Feb. 20, 2015 Office Action dated Apr. 25, 2018.
JP 2015-528624 filed Feb. 20, 2015 Office Action dated May 31, 2017.
JP 2016-026954 filed Feb. 16, 2016 Office Action dated Aug. 16, 2017.
JP 2016-026954 filed Feb. 16, 2016 Office Action dated Dec. 15, 2016.
JP 2018-077325 filed Apr. 13, 2018 Office Action dated Mar. 22, 2019.
JP 2018-077325 filed Apr. 13, 2018 Office Action dated Sep. 5, 2019.
JP 2018-077325 filed Apr. 13, 2018 Pre-Appeal Examination Report dated Mar. 6, 2020.
JP 6018822 filed Jul. 12, 2012 Request for Trial for Invalidation dated May 22, 2017.
JP2012-156976 filed Jul. 12, 2012 Amendment filed on Jul. 13, 2016 (Ref D06 of Request for Trial for Invalidation dated May 22, 2017).
JP2012-156976 filed Jul. 12, 2012 Amendment filed on Mar. 3, 2016 (Ref D04 of Request for Trial for Invalidation dated May 22, 2017).
JP2012-156976 filed Jul. 12, 2012 Amendment filed on Oct. 28, 2013 (Ref D03 of Request for Trial for Invalidation dated May 22, 2017).
JP2012-156976 filed Jul. 12, 2012 Office Action dated Aug. 20, 2013 (Ref D07 of Request for Trial for Invalidation dated May 22, 2017).
JP2012-156976 filed Jul. 12, 2012 Remarks filed on Mar. 3, 2016 (Ref D05 of Request for Trial for Invalidation dated May 22, 2017).
Kaste et al., "Safe use of power injectors with central and peripheral venous access devices for pediatric CT," Pediatr Radiol (1996) 26: 499-501.
KR 10-2011-7026328 filed Nov. 4, 2011 Notice of Last Preliminary Rejection dated Dec. 28, 2016.
KR 10-2011-7026328 filed Nov. 4, 2011 Notice of Preliminary Rejection dated Jun. 20, 2016.
KR 10-2017-7014546 filed May 29, 2017 Office Action dated Aug. 23, 2017.
KR 10-2017-7014546 filed May 29, 2017 Office Action dated Feb. 27, 2018.
L-Cath® for Ports, Luther Medical Products, Inc., Tustin, California, 2 pages, 1994.
LaMaitre Vascular "Port Implantations: using the OptiLock Implantable Port," product information, available at http://www.lemaitre.com/specs.pop.asp, last accessed Apr. 2003, 14 pages.
Lap-Band AP™ "System with Adjustable Gastric Banding system with OMNIFORM™ Design," Product Brochure, Jul. 2007, 16 pages.
Lap-Band® System Access Port Fill Guide I, "9.75/10.0 cm Lap-Band System vs. 11 cm Lap-Band System: For Product Manufactured Prior to Jul. 2001" BioEnterics Corporation. Rev. B. Aug. 15, 2001.
Leslie et al., "A New Simple Power Injector," Am J Roentgenol 128: 381-384, Mar. 1977.
Levin et al. "Initial results of a new access device for hemodialysis" Kidney International, vol. 54, pp. 1739-1745, (1998).
Levin et al. "New Access Device for Hemodialysis", ASAIO Journal (1998).
LifeSite: Instructions for Implantation & Use for the LifeSite Hemodialysis Access System, 2000.
MedComp "PortCT Technology", display at SIR Conference (Mar. 2006), Toronto, Canada.
Medcomp Dialysis and Vascular Access Products (MEDCOMP) Jun. 30, 2009, Accessed Jun. 29, 2013 http://www. medcompnet.com/products/flipbook/pdf/PN2114G_Medcomp_Catalog.pdf.

(56) References Cited

OTHER PUBLICATIONS

Medtronic IsoMed Technical Manual, Model 8472, (2008).
Medtronic IsoMed® Constant-Flow Infusion System: Clinical Reference Guide for Hepatic Arterial Infusion Therapy, Revised Sep. 2000.
MX/a/2011/004499 filed Apr. 28, 2011 First Office Action dated Jul. 25, 2013.
MX/a/2011/004499 filed Apr. 28, 2011 Forth Office Action dated Aug. 3, 2015.
MX/a/2011/004499 filed Apr. 28, 2011 Second Office Action dated May 25, 2014, translation dated Jul. 28, 2014.
MX/a/2011/004499 filed Apr. 28, 2011 Third Office Action dated Jan. 21, 2015.
MX/a/2011/010529 filed Oct. 5, 2011 Office Action dated Apr. 24, 2018.
MX/a/2011/010529 filed Oct. 5, 2011 Office Action dated Jan. 18, 2017.
MX/a/2011/010529 filed Oct. 5, 2011 Office Action dated May 19, 2016.
MX/a/2011/010529 filed Oct. 5, 2011 Office Action dated Oct. 2, 2017.
MX/a/2014/011280 filed Mar. 13, 2013, First Office Action dated May 29, 2015.
MX/a/2014/011280 filed Mar. 13, 2013, Second Office Action dated Oct. 27, 2015.
Navilyst Medical, Implantable Ports with PASV® Valve Technology, Product Overview,<<http://www.navilystmedical.com/Products/index.cfm/9>> last accessed Jun. 4, 2012.
Nebraska Medical Center, Ethanol Lock Technique for Prevention and Treatment of Central Line-Associated Bloodstream Infections, Jul. 2009.
Norfolk Medical Design Dossier/Technical File Vortex, Dec. 1997.
Nucleus Cochlear Implant Systems; User Manual for the ESPrit and ESPrit 22 speech processor and accessories, Issue 3, Apr. 2000.
Nucleus Cochlear Implant Systems; User Manual for the SPrint speech processor and accessories, Issue 4, Apr. 2002.
Oct. 22, 2009 Declaration of Kelly Christian, Director of Product Development at BARD Access Systems, Inc, in support of and depicting a product on the market by Quinton Company approximately ten years prior to Oct. 22, 2009, 1 page.
PCT/US 09/62854 filed Oct. 30, 2009 Written Opinion dated Dec. 23, 2009.
PCT/US06/49007 filed Dec. 21, 2006 Search Report and Written Opinion dated Oct. 1, 2007.
PCT/US2006/008022 filed Mar. 6, 2006 International Preliminary Report on Patentability dated Sep. 12, 2007.
PCT/US2006/008022 filed Mar. 6, 2006 Search Report dated Jul. 5, 2006.
PCT/US2006/008022 filed Mar. 6, 2006 Written Opinion dated Apr. 9, 2007.
PCT/US2006/008022 filed Mar. 6, 2006 Written Opinion dated Jul. 5, 2006.
PCT/US2006/015695 filed Apr. 25, 2006 Partial Search Report dated Sep. 29, 2006.
PCT/US2006/015695 filed Apr. 25, 2006 Search Report dated Jan. 11, 2007.
PCT/US2006/015695 filed Apr. 25, 2006 Written Opinion dated Jan. 11, 2007.
PCT/US2006/016056 filed Apr. 27, 2006 International Preliminary Report on Patentability dated Oct. 30, 2007.
PCT/US2006/016056 filed Apr. 27, 2006 Search Report dated Sep. 20, 2006.
PCT/US2006/016056 filed Apr. 27, 2006 Written Opinion dated Oct. 27, 2007.
PCT/US2006/016056 filed Apr. 27, 2006 Written Opinion dated Sep. 20, 2006.
PCT/US2006/049007 filed Dec. 21, 2006 International Preliminary Report on Patentability dated Jul. 1, 2008.
PCT/US2006/049007 filed Dec. 21, 2006 Written Opinion dated Oct. 1, 2007.
PCT/US2007/006776 filed Mar. 19, 2007 International Preliminary Report on Patentability dated Jan. 2, 2009.
PCT/US2007/006776 filed Mar. 19, 2007 International Search Report dated Dec. 18, 2007.
U.S. Appl. No. 12/617,981, filed Nov. 13, 2009 Final Office Action dated Jun. 21, 2011.
U.S. Appl. No. 12/617,981, filed Nov. 13, 2009 Non-Final Office Action dated Dec. 21, 2011.
U.S. Appl. No. 12/617,981, filed Nov. 13, 2009 Non-Final Office Action dated Jan. 5, 2011.
U.S. Appl. No. 12/796,133, filed Jun. 8, 2010 Non-Final Office Action dated Feb. 17, 2011.
U.S. Appl. No. 12/796,133, filed Jun. 8, 2010 Notice of Allowance dated Jun. 9, 2011.
U.S. Appl. No. 12/917,323, filed Nov. 1, 2010 Advisory Action dated Apr. 10, 2013.
U.S. Appl. No. 12/917,323, filed Nov. 1, 2010 Final Office Action dated Jan. 29, 2013.
U.S. Appl. No. 12/917,323, filed Nov. 1, 2010 Non-Final Office Action dated Aug. 15, 2012.
U.S. Appl. No. 12/917,323, filed Nov. 1, 2010 Non-Final Office Action dated Aug. 26, 2014.
U.S. Appl. No. 12/917,323, filed Nov. 1, 2010 Notice of Allowance dated Jan. 21, 2015.
U.S. Appl. No. 13/110,734, filed May 18, 2011 Non-Final Office Action dated Jul. 7, 2014.
U.S. Appl. No. 13/113,834, filed May 23, 2011 Final Office Action dated Nov. 23, 2012.
U.S. Appl. No. 13/113,834, filed May 23, 2011 Non-Final Office Action dated Jul. 17, 2012.
U.S. Appl. No. 13/159,230, filed Jun. 13, 2011 Notice of Allowance dated Aug. 1, 2012.
U.S. Appl. No. 13/250,909, filed Sep. 30, 2011 Notice of Allowance dated Aug. 6, 2012.
U.S. Appl. No. 13/438,586, filed Apr. 3, 2012 Advisory Action dated May 29, 2013.
U.S. Appl. No. 13/438,586, filed Apr. 3, 2012 Final Office Action dated Mar. 7, 2013.
U.S. Appl. No. 13/438,586, filed Apr. 3, 2012 Non-Final Office Action dated Sep. 19, 2012.
U.S. Appl. No. 13/438,586, filed Apr. 3, 2012 Notice of Allowance dated Sep. 16, 2013.
U.S. Appl. No. 13/471,219, filed May 14, 2012 Non-Final Office Action dated Jul. 10, 2013.
U.S. Appl. No. 13/524,712, filed Jun. 15, 2012 Advisory Action dated May 7, 2014.
U.S. Appl. No. 13/524,712, filed Jun. 15, 2012 Final Office Action dated Mar. 3, 2014.
U.S. Appl. No. 13/524,712, filed Jun. 15, 2012 Non-Final Office Action dated Aug. 21, 2014.
U.S. Appl. No. 13/524,712, filed Jun. 15, 2012 Non-Final Office Action dated Oct. 22, 2013.
U.S. Appl. No. 13/524,712, filed Jun. 15, 2012 Notice of Allowance dated Dec. 12, 2014.
U.S. Appl. No. 13/571,088, filed Aug. 9, 2012 Final Office Action dated Jul. 16, 2013.
U.S. Appl. No. 13/571,088, filed Aug. 9, 2012 Final Office Action dated Jul. 6, 2015.
U.S. Appl. No. 13/571,088, filed Aug. 9, 2012 Non-Final Office Action dated Feb. 27, 2013.
U.S. Appl. No. 13/571,088, filed Aug. 9, 2012 Non-Final Office Action dated Jan. 7, 2015.
U.S. Appl. No. 13/571,088, filed Aug. 9, 2012 Notice of Allowance dated Sep. 16, 2015.
U.S. Appl. No. 13/776,451, filed Feb. 25, 2013 Non-Final Office Action dated Jul. 24, 2013.
U.S. Appl. No. 13/776,517, filed Feb. 25, 2013 Final Office Action dated Jun. 30, 2014.
U.S. Appl. No. 13/776,517, filed Feb. 25, 2013 Non-Final Office Action dated Feb. 27, 2014.
U.S. Appl. No. 13/776,517, filed Feb. 25, 2013 Non-Final Office Action dated Nov. 15, 2013.

(56) References Cited

OTHER PUBLICATIONS

U.S. Appl. No. 13/776,517, filed Feb. 25, 2013 Notice of Allowance dated Sep. 23, 2014.
U.S. Appl. No. 13/801,893, filed Mar. 13, 2013 Notice of Allowance dated Sep. 24, 2015.
U.S. Appl. No. 13/853,942, filed Mar. 29, 2013 Non-Final Office Action dated Jul. 26, 2013.
U.S. Appl. No. 13/853,956, filed Mar. 29, 2013 Final Office Action dated Feb. 20, 2015.
U.S. Appl. No. 13/853,956, filed Mar. 29, 2013 Final Office Action dated Jan. 10, 2017.
U.S. Appl. No. 13/853,956, filed Mar. 29, 2013 Final Office Action dated Oct. 18, 2016.
U.S. Appl. No. 13/853,956, filed Mar. 29, 2013 Non-Final Office Action dated Dec. 3, 2013.
U.S. Appl. No. 13/853,956, filed Mar. 29, 2013 Non-Final Office Action dated Jun. 16, 2016.
U.S. Appl. No. 13/853,956, filed Mar. 29, 2013 Non-Final Office Action dated Sep. 15, 2014.
U.S. Appl. No. 13/853,961, filed Mar. 29, 2013 Final Office Action dated Feb. 20, 2015.
U.S. Appl. No. 13/853,961, filed Mar. 29, 2013 Final Office Action dated Jan. 9, 2017.
U.S. Appl. No. 13/853,961, filed Mar. 29, 2013 Non-Final Office Action dated Dec. 3, 2013.
U.S. Appl. No. 13/853,961, filed Mar. 29, 2013 Non-Final Office Action dated Jun. 15, 2016.
U.S. Appl. No. 13/853,961, filed Mar. 29, 2013 Non-Final Office Action dated Oct. 18, 2016.
Buerger et al "Implantation of a new device for haemodialysis" Nephrol. Dial. Transplant 15: 722-724 (2000).
*C. R. Bard, Inc. and Bard Peripheral Vascular, Inc*., v. *Angiodynamics, Inc*., C.A. No. 15-218-JFB-SRF, Angiodynamics's Answer To Supplemental Complaint, Counterclaims Against Bard Peripheral Vascular, And Crossclaims/Third Party Complaint Against C.R. Bard public version dated Aug. 25, 2017. [Redacted].
*C. R. Bard, Inc. and Bard Peripheral Vascular, Inc*., v. *Angiodynamics, Inc*., C.A. No. 15-218-SLR- Srf, Angiodynamics, Inc.'s Initial Invalidity Contentions dated Jun. 24, 2016.
*C. R. Bard, Inc. and Bard Peripheral Vascular, Inc*., v. *Angiodynamics, Inc*., C.A. No. 15-218-SLR-SRF, Defendant And Counterclaim-Plaintiff Angiodynamics's Identification Of Invalidity References dated Mar. 15, 2017.
*C. R. Bard, Inc. and Bard Peripheral Vascular, Inc*., v. *Angiodynamics, Inc*., C.A. No. 15-218-SLR-SRF, Expert Report Of Timothy Clark, MD, MD, FSIR Regarding Infringement Of The Patents-In-Suit dated Nov. 30, 2017. [Redacted].
*C. R. Bard, Inc. and Bard Peripheral Vascular, Inc*., v. *Angiodynamics, Inc*., C.A. No. 1:15-cv-00218-JFB-SRF, Opening Expert Report Of Robert L. Vogelzang, M.D. Regarding Invalidity Of U.S. Patent No. 8,475,417, U.S. Pat. No. 8,545,460 & U.S. Pat. No. 8,805,478 dated Sep. 1, 2017. [Redacted].
*C. R. Bard, Inc. and Bard Peripheral Vascular, Inc*., v. *Medical Components, Inc*., C.A. No. 2:17-cv-00754-TS, Defendant's Initial Noninfringement, Unenforceability, And Invalidity Contentions dated Nov. 28, 2017.
*C. R. Bard, Inc. and Bard Peripheral Vascular, Inc*., v. *Medical Components, Inc*., C.A. No. 2:17-cv-00754-TS, Defendant's Second Amended Answer To Plaintiffs' First Amended Complaint And Second Amended Counterclaims dated Nov. 7, 2017.
*C. R. Bard, Inc. and Bard Peripheral Vascular, Inc*., v. *Medical Components, Inc*., C.A. No. 2:17-cv-00754-TS, Plaintiffs' Motion To Dismiss Medcomp's Inequitable Conduct Counterclaims And To Strike Medcomp's Inequitable Conduct Affirmative Defenses dated Oct. 16, 2017.
*C. R. Bard, Inc*. v *Innovative Medical Devices, LLC*; Medical Components, Inc. "Petition For Inter Partes Review Of U.S. Pat. No. 8,852,160" dated Jul. 31, 2015.
C.A. No. 15-218-SLR-SRF, Invalidity Contentions Exhibit A1 dated Jun. 24, 2016.
C.A. No. 15-218-SLR-SRF, Invalidity Contentions Exhibit A10 dated Jun. 24, 2016.
C.A. No. 15-218-SLR-SRF, Invalidity Contentions Exhibit A11 dated Jun. 24, 2016.
C.A. No. 15-218-SLR-SRF, Invalidity Contentions Exhibit A12 dated Jun. 24, 2016.
C.A. No. 15-218-SLR-SRF, Invalidity Contentions Exhibit A13 dated Jun. 24, 2016.
C.A. No. 15-218-SLR-SRF, Invalidity Contentions Exhibit A14 dated Jun. 24, 2016.
C.A. No. 15-218-SLR-SRF, Invalidity Contentions Exhibit A15 dated Jun. 24, 2016.
C.A. No. 15-218-SLR-SRF, Invalidity Contentions Exhibit A16 dated Jun. 24, 2016.
C.A. No. 15-218-SLR-SRF, Invalidity Contentions Exhibit A17 dated Jun. 24, 2016.
C.A. No. 15-218-SLR-SRF, Invalidity Contentions Exhibit A18 dated Jun. 24, 2016.
C.A. No. 15-218-SLR-SRF, Invalidity Contentions Exhibit A19 dated Jun. 24, 2016.
C.A. No. 15-218-SLR-SRF, Invalidity Contentions Exhibit A2 dated Jun. 24, 2016.
C.A. No. 15-218-SLR-SRF, Invalidity Contentions Exhibit A20 dated Jun. 24, 2016.
C.A. No. 15-218-SLR-SRF, Invalidity Contentions Exhibit A21 dated Jun. 24, 2016.
C.A. No. 15-218-SLR-SRF, Invalidity Contentions Exhibit A22 dated Jun. 24, 2016.
C.A. No. 15-218-SLR-SRF, Invalidity Contentions Exhibit A23 dated Jun. 24, 2016.
C.A. No. 15-218-SLR-SRF, Invalidity Contentions Exhibit A24 dated Jun. 24, 2016.
C.A. No. 15-218-SLR-SRF, Invalidity Contentions Exhibit A25 dated Jun. 24, 2016.
C.A. No. 15-218-SLR-SRF, Invalidity Contentions Exhibit A26 dated Jun. 24, 2016.
C.A. No. 15-218-SLR-SRF, Invalidity Contentions Exhibit A27 dated Jun. 24, 2016.
C.A. No. 15-218-SLR-SRF, Invalidity Contentions Exhibit A28 dated Jun. 24, 2016.
C.A. No. 15-218-SLR-SRF, Invalidity Contentions Exhibit A29 dated Jun. 24, 2016.
C.A. No. 15-218-SLR-SRF, Invalidity Contentions Exhibit A3 dated Jun. 24, 2016.
C.A. No. 15-218-SLR-SRF, Invalidity Contentions Exhibit A30 dated Jun. 24, 2016.
C.A. No. 15-218-SLR-SRF, Invalidity Contentions Exhibit A31 dated Jun. 24, 2016.
C.A. No. 15-218-SLR-SRF, Invalidity Contentions Exhibit A32 dated Jun. 24, 2016.
C.A. No. 15-218-SLR-SRF, Invalidity Contentions Exhibit A33 dated Jun. 24, 2016.
C.A. No. 15-218-SLR-SRF, Invalidity Contentions Exhibit A34 dated Jun. 24, 2016.
C.A. No. 15-218-SLR-SRF, Invalidity Contentions Exhibit A35 dated Jun. 24, 2016.
C.A. No. 15-218-SLR-SRF, Invalidity Contentions Exhibit A36 dated Jun. 24, 2016.
C.A. No. 15-218-SLR-SRF, Invalidity Contentions Exhibit A37 dated Jun. 24, 2016.
C.A. No. 15-218-SLR-SRF, Invalidity Contentions Exhibit A38 dated Jun. 24, 2016.
C.A. No. 15-218-SLR-SRF, Invalidity Contentions Exhibit A39 dated Jun. 24, 2016.
C.A. No. 15-218-SLR-SRF, Invalidity Contentions Exhibit A4 dated Jun. 24, 2016.
C.A. No. 15-218-SLR-SRF, Invalidity Contentions Exhibit A40 dated Jun. 24, 2016.
C.A. No. 15-218-SLR-SRF, Invalidity Contentions Exhibit A41 dated Jun. 24, 2016.
C.A. No. 15-218-SLR-SRF, Invalidity Contentions Exhibit A42 dated Jun. 24, 2016.

(56) References Cited

OTHER PUBLICATIONS

C.A. No. 15-218-SLR-SRF, Invalidity Contentions Exhibit A43 dated Jun. 24, 2016.
C.A. No. 15-218-SLR-SRF, Invalidity Contentions Exhibit A44 dated Jun. 24, 2016.
C.A. No. 15-218-SLR-SRF, Invalidity Contentions Exhibit A45 dated Jun. 24, 2016.
Sanelli, et al., "Safety and Feasibility of Using a Central Venous Catheter for Rapid Contrast Injection Rates." American Journal of Radiology, vol. 183, pp. 1829-1834, Dec. 2004.
Shah, Tilak M., "Radiopaque Polymer Formulations for Medical Devices." Medical Device and Diagnostic Industry, Mar. 2000.
Smith Medical, Port-A-Cath® "Single-lumen Implantable Vascular Access Systems" Product Specifications, 2004.
Smith, Lisa Hartkoph, "Implanted Ports, Computed Tomography, Power Injectors, and Catheter Rupture." Clinical Journal of Oncology Nursing, vol. 12 , No. 5. Oct. 2008.
Smiths Medical, "Smiths Medical Launches Implantable Ports for Easy Viewing Under CT Scans" Press Release, Jan. 5, 2011.
Soloman, et al., "CIN Strategies: Anticipate, Manage, Prevent." Supplement to Imaging Economics, May 2007.
Statement of Prof. Dr. med. Karl R. Aigner, Oct. 11, 2011.
Steinbach, Barbara G. , Hardt, N. Sisson, Abbitt, Patricia L., Lanier, Linda, Caffee, H. Hollis, "Breast Implants, Common Complications, and Concurrent Breast Disease." RadioGraphics, vol. 13, No. 1, pp. 95-118, 1993.
Sullivan et al. "Radiopaque Markers on Mammary Implants." American Journal of Roentgenology 153(2):428, Aug. 1989.
Summers, "A New and Growing family of artificial implanted fluid-control devices" vol. XVI Trans. Amer. Soc. Artif. Int. Organs, 1970.
Takeuchi, Syuhei et al., "Safety Considerations in the Power Injection of Contrast Medium via a Totally Implantable Central Venous Access System," Japan Journal of Interventional Radiology vol. 20, No. 1, pp. 27-30, Jan. 2005.
Tilford, C. R., "Pressure and Vacuum Measurements"—Ch 2 of Physical Methods of Chemistry pp. 101-173, 1992.
Toray "P-U Celsite Port" brochure—Sep. 1999.
U.S. Department of Health and Human Services, FDA, "Labeling: Regulatory Requirements for Medical Devices" Aug. 1989.
U.S. Food and Drug Administration, "Guidance for Institutional Review Boards and Clinical Investigators 1998 Update: Medical Devices." Version Sep. 10, 2008.
U.S. Appl. No. 60/658,518, filed Mar. 4, 2005, publicly accessible Oct. 5, 2006.
Urquiola, Javier, et al., "Using Lead Foil as a Radiopaque Marker for Computerized Tomography Imaging When Implant Treatment Planning." The Journal of Prosthetic Dentistry, 1997.
U.S. Appl. No. 10/374,000, filed Feb. 25, 2003 Office Action dated Aug. 28, 2007.
U.S. Appl. No. 10/374,000, filed Feb. 25, 2003 Advisory Action dated Jan. 23, 2007.
U.S. Appl. No. 10/374,000, filed Feb. 25, 2003 Non-Final Office Action dated Feb. 13, 2006.
U.S. Appl. No. 10/374,000, filed Feb. 25, 2003 Non-Final Office Action dated May 20, 2009.
U.S. Appl. No. 10/374,000, filed Feb. 25, 2003 Non-final Office Action dated Mar. 20, 2008.
U.S. Appl. No. 10/374,000, filed Feb. 25, 2003 Office Action dated Feb. 28, 2007.
U.S. Appl. No. 10/374,000, filed Feb. 25, 2003 Office Action dated Jul. 28, 2006.
U.S. Appl. No. 10/374,000, filed Feb. 25, 2003 Office Action dated Sep. 30, 2008.
U.S. Appl. No. 10/374,000, filed Feb. 25, 2003 Response to Non-Final Office Action dated May 12, 2006.
U.S. Appl. No. 10/374,000, filed Feb. 25, 2003 Response to Office Action dated Dec. 28, 2006.
U.S. Appl. No. 10/374,000, filed Feb. 25, 2003 Response to Office Action dated Jun. 20, 2008.
U.S. Appl. No. 10/374,000, filed Feb. 25, 2003 Response to Office Action dated Mar. 30, 2009.
U.S. Appl. No. 10/374,000, filed Feb. 25, 2003 Response to Office Action dated May 28, 2007.
U.S. Appl. No. 10/374,000, filed Feb. 25, 2003 Response to Office Action dated Nov. 28, 2006.
U.S. Appl. No. 10/374,000, filed Feb. 25, 2003 Response to Office Action dated Oct. 31, 2007.
U.S. Appl. No. 10/374,000, filed Feb. 25, 2003 Response to Office Action dated Sep. 21, 2009.
U.S. Appl. No. 11/320,223, filed Dec. 28, 2005 Advisory Action dated Dec. 1, 2011.
U.S. Appl. No. 11/320,223, filed Dec. 28, 2005 Notice of Allowance dated Jan. 6, 2012.
U.S. Appl. No. 11/320,223, filed Dec. 28, 2005 Final Office Action dated Aug. 3, 2011.
U.S. Appl. No. 11/320,223, filed Dec. 28, 2005 Final Office Action dated Jun. 19, 2009.
U.S. Appl. No. 11/320,223, filed Dec. 28, 2005 Final Office Action dated Jun. 22, 2010.
U.S. Appl. No. 11/320,223, filed Dec. 28, 2005 Non-Final Office Action dated Feb. 13, 2008.
U.S. Appl. No. 11/320,223, filed Dec. 28, 2005 Non-Final Office Action dated Jan. 21, 2010.
U.S. Appl. No. 11/320,223, filed Dec. 28, 2005 Non-Final Office Action dated Mar. 16, 2011.
U.S. Appl. No. 11/320,223, filed Dec. 28, 2005 Non-Final Office Action dated Sep. 18, 2008.
U.S. Appl. No. 11/368,954, filed Mar. 6, 2006 Non-Final Office Action dated Jul. 21, 2009.
U.S. Appl. No. 11/368,954, filed Mar. 6, 2006 Notice of Allowance dated Jun. 24, 2010.
U.S. Appl. No. 11/368,954 filed March, 6, 2006 Final Office Action dated Jan. 27, 2010.
U.S. Appl. No. 11/368,954 filed March, 6, 2006 Supplemental Non-final Office Action dated Oct. 2, 2009.
U.S. Appl. No. 11/380,124, filed Apr. 25, 2006 Final Office Action dated Aug. 13, 2010.
U.S. Appl. No. 11/380,124, filed Apr. 25, 2006 Final Office Action dated Oct. 20, 2011.
U.S. Appl. No. 11/380,124, filed Apr. 25, 2006 Final Office Action dated Sep. 21, 2009.

* cited by examiner

IMPLANTABLE MEDICAL DEVICES INCLUDING SEPTUM-BASED INDICATORS

CROSS-REFERENCE TO RELATED APPLICATIONS

This application is a continuation of U.S. patent application Ser. No. 16/105,774, filed Aug. 20, 2018, now U.S. Pat. No. 10,773,066, which is a division of U.S. patent application Ser. No. 14/587,862, filed on Dec. 31, 2014, now U.S. Pat. No. 10,052,471, which is a division of U.S. patent application Ser. No. 12/617,981, filed Nov. 13, 2009, now U.S. Pat. No. 8,932,271, which claims the benefit of U.S. Provisional Patent Application No. 61/114,331, filed Nov. 13, 2008, and titled "Septum-Based Indicators for an Implantable Medical Device," each of which is incorporated herein by reference in its entirety.

BRIEF SUMMARY

Briefly summarized, embodiments of the present invention are directed to a medical device, such as an access port for providing subcutaneous access to a patient. The access port includes a septum including palpable identification indicia thereon. In particular, the access port in one embodiment includes a body that defines a fluid cavity and a needle-penetrable septum covering the fluid cavity for providing access thereto. The septum defines an outer periphery.

The palpable identification indicia of the septum are included as a plurality of raised palpation features. Each palpation feature includes a portion that extends in a radial direction beyond the outer periphery of the septum. The palpation features are therefore disposed relatively farther away from each other, simplifying palpation and identification thereof after the port has been subcutaneously implanted into a patient. The palpation features can be indicative of an attribute of the port, such as its ability to withstand fluid pressures and flow rates associated with power injection, for instance.

In other embodiments, the size, shape, number, and placement of the palpation features on the septum or other port surface can vary as appreciated by those skilled in the art.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Figure 1A:
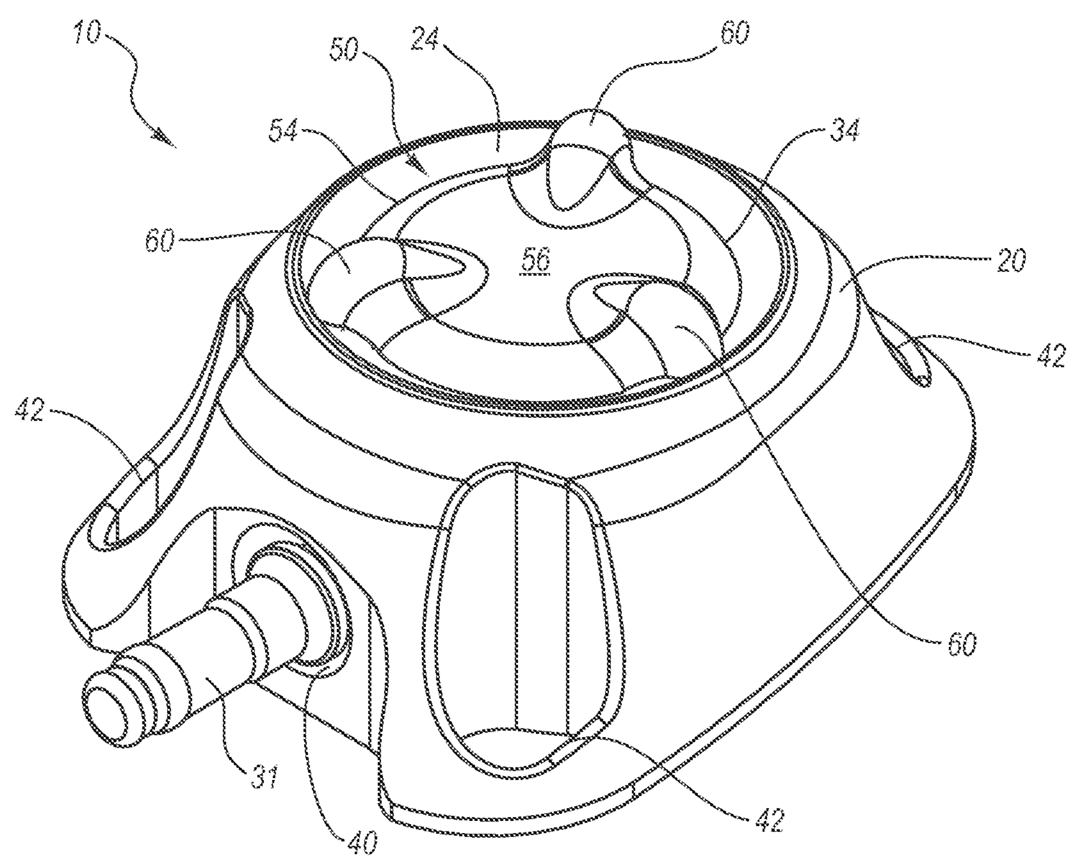
FIG. 1A is a perspective view of an implantable port including a septum configured according to one example embodiment.

Reference will now be made to figures wherein like structures will be provided with like reference designations. It is understood that the drawings are diagrammatic and schematic representations of exemplary embodiments of the present invention, and are neither limiting nor necessarily drawn to scale.

FIGS. 1A-15B depict various features of embodiments of the present invention, which are generally directed to medical devices including ports, also referred to herein as access ports, for implantation into the body of a patient. In some situations, it can be desirable to facilitate access to the vasculature of a patient for purposes of blood withdrawal and/or infusions, such as when the patient is ill and may repeatedly undergo such procedures. In one implementation, vascular access is established via a catheter situated within a blood vessel of the patient. A port, subcutaneously implanted in the patient, is placed in fluid communication with the catheter. Accordingly, infusions and blood withdrawals may be made percutaneously via the port, rather than directly through the wall of a blood vessel.

Reference is first made to FIGS. 1A-4, wherein an implantable port 10 is disclosed as configured in accordance with one example embodiment. As shown, the port 10 includes a body, or housing 20, which defines a fluid cavity 30 in communication with a rimmed opening, or aperture 34, on an upper surface of the port. The housing 20 defines a passageway 40 in fluid communication with the fluid cavity 30 into which a stem 31 is disposed, wherein the stem is configured for coupling with a lumen of a catheter so as to provide fluid communication between the catheter and the fluid cavity. In another embodiment, the stem can be integrally formed with the housing.

Figure 2:
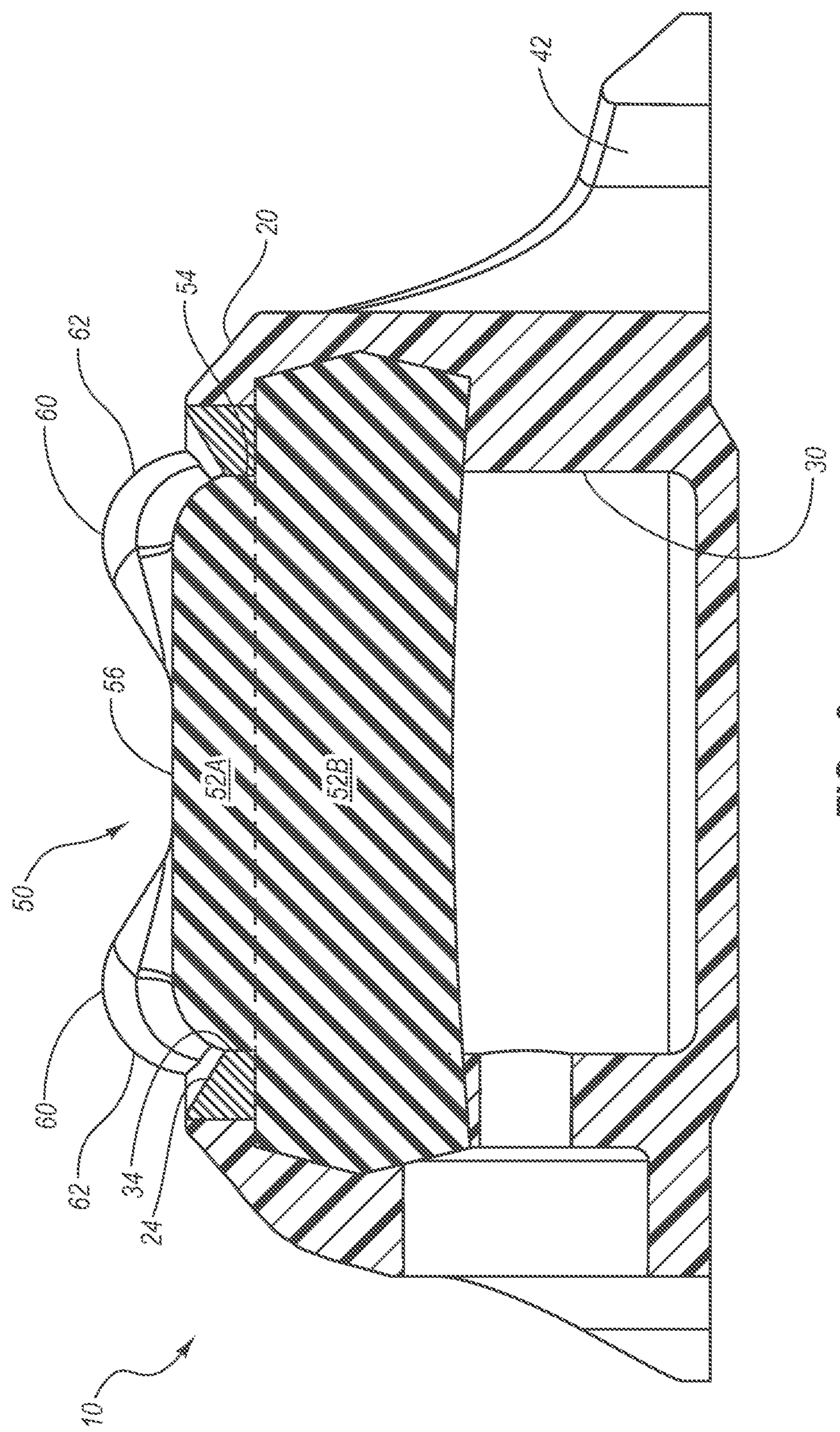
FIG. 2 is a cross sectional view of the port of FIG. 1B, taken along the line 2-2.

In the present embodiment, the port 10 includes a septum 50. The septum 50 is coupled with the housing 20 to cover the aperture 34 and the fluid cavity 30 defined by the housing, thus providing selective access to the fluid cavity. In the present embodiment, for example, the septum 50 includes an elastomeric material capable of being punctured by a needle, for example, a Huber needle, and substantially resealing upon removal of the needle. In one embodiment, the septum 50 includes silicone, though other materials can also be employed. In the illustrated embodiment, the port housing 20 includes a metallic material such as stainless steel or titanium, and the septum 50 is secured in place in the housing by a metallic retaining ring 24 that is press fit into the housing, as shown in FIG. 2. As will be seen below, the principles of the present disclosure can be employed with other port materials and configurations. These and other configurations are therefore contemplated.

The port 10 is configured to be implanted subcutaneously within a patient and operably connected to a catheter that, in turn, is disposed within a vein or other vessel. Accordingly, when the catheter is coupled with the stem 31 of the port 10, fluid communication can be established with the vessel via the fluid cavity 30, such as by an infusion needle inserted through the septum 50 of the port. A plurality of suture holes 42 can be included in the housing 20 so as to facilitate securement of the port 10 to the tissue of the patient when implanted.

The septum 50 in the present embodiment is defined by a body 52 including an upper body portion 52A that is generally exposed through the aperture 34 of the port 10 and a lower body portion 52B that is generally included within the interior of the port housing 20. The upper body portion 52A and lower body portion 52B define a juncture 53. The upper body portion 52A includes a top surface 56 and an outer periphery 54. Though the present embodiments deal particularly with the outer periphery 54, i.e., a first outer periphery of the septum upper body portion 52A, the lower body portion 52B can be considered to define a second outer periphery including a relatively larger diameter than that of the first outer periphery.

In the present embodiment the periphery 54 of the upper body portion 52A of the septum 50 is circular to match the circular aperture 34, but in other embodiments it is appreciated that the outer periphery of the septum could define other shapes, including triangular, square, polygonal, other geometric shapes, etc. To the extent that the periphery of the septum defines other shapes, in some embodiments the shape of the aperture can also be modified to correspond in shape to that of the septum.

Figure 1B:
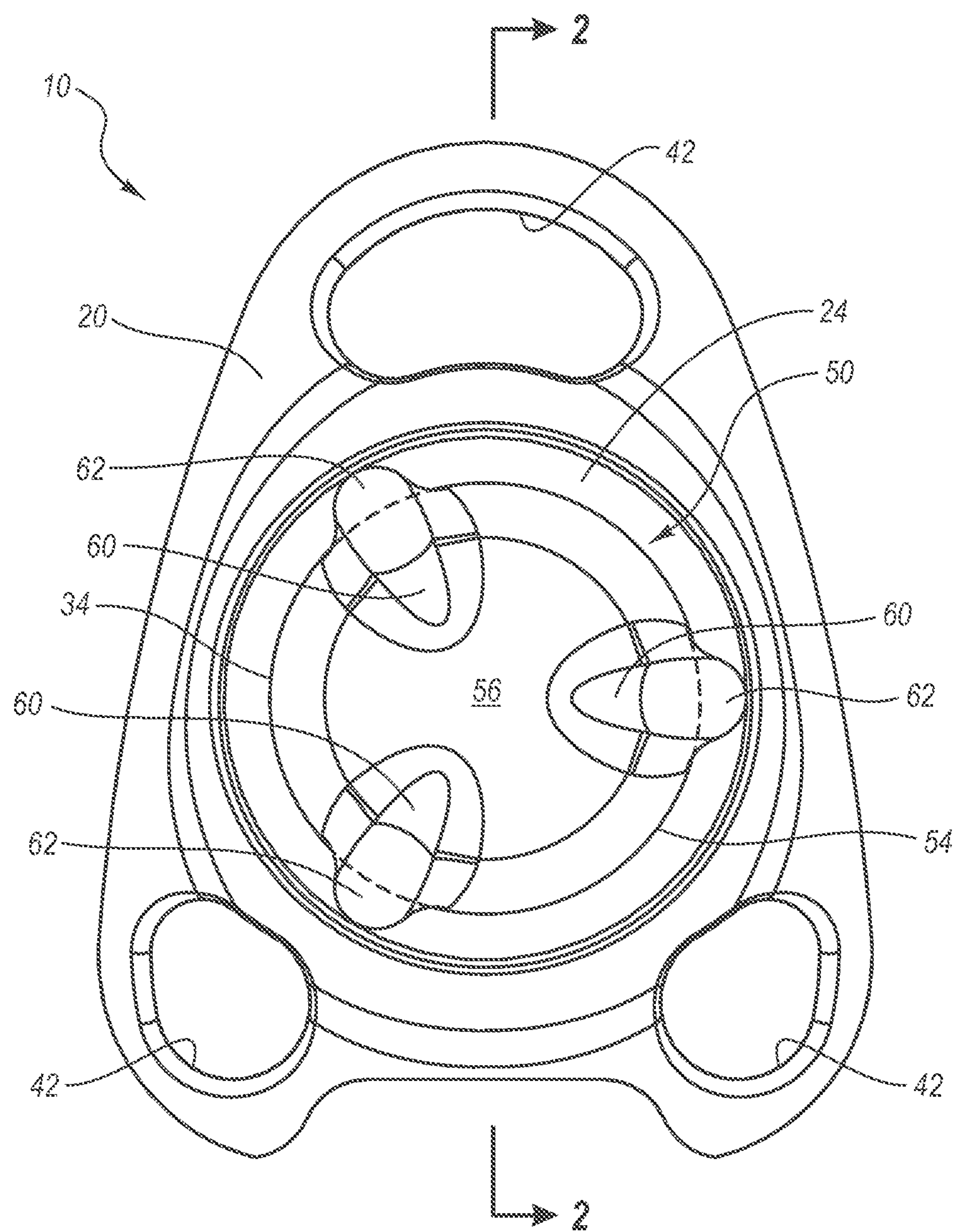
FIG. 1B is a top view of the port of FIG. 1A.

According to the present embodiment, a plurality of palpation features is included on the septum 50. As shown in FIGS. 1A-4, the palpation features are included as three protrusions 60 that extend from a surface of the septum 50. The three protrusions 60 are equidistantly spaced at substantially regular intervals around an outer portion of the septum 50 as to define end points, or vertices, of an imaginary triangle such as an equilateral triangle in the present embodiment. As best seen in FIG. 1B, the protrusions 60 generally align with the vertices of the generally triangularly-shaped port housing 20. The protrusions 60 extend upward from the generally flat septum top surface 56 such that the protrusions provide surface features to a top profile of the port 10 from the perspective shown in FIG. 2.

Note that, though three are used here, fewer or more palpable protrusions can be included on the septum top surface. Indeed, only one protrusion can be employed if desired. Also, though the port shown here is a port with a singular fluid cavity, multi-lumen ports including a plurality of fluid cavities and corresponding septa can include the palpation features discussed herein. The spacing, shape, and size of the palpation features can vary in a number of ways, some of which are described further below.

As best seen in FIG. 1B, the protrusions 60 are shaped and positioned as to include a radially outward portion 62 that radially extends past the circular outer periphery 54 of the septum 50. Thus, the radially outward portion 62 of each protrusion 60 extends beyond, or overlaps, the aperture 34 and thus extends over a portion of the retaining ring 24. The radially outward portion 62 of each protrusion 60 includes a bottom surface 55 extending angularly away from the upper body portion 52A of the septum 50, as shown in FIG. 4.

The overlapping aspect of the protrusions 60 causes a center point of each protrusion to be disposed relatively farther away from the other protrusions than if the protrusions were confined within the bounds defined by the septum outer periphery 54. This in turn enables the protrusions to be more easily palpated and identified by a clinician performing the palpation for an implanted port than if the protrusions were closer set. Thus, the tactile acuity of the clinician palpating the port 10 is preserved without increasing the size of either the septum or its protrusions. Desire for increased tactile acuity has increased in recent years in light of the trend toward a reduction in size of manufactured ports, and by extension, septum size.

Figure 4:
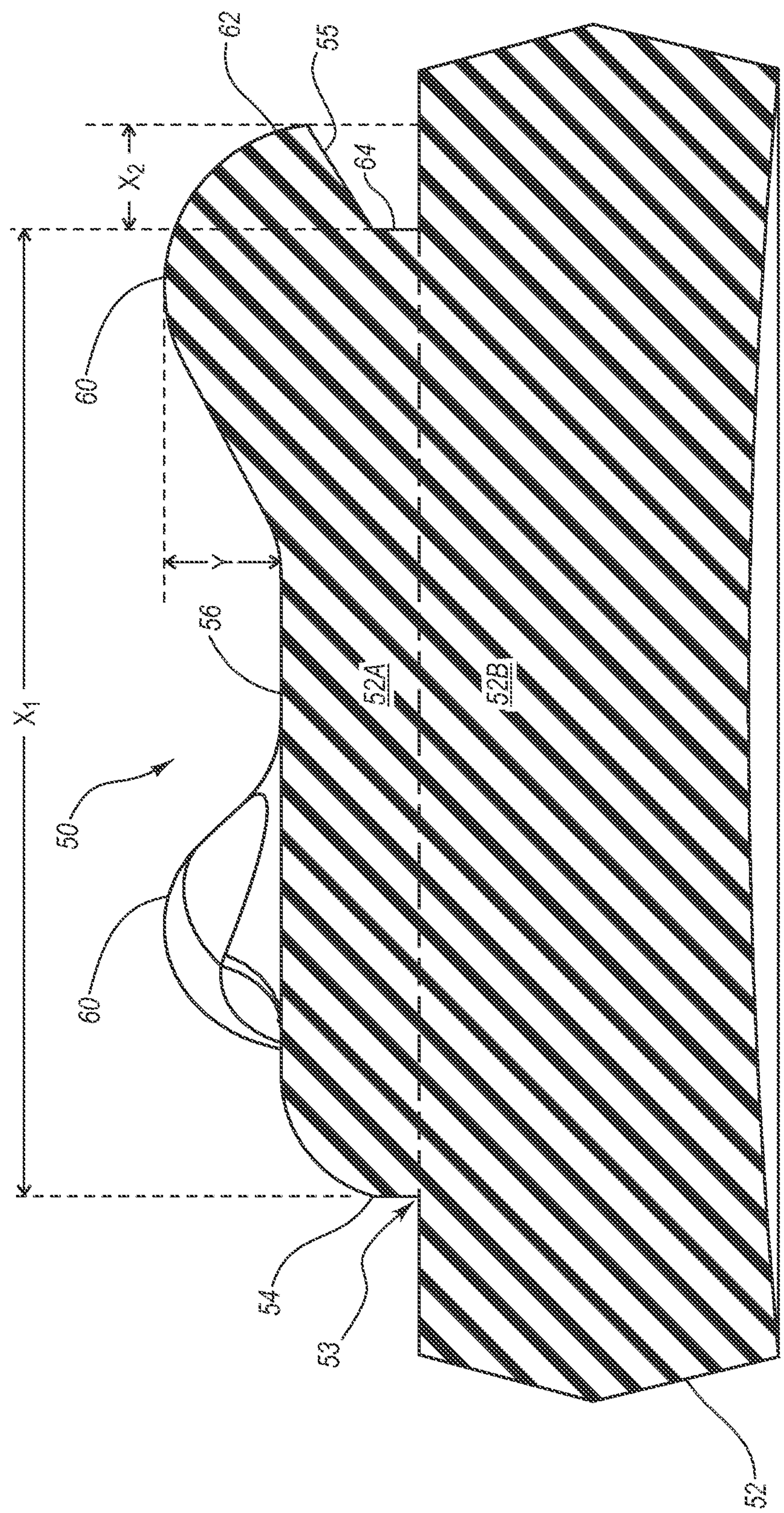
FIG. 4 is a cross sectional view of the septum of FIG. 3, taken along the line 4-4.

In greater detail, FIG. 4 shows one of the protrusions 60 of the septum 50 in cross section, wherein a notch 64 is defined by virtue of the overlapping nature of the protrusion. The notch 64 enables the protrusion to extend over the edge of the aperture 34, defined in this embodiment by the retaining ring 24, without interfering with the retaining ring. Of course, the size and shape of the notch and protrusion can be modified to adapt to a particular port configuration.

Figure 3:
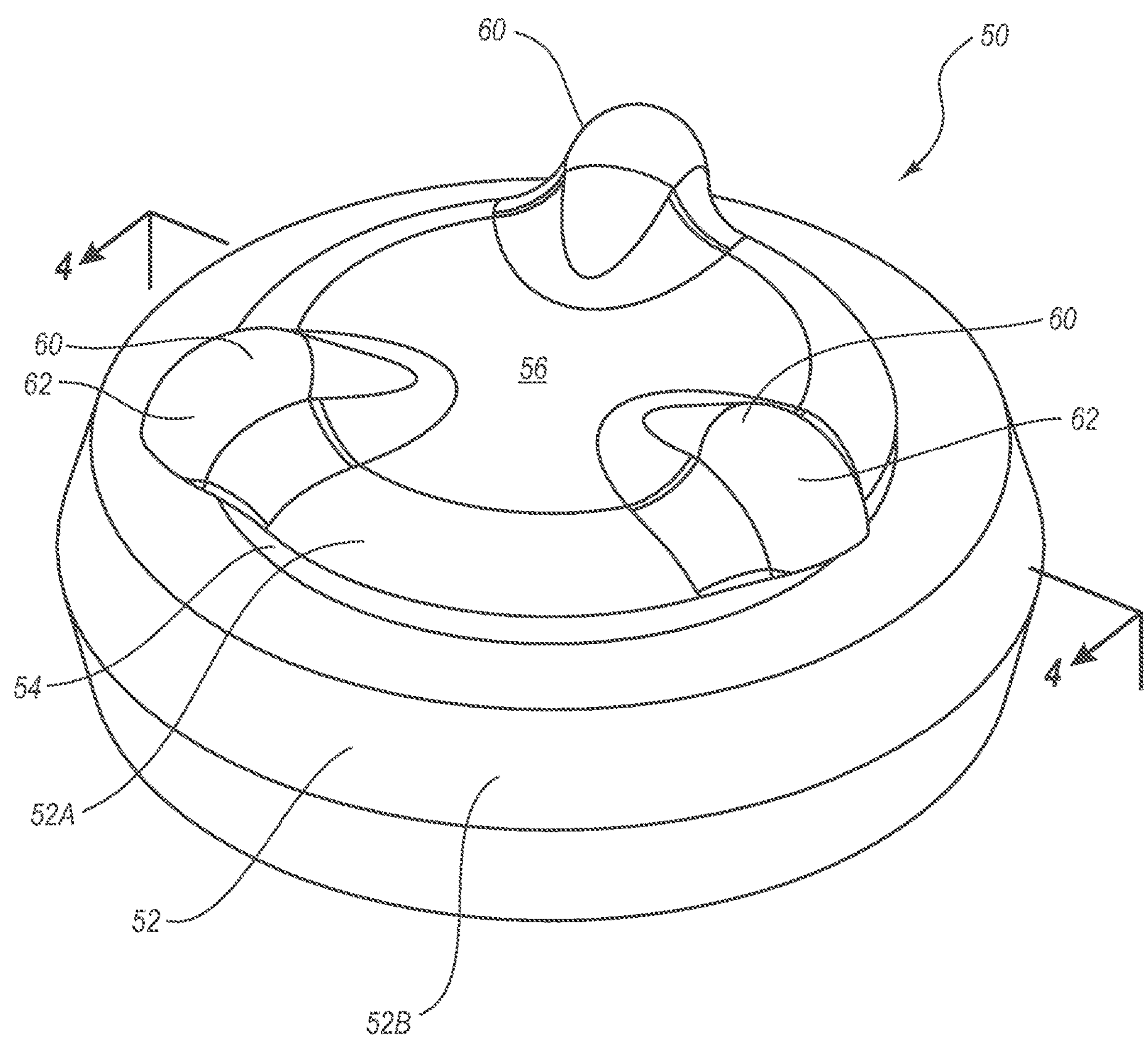
FIG. 3 is a perspective view of the septum included in the port of FIG. 1A.

The protrusions 60 in the present embodiment are oblong-shaped, generally resembling a seed or tear drop shape, and include a smoothly contoured surface, as best seen in FIGS. 1B and 3. The smooth contour of the protrusions 60 assists in reducing tissue irritation when the port 10 is implanted in the patient. In the present embodiment where the septum 50 generally defines a disc-like shape including an outer periphery diameter of about 0.42 inch (indicated at $X_1$ on FIG. 4), the protrusions 60 axially extend a distance of about 0.046 inch above the top surface 56 of the septum body 52 (indicated at Y on FIG. 4) and about 0.055 inch radially beyond the periphery 54 (indicated at $X_2$ on FIG. 4), though other size dimensions are of course possible. The protrusions 60 are integrally formed with the septum 50 in the present embodiment, but could be separately formed and attached to the septum in another embodiment. Note that the shapes of the protrusions can be shaped in other ways, as will be seen further below. Note further that each protrusion on the septum can include a different shape with respect to the other protrusions, if desired.

In one embodiment, the palpation features, i.e., protrusions 60 of the septum 50, can permit a clinician to properly identify a predetermined attribute or characteristic of the port 10. The attribute of the port 10 in one embodiment is the suitability of the port to withstand relatively high fluid flow and/or fluid pressure rates therethrough, commonly referred to as "power injection." Such high pressure and flow rates are typically associated with power injection of fluids through the port during relatively demanding procedures (e.g., computed tomography, or "CT," scans), in which contrast media is rapidly infused through the port and connected catheter and into a vascular system. For instance, in one embodiment power injection includes fluid infusion by a power injection machine producing fluid pressures of up to about 325 psi, resulting in fluid pressures in the port

10 between about 50 and about 90 psi and fluid flow through the port at a rate between about two and about five milliliters per second. Other flow rates and fluid pressures are, of course, possible.

During power injection, a needle can be inserted in a septum of the port and connected to a power injection machine, which can introduce contrast media through the port at a relatively high flow rate, as detailed above. Certain ports may not be able to withstand pressures corresponding to high flow rates during power injection. Accordingly, it is often necessary to determine whether an implanted port is compatible for power injection.

The protrusions 60 enable identification of a port as power injectable, in one embodiment. In particular, after subcutaneous implantation of the port 10 in a patient, a clinician cannot visually observe the port to determine whether it is suitable for power injection. With a port 10 configured as shown in FIGS. 1A-4, the clinician can feel or palpate the three protrusions 60 through the skin to determine that the port is suitable for power injection. In addition, other information regarding the port 10 can be gathered by palpation, including the general orientation of the port, location the septum 50, etc.

In addition to its suitability for power injection, in other embodiments other predetermined attributes or characteristics of the port can be indicated by the protrusions described herein. Such attributes include, for example, the type of catheter to which the port is connected, e.g., whether the catheter distal tip is open-ended or includes distal valve, the type of material from which the port is constructed, etc. Such ability to determine the predetermined characteristic(s) of the port is useful for ports of all types, including those made from radio-translucent materials, which are not sufficiently imaged radiographically.

Figure 5:
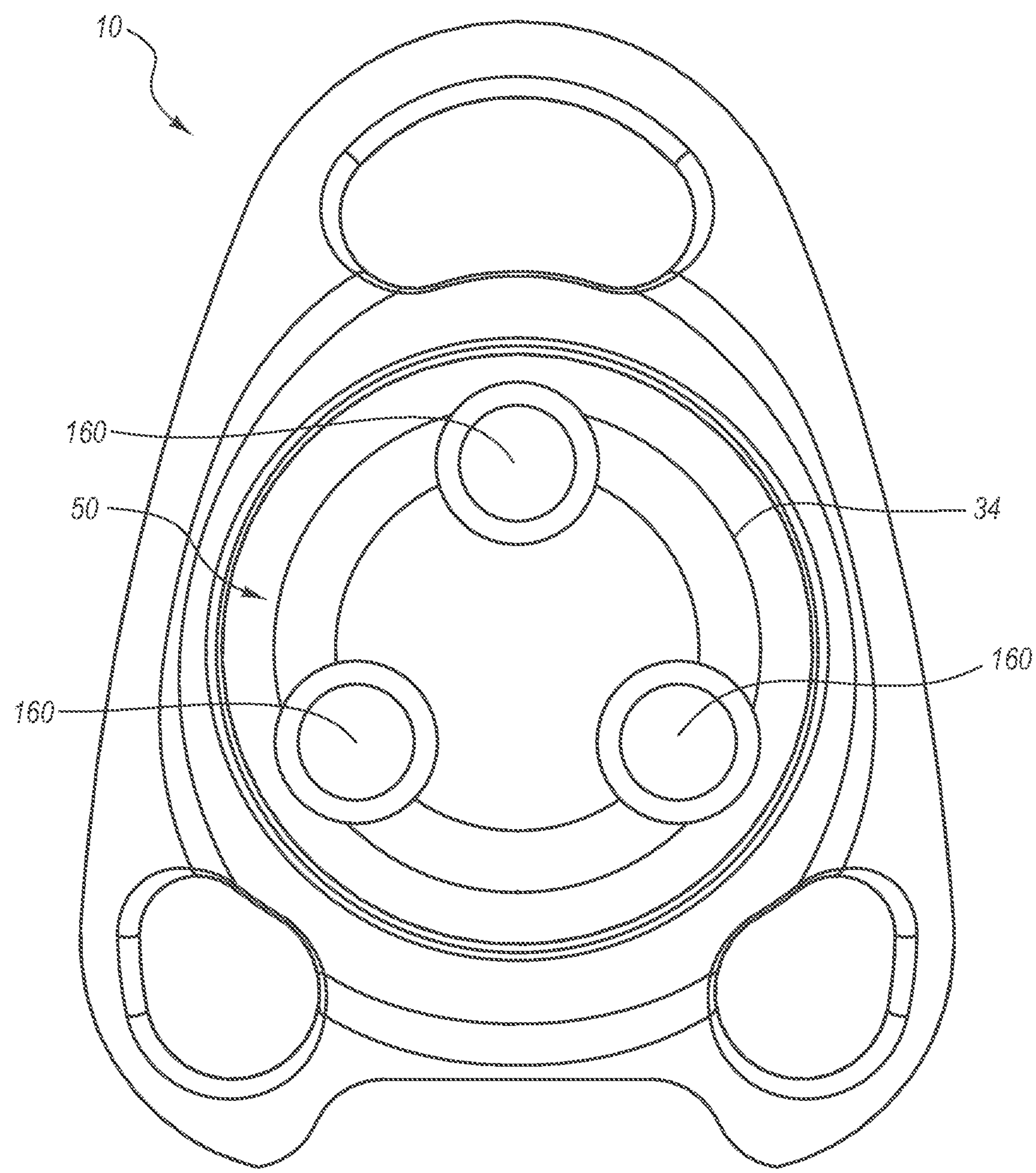
FIG. 5 is a top view of an implantable port including a septum configured according to one embodiment.
Figure 6:
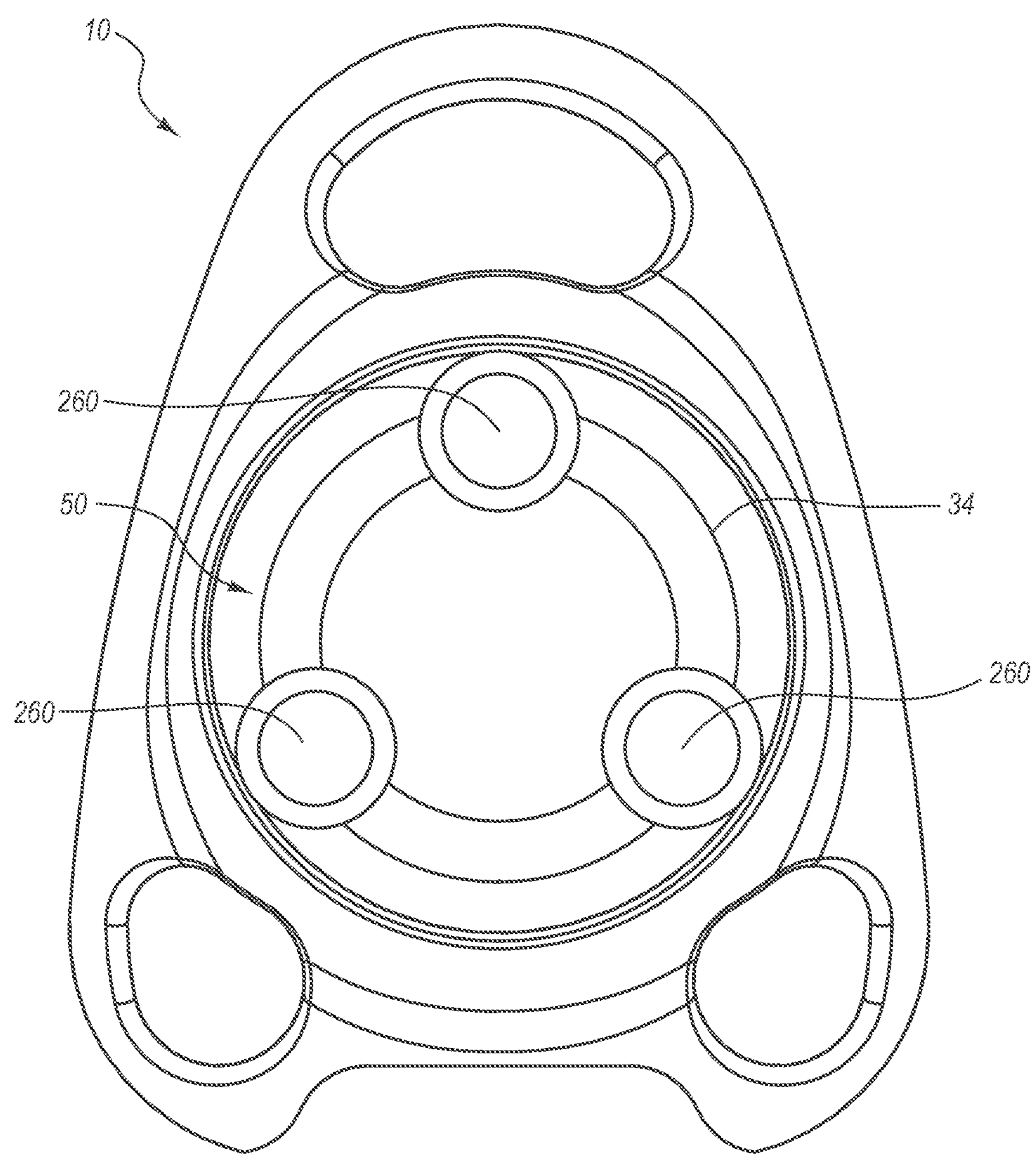
FIG. 6 is a top view of an implantable port including a septum configured according to one embodiment.

As already described, the protrusions 60 in FIGS. 1A-4 are tear drop-shaped to provide a smooth contour surface and to avoid irritating body tissue proximate the port implanted location. In other embodiments, though, the shape, size, number, and placement of the palpation features can be modified from what is explicitly shown and described herein in order to suit a particular need. FIGS. 5-12 give several examples of different possible protrusion configurations for the septum 50 of the port 10. FIG. 5 shows overlapping protrusions 160 defining a flat cylindrical shape. FIG. 6 depicts protrusions 260 defining flat cylindrical shapes similar to those shown in FIG. 5, wherein the protrusions 260 overlap the aperture 34 a relatively more than the protrusions 160 of FIG. 5.

Figure 7:
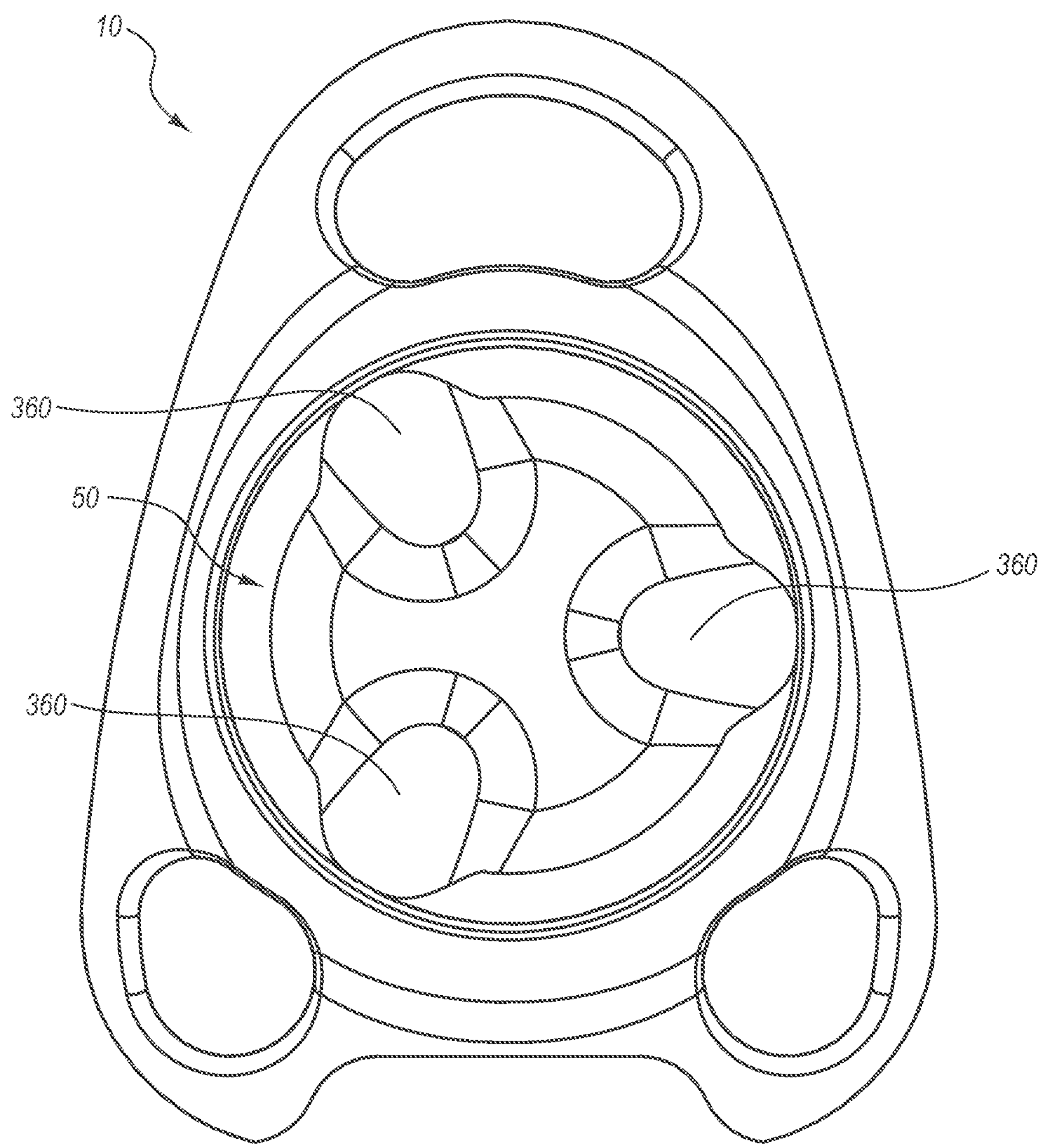
FIG. 7 is a top view of an implantable port including a septum configured according to one embodiment.
Figure 8:
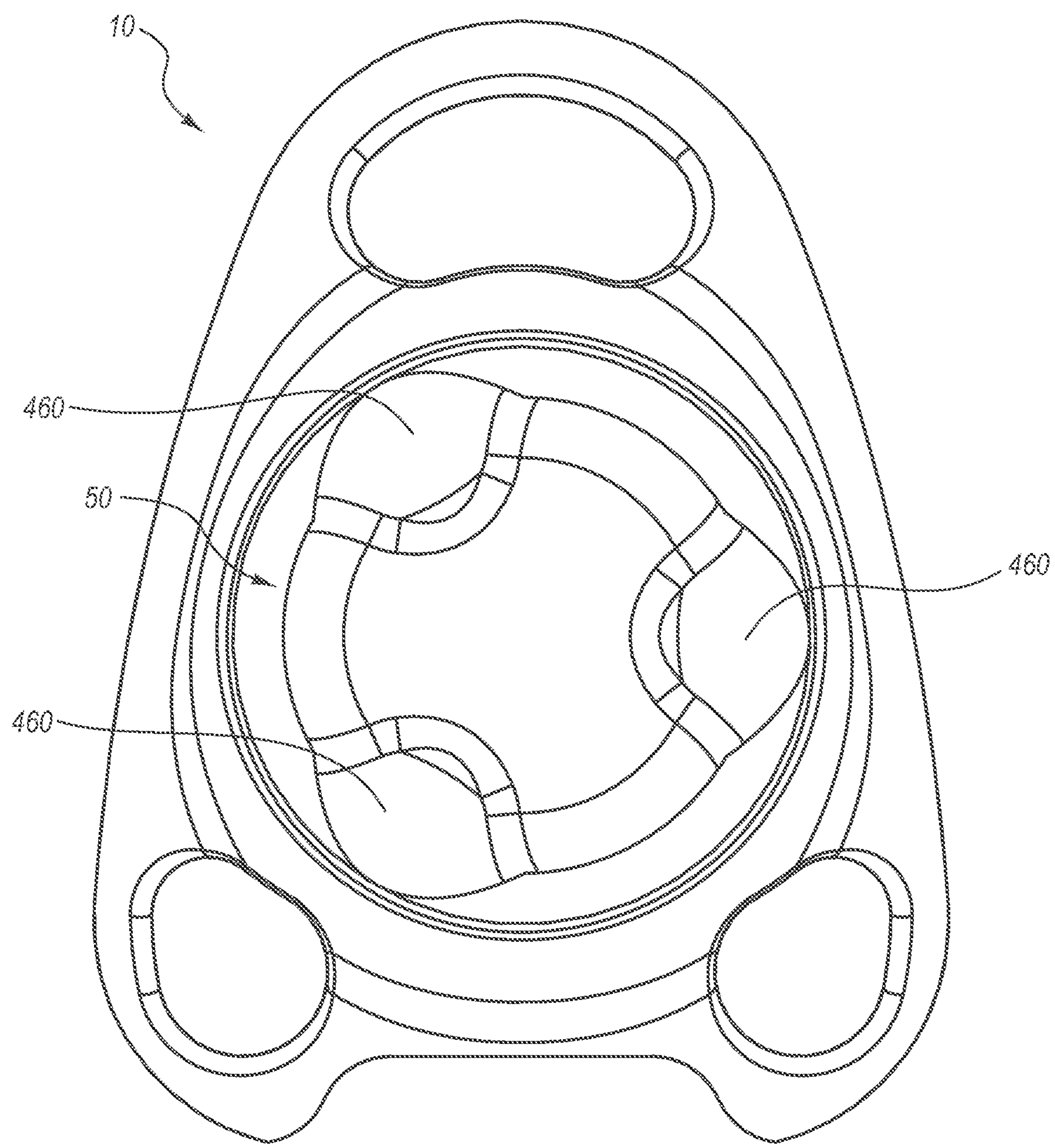
FIG. 8 is a top view of an implantable port including a septum configured according to one embodiment.
Figure 9:
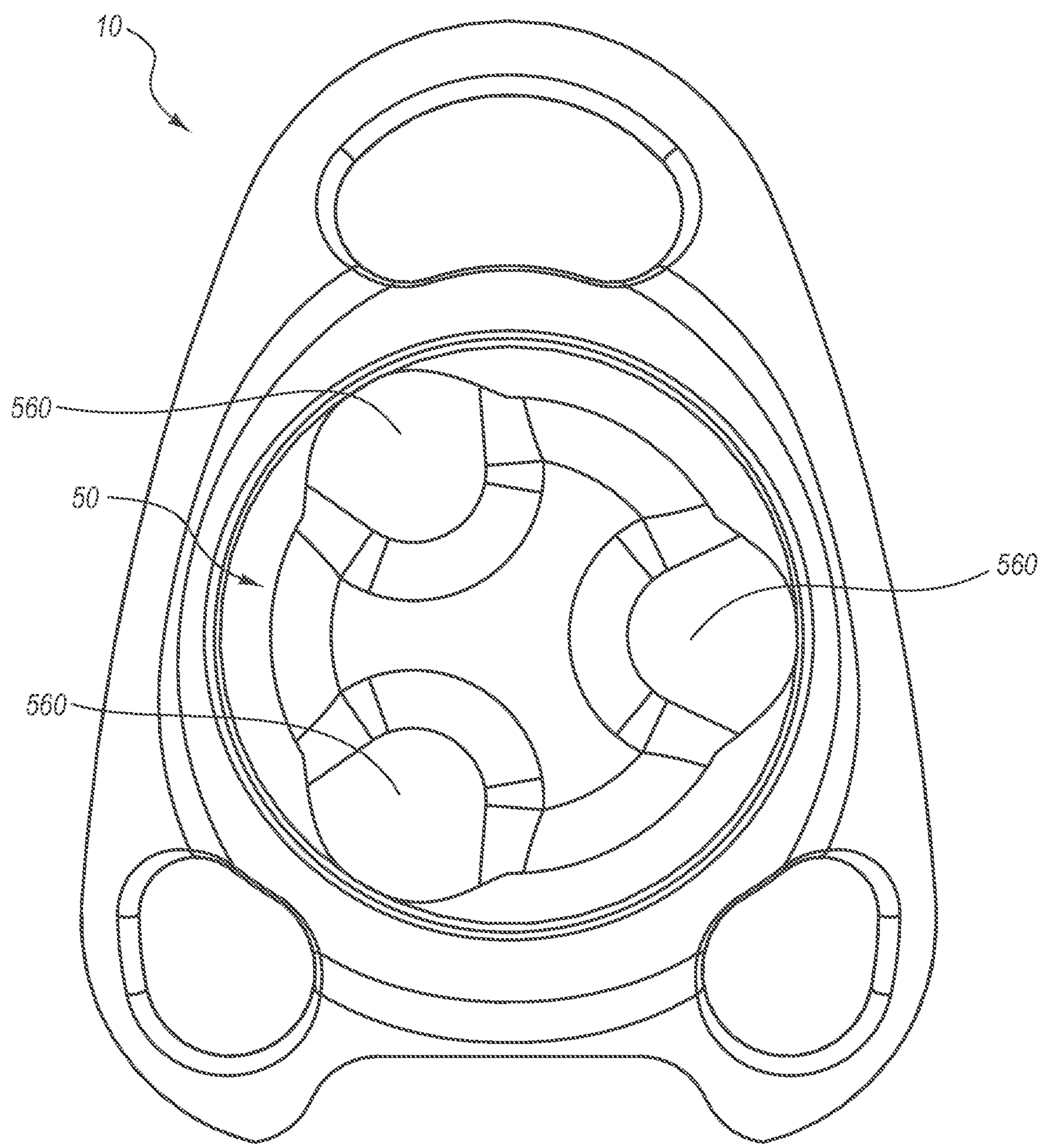
FIG. 9 is a top view of an implantable port including a septum configured according to one embodiment.
Figure 10:
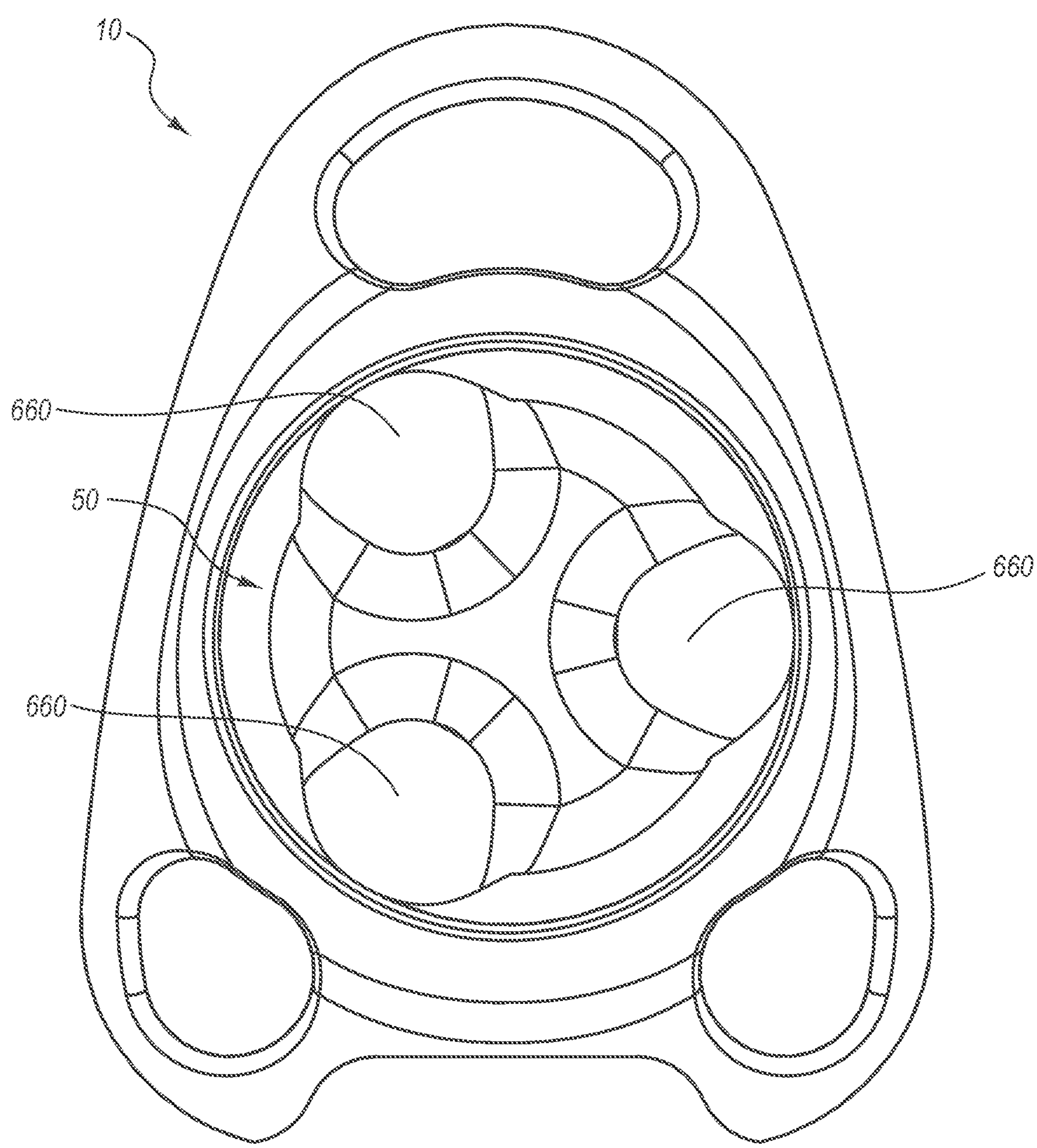
FIG. 10 is a top view of an implantable port including a septum configured according to one embodiment.
Figure 11:
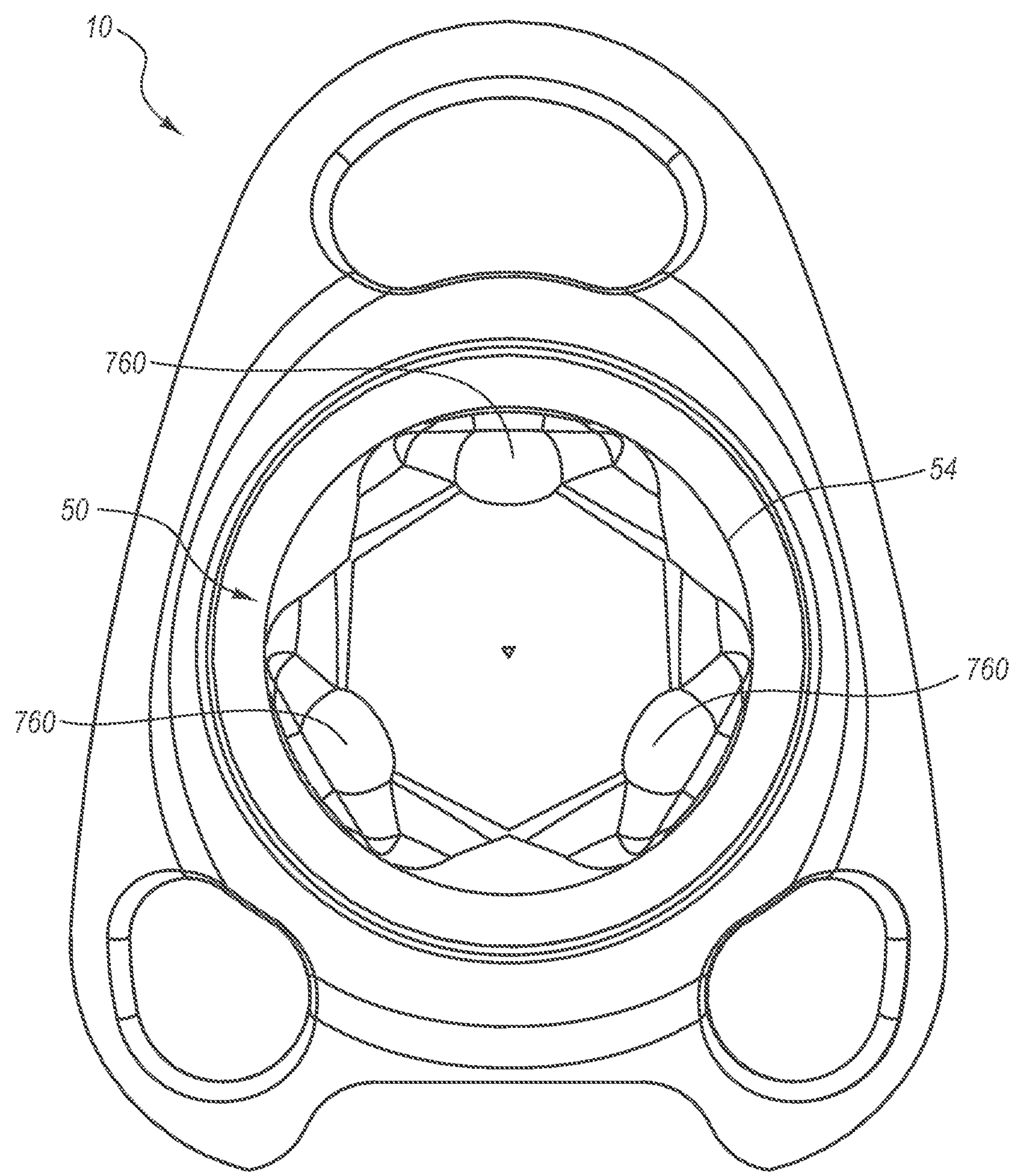
FIG. 11 is a top view of an implantable port including a septum configured according to one embodiment.
Figure 12:
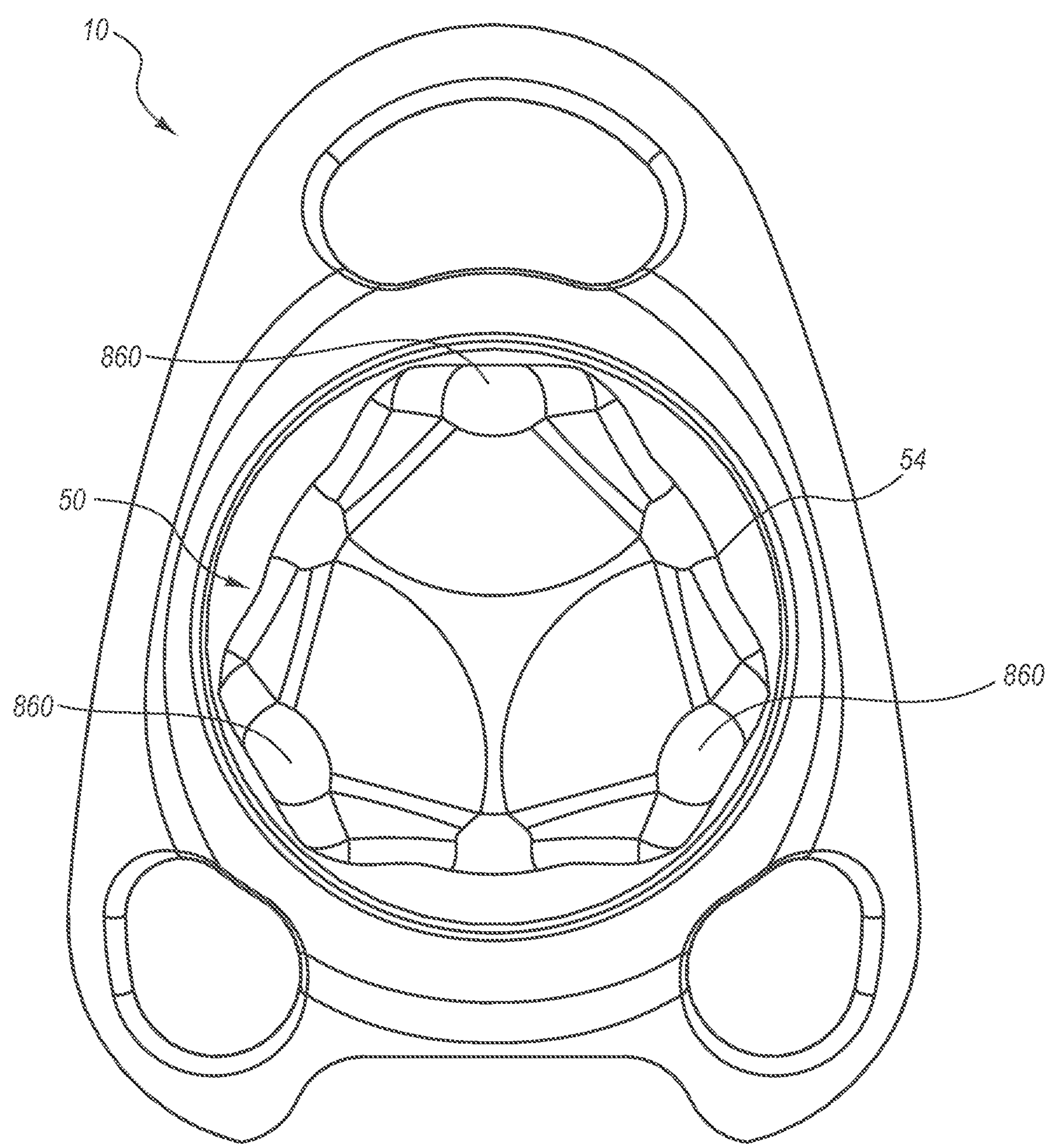
FIG. 12 is a top view of an implantable port including a septum configured according to one embodiment.

FIGS. 7 and 8 depict protrusions 360 and 460 that define oblong and roughly conical shapes, respectively, while FIGS. 9 and 10 respectively depict semi-spherical protrusions 560 and 660. FIGS. 11 and 12 show relatively thin protrusions 760 and 860 disposed with their long axes extending tangentially to the septum outer periphery 54. Note that the outer periphery 54 of the septum 50 in FIG. 12 generally defines a triangular shape.

Figure 13:
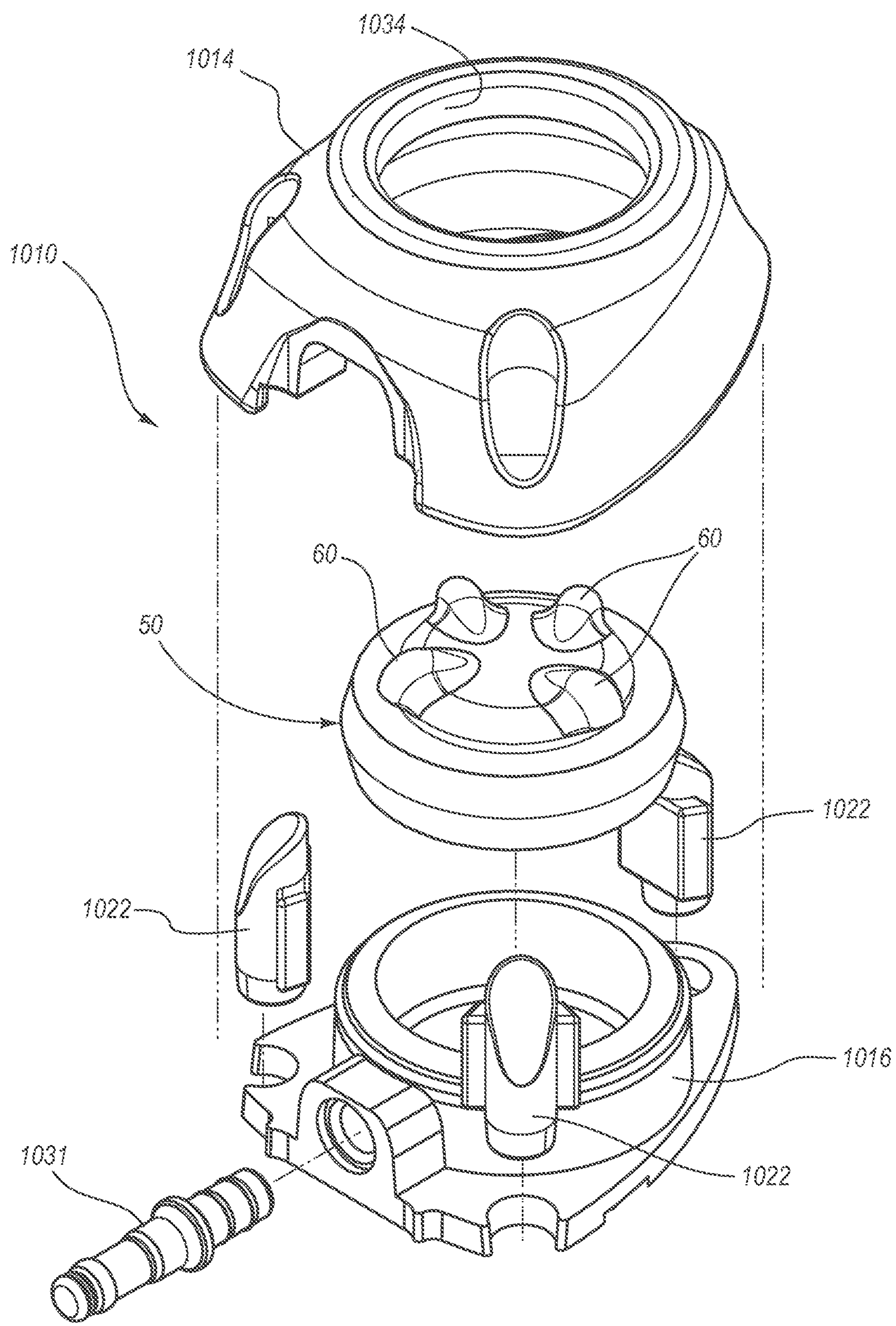
FIG. 13 is an exploded perspective view of an implantable port including a septum configured according to one embodiment.

As described above, the principles of the present disclosure can be applied to ports from a variety of materials. FIG. 13 gives one example of this, wherein a port 1010 is shown including a cap 1014 and a base 1016, both formed from an engineering plastic material, such as Polyoxymethylene ("POM"), also known as an acetal resin, or other suitable material. The septum 50 including the protrusions 60 is sandwiched between the cap 1014 and base 1016 so as to be captured therebetween when the cap and base are mated together and such that the protrusions overlap past an aperture 1034 defined by the cap 1014. Note that in the illustrated embodiment, four overlapping protrusions are included on the septum 50, in contrast to embodiments described earlier. Suture plugs 1022 and a stem 1031 are also included with the port 1010.

Figure 15B:
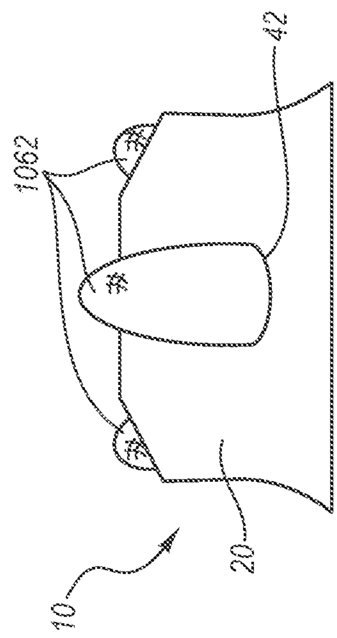
FIGS. 15A and 15B are a top and side view, respectively, of an implantable port configured according to one embodiment.
Figure 14:
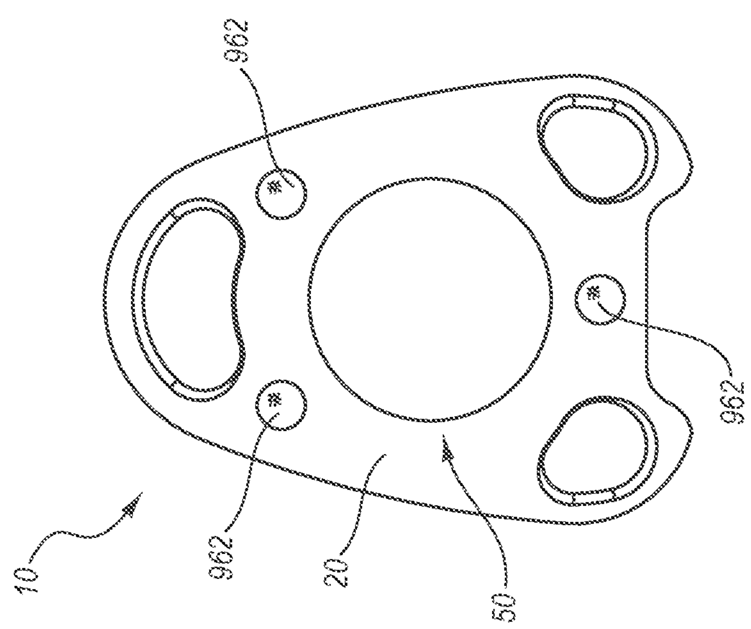
FIG. 14 is a top view of an implantable port configured according to one embodiment.

Palpation features can be included on the port in other configurations, as shown in FIGS. 14-15B. In FIG. 14, a plurality of protrusions 962 is included on the housing 20 of the port 10. The protrusions 962 can be hard or resilient and are spaced so as to enable palpation of the port 10 when subcutaneously implanted. The protrusions 962 can be adhered to the port housing surface 20 via an adhesive, can be inserted into corresponding holes defined in the housing, or can be included in other suitable ways. Note that, as before, the size, shape, number, and configuration of the protrusions can vary from what is explicitly shown here.

Figure 15A:
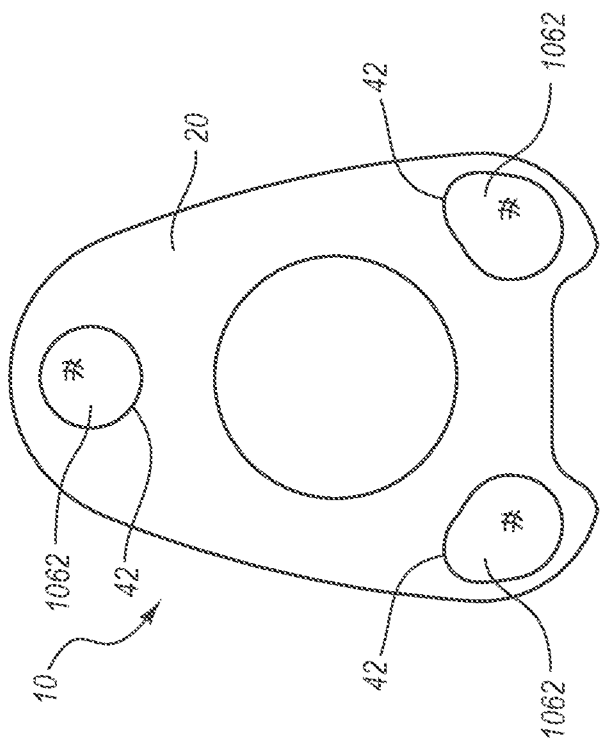

FIGS. 15A and 15B show a plurality of protrusions 1062 inserted into the suture holes 42 of the port housing 20. The protrusions 1062 are resilient and extend a predetermined distance above a top surface of the port 10 so as to enable palpation thereof when the port is implanted. The protrusions 1062 are inserted and secured in the suture holes 42 via a friction fit, mechanical capture, or other suitable method. Of course, the number, size, position, and shape of both the suture holes and corresponding protrusions can vary from what is explicitly described herein.

The number, size, position, and shape of the palpation features can be modified while residing within the scope of embodiments of the present invention. In addition to the above embodiments, it is appreciated, for example, that the protrusions can define patterns other than equilateral triangles, including acute triangles, obtuse triangles, squares, etc. Additionally, one, two, three, four, five, or more protrusions could be used. In one embodiment, the port includes two or more septa with protrusions extending from each. The protrusions can define a variety of different shapes, and may be sized differently. Indeed, the protrusions can include configurations such as those shown and described in U.S. Pat. No. 8,177,762, which is incorporated herein by reference in its entirety. Thus, the foregoing examples are merely illustrative in nature.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A septum providing access to a fluid cavity of a subcutaneously implanted access port, the septum comprising:

a lower portion having a first diameter;

an upper portion joined to the lower portion at a juncture, the upper portion having a second diameter less than the first diameter at the juncture; and a plurality of palpation features joined to the upper portion, each of the plurality of palpation features including:

a first end adjacent a central axis of the septum; and a second end extending radially outward to overlap the juncture, the second end including a bottom surface extending angularly away from the upper portion.

2. The septum according to claim 1, wherein the plurality of palpation features includes three equidistantly spaced protrusions.

3. The septum according to claim 2, wherein each of the three equidistantly spaced protrusions is tear-shaped.

4. The septum according to claim 1, wherein the plurality of palpation features are designed to indicate an attribute of the subcutaneously implanted access port.

5. The septum according to claim 4, wherein the attribute of the subcutaneously implanted access port is a capability to support fluid flow therethrough at a rate of at least five milliliters per second.

6. The septum according to claim 4, wherein the attribute of the subcutaneously implanted access port is suitability for power injection of a fluid through the access port.

7. The septum according to claim 4, wherein the attribute of the subcutaneously implanted access port is a material from which the subcutaneously implanted access port is formed.

8. The septum according to claim 1, wherein the plurality of palpation features are designed to indicate an attribute of a catheter connected to the subcutaneously implanted access port.

9. The septum according to claim 8, wherein the attribute of the catheter is whether a distal tip of the catheter is open-ended or valved.

10. The septum according to claim 1, wherein each of the plurality of palpation features have a shape selected from the group consisting of tear-shaped, triangular, semi-spherical, round, elongate, and oblong.

* * * * *